(12) United States Patent
Chellappan et al.

(10) Patent No.: US 11,685,725 B2
(45) Date of Patent: *Jun. 27, 2023

(54) YAP1 INHIBITORS THAT TARGET THE INTERACTION OF YAP1 WITH OCT4

(71) Applicant: H. LEE MOFFITT CANCER CENTER AND RESEARCH INSTITUTE, INC., Tampa, FL (US)

(72) Inventors: Srikumar Chellappan, Tampa, FL (US); Nicholas J. Lawrence, Tampa, FL (US); Sujeewa Ranatunga Mahanthe Mudiyanselage, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/980,538

(22) PCT Filed: Mar. 14, 2019

(86) PCT No.: PCT/US2019/022337
§ 371 (c)(1),
(2) Date: Sep. 14, 2020

(87) PCT Pub. No.: WO2019/178401
PCT Pub. Date: Sep. 19, 2019

(65) Prior Publication Data
US 2021/0363128 A1    Nov. 25, 2021

Related U.S. Application Data

(60) Provisional application No. 62/643,032, filed on Mar. 14, 2018.

(51) Int. Cl.
| | | |
|---|---|---|
| *C07D 401/06* | (2006.01) | |
| *A61K 45/06* | (2006.01) | |
| *C07D 211/34* | (2006.01) | |
| *C07D 401/10* | (2006.01) | |
| *C07D 401/12* | (2006.01) | |

(52) U.S. Cl.
CPC .......... *C07D 401/06* (2013.01); *A61K 45/06* (2013.01); *C07D 211/34* (2013.01); *C07D 401/10* (2013.01); *C07D 401/12* (2013.01)

(58) Field of Classification Search
CPC .... A61K 45/06; C07D 401/06; C07D 211/34; C07D 401/10; C07D 401/12
See application file for complete search history.

(56) References Cited

U.S. PATENT DOCUMENTS

| | | | |
|---|---|---|---|
| 6,147,083 A | 11/2000 | Russell | |
| 8,623,893 B2 | 1/2014 | Lassalle et al. | |
| 10,906,874 B2 * | 2/2021 | Chellappan | .......... C07D 405/06 |
| 11,530,182 B2 * | 12/2022 | Chellappan | .......... C07D 211/58 |
| 2010/0076015 A1 | 3/2010 | Evans et al. | |
| 2010/0286035 A1 | 11/2010 | Ohtaki et al. | |
| 2015/0157584 A1 | 6/2015 | Guan et al. | |
| 2017/0319648 A1 | 11/2017 | Li | |
| 2019/0375709 A1 * | 12/2019 | Chellapan | ............. C07C 237/22 |
| 2021/0130297 A1 * | 5/2021 | Chellappan | ............. A61P 35/00 |

FOREIGN PATENT DOCUMENTS

| | | | |
|---|---|---|---|
| CN | 102076666 A | 5/2011 | |
| CN | 102946882 A | 2/2013 | |
| WO | 2000/043415 | 7/2000 | |
| WO | 03/009847 | 2/2003 | |
| WO | 2003/009847 A1 | 2/2003 | |
| WO | 2004020435 A1 | 3/2004 | |
| WO | 2005/077914 | 8/2005 | |
| WO | WO-2005121090 A1 * | 12/2005 | ........... C07D 211/64 |
| WO | 2009044918 A1 | 4/2009 | |
| WO | 2009129508 A1 | 10/2009 | |
| WO | 2011/097300 | 8/2011 | |
| WO | 2014097151 A1 | 6/2014 | |
| WO | 2015/019325 | 2/2015 | |
| WO | 2016/058547 | 4/2016 | |
| WO | 2018053446 A1 | 3/2018 | |
| WO | 2019090069 A1 | 5/2019 | |
| WO | 2019090076 A1 | 5/2019 | |
| WO | 2019175253 A1 | 9/2019 | |

OTHER PUBLICATIONS

Song; Mol Can Ther 2018, 17, 443-454. https://doi.org/10.1158/1535-7163.MCT-17-0560 (Year: 2018).*
Examination report issued for Chilean Application No. 2364-2020, dated Sep. 13, 2021.
Extended European Search report issued for Application No. 19766810.6, dated Nov. 15, 2021.
Office Action issued for Japanese Application No. 2019-515263, dated Aug. 10, 2021.
International Preliminary Report on Patentability Opinion issued for International Application No. PCT/US2017/052103, dated Mar. 28, 2019, 10 pages.
International Search Report and the Written Opinion issued for International Application No. PCT/US2017/052103, dated Jan. 5, 2018, 15 pages.

(Continued)

*Primary Examiner* — Daniel R Carcanague
(74) *Attorney, Agent, or Firm* — Meunier Carlin & Curfman LLC

(57) ABSTRACT

Binding of the transcriptional co-activator, YAP1, to the transcription factor Oct4, induces Sox2, which is a transcription actor necessary for the self-renewal of stem-like cells from non-small cell lung cancer. The WW domain of YAP1 binds to the PPxY motif of Oct4 to induce Sox2. Delivering a peptide corresponding to the WW domain could prevent the induction of Sox2 and sternness. Similarly, peptides and mimetics of the PPxY motif would be able to inhibit sternness. Disclosed are compounds that affect the Yap1:Oct4 interaction.

29 Claims, 12 Drawing Sheets

Specification includes a Sequence Listing.

(56) References Cited

OTHER PUBLICATIONS

International Search Report and the Written Opinion issued for International Application No. PCT/US2019/022337, dated Jun. 3, 2019.
Chemical Abstract Compound, STN express, RN 754928-65-9 (Entered STN: Oct. 1, 2004).
Chemical Abstract Compounds, STN express, RN 1824945-77-8 (Entered STN: Dec. 8, 2015).
Chemical Abstract Compounds, STN express, RNs 1315859-64-3, 1315837-45-6 (Entered STN: Aug. 11, 2011).
Chemical Abstract Compounds, STN express, RN 1293634-04-4 (Entered STN: May 12, 2011).
Chemical Abstract Compounds, STN express, RN 1100267-42-2 (Entered STN: Feb. 3, 2009).
Chemical Abstract Compounds, STN express, RN 1100240-13-8 (Entered STN: Feb. 3, 2009).
Chemical Abstract Compounds, STN express, RN 931623-21-1 (Entered STN: Apr. 22, 2007).
Chemical Abstract Compounds, STN express, RN 924478-95-5 (Entered STN: Mar. 2, 2007).
Chemical Abstract Compounds, STN express, RN 852688-60-9 (Entered STN: Jun. 22, 2005).
Chemical Abstract Compounds, STN express, RN 851964-70-0 (Entered STN: Jun. 9, 2005).
PubChem CID 56813592 Create Date Mar. 8, 2013.
PubChem CID 8197013 8 Create Date Oct. 20, 2014.
Allan AL, et al. Tumor dormancy and cancer stem cells: implications for the biology and treatment of breast cancer metastasis. Breast Dis. 2006; 26:87-98.
Bora-Singhal et al. YAP 1 Regulates OCT 4 Activity and SOX 2 Expression to Facilitate Self-Renewal and Vascular Mimicry of Stem-Like Cells. Stem Cells. Jun. 2015;33(6):1705-18.
Brugger W, et al. EGFR-TKI resistant non-small cell lung cancer (NSCLC): new developments and implications for future treatment. Lung Cancer. 2012;77(1):2-8.
Demicheli R, et al. Recurrence dynamics does not depend on the recurrence site. Breast Cancer Res. 2008;10(5):R83.
Demicheli R, et al. Recurrence dynamics for non-small-cell lung cancer: effect of surgery on the development of metastases. J Thorac Oncol. 2012;7(4):723-30.
Demko ZP, Sharpless KB. An expedient route to the tetrazole analogues of α-amino acids. Organic letters. Jul. 25, 2002;4(15):2525-7.
Giancotti FG. Mechanisms governing metastatic dormancy and reactivation. Cell. 2013;155(4):750-64.
Gunn SJ, Baker A, Bertram RD, Warriner SL. A novel approach to the solid-phase synthesis of peptides with a tetrazole at the C-terminus. Synlett. Oct. 2007;2007(17):2643-6.
Hashmi et al. Gold catalysis: mild conditions for the synthesis of oxazoles from N-propargylcarboxamides and mechanistic aspects. Organic letters. Nov. 11, 2004;6(23):4391-4.
Kanelis, Voula, Daniela Rotin, and Julie D. Forman-Kay. Solution structure of a Nedd4 WW domain-ENaC peptide complex. Nature Structural & Molecular Biology 8.5 (2001): 407.
Karpavichyus, K. I. et al., "Phenylalanine derivatives containing an acyl residue of the stereoisomeric N-[di (ethylenimino)(thio) phosphoryl]-4-aminocyclohexanecarboxylic acids", Russian Chemical Bulletin, 1978, vol. 27, No. 4, pp. 790-795.
Koren A, et al. Lung cancer stem cells: a biological and clinical perspective. Cell Oncol (Dordr). 2013;36(4):265-75.
Lara PN, Jr., et al. Non-small-cell lung cancer progression after first-line chemotherapy. Curr Treat Options Oncol. 2002;3(1):53-8.
Lau AN, et al. Tumor-propagating cells and Yap/Taz activity contribute to lung tumor progression and metastasis. Embo J. 2014;33(5):468-81.
Lee N, et al. Melanoma stem cells and metastasis: mimicking hematopoietic cell trafficking? Lab Invest. 2014;94(1):13-30.
Leeman KT, et al. Lung stem and progenitor cells in tissue homeostasis and disease. Curr Top Dev Biol. 2014;107:207-33.
Lundin A, et al. Lung cancer stem cells: progress and prospects. Cancer Lett. 2013;338(1):89-93.
Macias, Maria J., et al. Structure of the WW domain of a kinase-associated protein complexed with a proline-rich peptide Nature 382.6592 (1996): 646.
Mao B, et al. SIRT1 regulates YAP2-mediated cell proliferation and chemoresistance in hepatocellular carcinoma. Oncogene 33, 2013 1468-1474. Epub Apr. 2, 2013. doi: 10.1038/onc.2013.88.
Mizuno T, et al. YAP induces malignant mesothelioma cell proliferation by upregulating transcription of cell cycle-promoting genes. Oncogene. 2012;31(49):5117-22.
Morrison BJ, et al. Lung cancer-initiating cells: a novel target for cancer therapy. Target Oncol. 2013;8(3):159-72.
Nozaki S, Muramatsu I. Convenient synthesis of N-protected amino acid amides. Bulletin of the Chemical Society of Japan. Jul. 1988;61(7):2647-8.
Oku et al., Small molecules inhibiting the nuclear localization of YAP/TAZ for chemotherapeutics and chemosensitizers against breast cancers, FEBS Open Bio, vol. 5, 2015, 542-549.
Patel P, et al. Cancer stem cells, tumor dormancy, and metastasis. Front Endocrinol (Lausanne). 2012; 3:125.
Patockiene L et al: Izvestiya Akademii Nauk Sssr, Seriya Khimicheskaya, Institut Organicheskoi Khimii Im. N. D. Zelinskogo Rossiiskoi Akademii, Ru, vol. 6, Jan. 1, 1980 (Jan. 1, 1980), pp. 1426-1428, XP009518806, ISSN: 0002-3353 p. 1427; compounds I, II, III, IV.
Peacock CD, et al. Cancer stem cells and the ontogeny of lung cancer. J Clin Oncol. 2008;26(17):2883-9.
Senthi S, et al. Patterns of disease recurrence after stereotactic ablative radiotherapy for early stage non-small-cell lung cancer: a retrospective analysis. Lancet Oncol. 2012;13(8):802-9.
Seve P, et al. Chemoresistance in non-small cell lung cancer. Curr Med Chern Anticancer Agents. 2005;5(1):73-88.
Siegel R, et al. Cancer statistics, 2013. CA Cancer J Clin. 2013;63(1):11-30.
Singh S, et al. Lung cancer stem cells: Molecular features and therapeutic targets. Mol Aspects Med. 2013, 50-60. Epub Sep. 11, 2013. doi: 10.1016/j.mam.2013.08.003.
Sureshbabu VV, Venkataramanarao R, Naik SA, Chennakrishnareddy G. Synthesis of tetrazole analogues of amino acids using Fmoc chemistry: isolation of amino free tetrazoles and their incorporation into peptides. Tetrahedron Letters. Sep. 24, 2007;48(39):7038-41.
Sutherland KD, et al. Multiple cells-of-origin of mutant K-Ras-induced mouse lung adenocarcinoma. Proc Natl Acad Sci U S A. 2014, 4952-4957. Epub Mar. 4, 2014.
Toyoizumi, et al. Combined therapy with chemotherapeutic agents and herpes simplex virus type IICP34.5 mutant (HSV-1716) in human non-small cell lung cancer. Human Gene Therapy, 1999, 10(18):17 3013.
Verdecia, Mark A., et al. Structural basis for phosphoserine-proline recognition by group IV WW domains. Nature Structural & Molecular Biology 7.8 (2000): 639.
Wang, Jing, et al. Lung cancer stem cells and implications for future therapeutics. Cell biochemistry and biophysics 69.3 (2014): 389-398.
Yu FX, et al. The Hippo pathway: regulators and regulations. Genes Dev. 2013;27(4):355-71.
Zhao B, et al. The Hippo pathway in organ size control, tissue regeneration and stem cell self-renewal. Nat Cell Biol. 2011;13(8):877-83.
Search Report and Written Opinion issued by Intellectual Property Office of Singapore in SG 11201902029X, dated Jul. 29, 2020.
Office Action issued for Indian Application No. 201927015477, dated Nov. 24, 2020.
Official Notification issued by the Eurasian Patent Office for Application No. 201990761, dated Mar. 12, 2020.
The Extended European Search Report issued for Application No. 17851738, dated Feb. 26, 2020.
The First Office Action and Search Report issued for Chinese Application No. 201780063922.9, dated Jul. 20, 2021.
Office Action issued for Colombian Application No. NC2019/0003843, dated Jun. 17, 2021.

(56) References Cited

OTHER PUBLICATIONS

Examination Report No. 1 issued for Australian Application No. 2017326611, dated Feb. 10, 2021.
Communication Pursuant to Article 94(3) EPC issued for European Application No. 17851738.9, dated Feb. 4, 2021.

* cited by examiner

| Structure | ID | % inhibition in vitro binding assay at 1 μM | % inhibition in vitro binding assay at 5 μM | IC$_{50}$ binding assay value (uM) | % Inhibition in luciferase assay at 5 uM | IC$_{50}$ Sox2 luciferase inhibition (uM) | IC$_{50}$ value viability in A549 (KRAS mut, EGFR wt) cells | IC$_{50}$ value viability in H1650 (KRAS wt, EGFR mut) cells | % inhibition Sox2 expression |
|---|---|---|---|---|---|---|---|---|---|
| [Structure with OBn, CO$_2$H, F; C$_{32}$H$_{33}$FN$_2$O$_5$] | SR3-027 | 66.7 | 69.6 | | 74.67 | 3.59 | ND | 39.34 | |
| [Structure with Ot-Bu, CO$_2$Me, OEt; C$_{32}$H$_{44}$N$_2$O$_6$] | SR4-172 | -110.4 | -38.4 | | 25.98 | | | | |
| [Structure with CF$_3$, CO$_2$Me, OEt; C$_{29}$H$_{35}$F$_3$N$_2$O$_5$] | SR4-173 | -1.5 | 14.9 | | 80.68 | | | | |
| [Structure with OMe, CO$_2$Me, OEt; C$_{29}$H$_{38}$N$_2$O$_6$] | SR4-174 | 14.7 | -9.1 | | 11.57 | | | | |
| [Structure with F, CO$_2$Me, OEt; C$_{28}$H$_{35}$FN$_2$O$_5$] | SR4-175 | -6.4 | 44.9 | | 61.46 | | | | |

| Structure | ID | % inhibition in in vitro binding assay at 1 μM | % inhibition in in vitro binding assay at 5 μM | IC$_{50}$ binding assay value (μM) | % Inhibition in luciferase assay at 5 μM | IC$_{50}$ Sox2 luciferase inhibition (μM) | IC$_{50}$ value viability in A549 (KRAS mut, EGFR wt) cells | IC$_{50}$ value viability in H1650 (KRAS wt, EGFR mut) cells | % inhibition Sox2 expression |
|---|---|---|---|---|---|---|---|---|---|
| $C_{28}H_{35}ClN_2O_5$ (4-Cl phenyl, CO$_2$Me, piperidine amide, 4-ethoxyphenyl) | SR4-176 | -1.9 | 42.5 | | 72.71 | | | | |
| $C_{28}H_{35}IN_2O_5$ (4-I phenyl, CO$_2$Me) | SR4-177 | 33.9 | 36.4 | | 66.70 | | | | |
| $C_{29}H_{35}N_3O_5$ (4-CN phenyl, CO$_2$Me) | SR4-179 | 33.9 | 59.0 | | 60.48 | | | | |
| $C_{29}H_{38}N_2O_5$ (4-Me phenyl, CO$_2$Me) | SR4-180 | -19.0 | 58.1 | | 11.24 | | | | |
| $C_{28}H_{34}F_2N_2O_5$ (3,4-diF phenyl, CO$_2$Me) | SR4-181 | 20.5 | 26.8 | | -6.55 | | | | |

CONT.

| Structure | ID | % inhibition in in vitro binding assay at 1 uM | % inhibition in in vitro binding assay at 5 uM | IC$_{50}$ binding assay value (uM) | % Inhibition in luciferase assay at 5 uM | IC$_{50}$ Sox2 luciferase inhibition (uM) | IC$_{50}$ value viability in A549 (KRAS mut, EGFR wt) cells | IC$_{50}$ value viability in H1650 (KRAS wt, EGFR mut) cells | % inhibition Sox2 expression |
|---|---|---|---|---|---|---|---|---|---|
| $C_{28}H_{34}Cl_2N_2O_5$ (3,4-diCl-Ph, CO$_2$Me, 4-OMe-Ph) | SR4-182 | 31.4 | 73.5 | | 59.17 | | | | |
| $C_{31}H_{42}N_2O_6$ (4-Ot-Bu-Ph, CO$_2$H, 4-OMe-Ph) | SR4-183 | -27.7 | 25.8 | | 3.28 | | | | |
| $C_{28}H_{33}N_2O_5$ (4-CF$_3$-Ph, CO$_2$H, 4-OMe-Ph) | SR4-184 | 27.4 | 44.4 | | 26.86 | | | | |
| $C_{28}H_{36}N_2O_6$ (4-OMe-Ph, CO$_2$H, 4-OMe-Ph) | SR5-001 | 29.2 | 55.3 | | 0.66 | | | | |
| $C_{27}H_{33}FN_2O_5$ (4-F-Ph, CO$_2$H, 4-OMe-Ph) | SR5-002 | 12.4 | 49.2 | | 58.08 | | | | |

CONT.

| Structure | ID | % inhibition in vitro binding assay at 1 uM | % inhibition in vitro binding assay at 5 uM | IC$_{50}$ binding assay value (uM) | % inhibition in luciferase assay at 5 uM | IC$_{50}$ Sox2 luciferase inhibition (uM) | IC$_{50}$ value viability in A549 cells (KRAS mut, EGFR wt) | IC$_{50}$ value viability in H1650 cells (KRAS wt, EGFR mut) | % inhibition Sox2 expression |
|---|---|---|---|---|---|---|---|---|---|
| C$_{27}$H$_{33}$ClN$_2$O$_5$ (4-Cl) | SR5-003 | 33.1 | 55.9 | | 77.95 | | | | |
| C$_{27}$H$_{33}$IN$_2$O$_5$ (4-I) | SR5-004 | 40.2 | 61.1 | | 67.03 | | | | |
| C$_{28}$H$_{33}$N$_3$O$_5$ (4-CN) | SR5-005 | 37.6 | 41.7 | | 46.07 | | | | |
| C$_{28}$H$_{36}$N$_2$O$_5$ (4-Me) | SR5-006 | 28.3 | 28.1 | | 23.58 | | | | |
| C$_{27}$H$_{32}$F$_2$N$_2$O$_5$ (3,4-F) | SR5-007 | 50.7 | 49.3 | | 8.52 | | | | |

CONT.

| Structure | ID | % inhibition in vitro binding assay at 1 uM | % inhibition in vitro binding assay at 5 uM | IC$_{50}$ binding assay value (uM) | % Inhibition in luciferase assay at 5 uM | IC$_{50}$ Sox2 luciferase inhibition (uM) | IC$_{50}$ value viability in A549 (KRAS mut, EGFR wt) cells | IC$_{50}$ value viability in H1650 (KRAS wt, EGFR mut) cells | % inhibition Sox2 expression |
|---|---|---|---|---|---|---|---|---|---|
| C$_{27}$H$_{32}$Cl$_2$N$_2$O$_5$ | SR5-008 | 24.1 | 54.1 | | 2.18 | | | | |
| C$_{30}$H$_{39}$FN$_2$O$_5$ | SR5-012 | 68.7 | 61.6 | | 32.81 | | | | |
| C$_{26}$H$_{30}$F$_2$N$_2$O$_4$ | SR5-013 | 64.6 | 49.8 | | 22.79 | | | | |
| C$_{27}$H$_{33}$FN$_2$O$_5$ | SR5-014 | 65.9 | 70.6 | | 26.17 | | | | |
| C$_{27}$H$_{30}$F$_4$N$_2$O$_4$ | SR5-015 | 67.1 | 56.0 | | 11.07 | | | | |

CONT.

| Structure | ID | % inhibition in vitro binding assay at 1 uM | % inhibition in vitro binding assay at 5 uM | IC$_{50}$ binding assay value (uM) | % inhibition in luciferase assay at 5 uM | IC$_{50}$ Sox2 luciferase inhibition (uM) | IC$_{50}$ value viability in A549 (KRAS mut, EGFR wt) cells | IC$_{50}$ value viability in H1650 (KRAS wt, EGFR mut) cells | % inhibition Sox2 expression |
|---|---|---|---|---|---|---|---|---|---|
| 4-Cl aryl; C$_{26}$H$_{30}$ClN$_2$O$_4$ | SR5-016 | 67.3 | 52.9 | | 45.96 | | | | |
| 4-I aryl; C$_{26}$H$_{30}$IN$_2$O$_4$ | SR5-017 | 77.1 | 47.7 | | 73.18 | | | | |
| 4-Me aryl; C$_{27}$H$_{33}$FN$_2$O$_4$ | SR5-018 | 62.3 | 55.3 | | 36.46 | | | | |
| 3,4-diF aryl; C$_{26}$H$_{29}$F$_3$N$_2$O$_4$ | SR5-019 | 54.7 | 64.5 | | 79.95 | | | | |
| 4-CN aryl; C$_{27}$H$_{30}$FN$_3$O$_4$ | SR5-021 | 47.5 | 73.9 | | 28.26 | | | | |

CONT.

| Structure | ID | % inhibition in vitro binding assay at 1 uM | % inhibition in vitro binding assay at 5 uM | IC$_{50}$ binding assay value (uM) | % inhibition in luciferase assay at 5 uM | IC$_{50}$ Sox2 luciferase inhibition (uM) | IC$_{50}$ value viability in A549 (KRAS mut, EGFR wt) cells | IC$_{50}$ value viability in H1650 (KRAS wt, EGFR mut) cells | % inhibition Sox2 expression |
|---|---|---|---|---|---|---|---|---|---|
| C$_{26}$H$_{29}$Cl$_2$FN$_2$O$_4$ | SR5-022 | 43.3 | 50.8 | | 28.65 | | | | |
| C$_{29}$H$_{37}$FN$_2$O$_5$ | SR5-023 | 40.3 | 66.6 | | 16.15 | | | | |
| C$_{25}$H$_{28}$F$_2$N$_2$O$_4$ | SR5-024 | 45.2 | 69.7 | | 10.16 | | | | |
| C$_{26}$H$_{31}$FN$_2$O$_5$ | SR5-025 | 82.2 | 63.3 | | 30.60 | | | | |
| C$_{26}$H$_{28}$F$_4$N$_2$O$_4$ | SR5-026 | 69.8 | 61.0 | | 35.94 | | | | |

CONT.

| Structure | ID | % inhibition in vitro binding assay at 1 μM | % inhibition in vitro binding assay at 5 μM | IC$_{50}$ binding assay value (uM) | % Inhibition in luciferase assay at 5 μM | IC$_{50}$ Sox2 luciferase inhibition (uM) | IC$_{50}$ value viability in A549 (KRAS mut, EGFR wt) cells | IC$_{50}$ value viability in H1650 (KRAS wt, EGFR mut) cells | % inhibition Sox2 expression |
|---|---|---|---|---|---|---|---|---|---|
| C$_{25}$H$_{28}$ClFN$_2$O$_4$ (4-Cl, 3-F) | SR5-027 | 46.0 | 59.2 | | 33.33 | | | | |
| C$_{25}$H$_{28}$FIN$_2$O$_4$ (4-I, 3-F) | SR5-028 | 53.6 | 47.6 | | 76.04 | | | | |
| C$_{26}$H$_{31}$FN$_2$O$_4$ (4-Me, 3-F) | SR5-030 | 61.4 | 64.7 | | 18.75 | | | | |
| C$_{25}$H$_{27}$F$_3$N$_2$O$_4$ (3,4-F, 3-F) | SR5-031 | 38.4 | 51.4 | | 14.45 | | | | |
| C$_{26}$H$_{28}$FN$_3$O$_4$ (4-CN, 3-F) | SR5-032 | 44.1 | 45.8 | | 12.37 | | | | |

CONT.

| Structure | ID | % inhibition in vitro binding assay at 1 μM | % inhibition in vitro binding assay at 5 μM | IC$_{50}$ binding assay value (μM) | % Inhibition in luciferase assay at 5 μM | IC$_{50}$ Sox2 luciferase inhibition (μM) | IC$_{50}$ value viability in A549 (KRAS mut, EGFR wt) cells | IC$_{50}$ value viability in H1650 (KRAS wt, EGFR mut) cells | % inhibition Sox2 expression |
|---|---|---|---|---|---|---|---|---|---|
| C$_{25}$H$_{27}$Cl$_2$FN$_2$O$_4$ | SR5-033 | 37.5 | 52.3 | | 23.83 | | | | |
| C$_{34}$H$_{42}$N$_2$O$_5$ | SR5-038 | 70.0 | 83.3 | 0.54 | | 3.36 | 12.52 | 28.2 | |
| C$_{32}$H$_{37}$FN$_2$O$_4$ | SR5-039 | 43.0 | 93.9 | 0.33 | | 2.31 | 24.21 | 11.8 | |
| C$_{31}$H$_{38}$N$_4$O$_5$ | SR5-052 | -28.8 | 40.3 | | | | | | |
| C$_{30}$H$_{35}$FN$_4$O$_4$ | SR5-060 | -3.2 | -2.6 | | | | | | |

CONT.

| Structure | ID | % inhibition in vitro binding assay at 1 uM | % inhibition in vitro binding assay at 5 uM | IC$_{50}$ binding assay value (uM) | % inhibition in luciferase assay at 5 uM | IC$_{50}$ Sox2 luciferase inhibition (uM) | IC$_{50}$ value viability in A549 (KRAS mut, EGFR wt) cells | IC$_{50}$ value viability in H1650 (KRAS wt, EGFR mut) cells | % inhibition Sox2 expression |
|---|---|---|---|---|---|---|---|---|---|
| OBn, CO$_2$Me, pyridine-piperidine; C$_{32}$H$_{37}$N$_3$O$_5$ | SR5-064 | -8.6 | 32.4 | | | | | | |
| OBn, CO$_2$Me, pyridine-piperidine; C$_{32}$H$_{37}$N$_3$O$_5$ | SR5-065 | 23.2 | 38.5 | | | | | | |
| OBn, CO$_2$Me, pyridine-piperidine; C$_{32}$H$_{37}$N$_3$O$_5$ | SR5-067 | 37.0 | 53.4 | | | | | | |
| OBn, CO$_2$Me, imidazole-piperidine; C$_{37}$H$_{42}$N$_4$O$_5$ | SR5-068 | 66.1 | 98.4 | 0.31 | | 16.73 | | | |
| OBn, CO$_2$Me, imidazole-piperidine; C$_{37}$H$_{42}$N$_4$O$_5$ | SR5-069 | 69.9 | 94.9 | 0.08 | | 21.24 | | | |

CONT.

| Structure | ID | % inhibition in in vitro binding assay at 1 uM | % inhibition in in vitro binding assay at 5 uM | IC$_{50}$ binding assay value (uM) | % inhibition in luciferase assay at 5 uM | IC$_{50}$ Sox2 luciferase inhibition (uM) | IC$_{50}$ value viability in A549 (KRAS mut, EGFR wt) cells | IC$_{50}$ value viability in H1650 (KRAS wt, EGFR mut) cells | % inhibition Sox2 expression |
|---|---|---|---|---|---|---|---|---|---|
| C$_{31}$H$_{36}$N$_{4}$O$_{5}$ | SR5-070 | -18.3 | 27.0 | | | | | | |
| C$_{38}$H$_{41}$N$_{3}$O$_{5}$ | SR5-076 | 48.3 | 94.5 | | | 13.01 | | | |
| C$_{38}$H$_{41}$N$_{3}$O$_{5}$ | SR5-077 | 61.7 | 94.7 | 0.12 | | 6.17 | | | |
| C$_{38}$H$_{41}$N$_{3}$O$_{5}$ | SR5-078 | 92.2 | 98.0 | 0.06 | | 13.95 | | | |
| C$_{38}$H$_{41}$N$_{3}$O$_{5}$ | SR5-079 | 66.7 | 99.4 | | | 19 | | | |

CONT.

| Structure | ID | % inhibition in vitro binding assay at 1 μM | % inhibition in vitro binding assay at 5 μM | IC$_{50}$ binding assay value (μM) | % Inhibition in luciferase assay at 5 μM | IC$_{50}$ Sox2 luciferase inhibition (μM) | IC$_{50}$ value viability in A549 (KRAS mut, EGFR wt) cells | IC$_{50}$ value viability in H1650 (KRAS wt, EGFR mut) cells | % inhibition Sox2 expression |
|---|---|---|---|---|---|---|---|---|---|
| (structure with OBn, CO$_2$Me, piperidine, pyridine) C$_{31}$H$_{36}$N$_4$O$_5$ | SR5-080 | 34.9 | 46.9 | | | | | | |
| (structure with OBn, CO$_2$Me, piperidine, pyridine) C$_{37}$H$_{40}$N$_4$O$_5$ | SR5-081 | 67.8 | 96.8 | | | >50 | | | |
| (structure with OBn, CO$_2$Me, piperidine, pyridine) C$_{37}$H$_{40}$N$_4$O$_5$ | SR5-082 | 64.3 | 97.7 | | | 32.08 | | | |

CONT.

SEQUENCE LISTING

<160> NUMBER OF SEQ ID NOS: 1

<210> SEQ ID NO 1
<211> LENGTH: 17
<212> TYPE: PRT
<213> ORGANISM: Artificial Sequence
<220> FEATURE:

```
<223> OTHER INFORMATION: Synthetic construct

<400> SEQUENCE: 1

Met Ala Lys Thr Ser Ser Gly Gln Arg Tyr Phe Leu Asn His Ile Asp
1               5                   10                  15

Gln
```

YAP1 INHIBITORS THAT TARGET THE INTERACTION OF YAP1 WITH OCT4

CROSS REFERENCE TO RELATED APPLICATIONS

This application is a United States National Phase Patent Application of International Patent Application Number PCT/US2019/022337, filed on Mar. 14, 2019, which claims the benefit of priority to U.S. Provisional Application No. 62/643,032, filed Mar. 14, 2018, which is incorporated by reference herein in its entirety.

BACKGROUND

Lung cancer is the leading cause of cancer related mortality in the United States (Siegel R, et al. Cancer statistics, 2013. *CA Cancer J Clin.* 2013; 63(1):11-30), with majority of this (85%) resulting from non-small cell lung cancer (NSCLC). Patients with early stage disease are treated by surgery, but about 30-60% will develop recurrent tumors, which result in mortality (Demicheli R, et al. Recurrence dynamics does not depend on the recurrence site. *Breast Cancer Res.* 2008; 10(5):R83; Demicheli R, et al. Recurrence dynamics for non-small-cell lung cancer: effect of surgery on the development of metastases. *J Thorac Oncol.* 2012; 7(4):723-30; Senthi S, et al. Patterns of disease recurrence after stereotactic ablative radiotherapy for early stage non-small-cell lung cancer: aAp retrospective analysis. *Lancet Oncol.* 2012; 13(8):802-9). Although chemotherapeutic agents like gemcitabine, platinum compounds and taxanes improve survival to a limited extent, overall survival rates remain low due to recurrence of more aggressive, drug resistant tumors (Seve P, et al. Chemoresistance in non-small cell lung cancer. *Curr Med Chem Anticancer Agents.* 2005; 5(1):73-88; Lara P N, Jr., et al. Non-small-cell lung cancer progression after first-line chemotherapy. *Curr Treat Options Oncol.* 2002; 3(1):53-8). Even patients harboring EGFR mutations who respond well to EGFR inhibitors like Erlotinib eventually develop resistance and succumb to the disease (Brugger W, et al. EGFR-TKI resistant non-small cell lung cancer (NSCLC): new developments and implications for future treatment. *Lung Cancer.* 2012; 77(1):2-8). It has been hypothesized that tumor initiating cells or cancer stem-like cells might contribute to the initiation, progression, metastasis and recurrence of tumors (Patel P, et al. Cancer stem cells, tumor dormancy, and metastasis. *Front Endocrinol* (Lausanne). 2012; 3:125; Allan A L, et al. Tumor dormancy and cancer stem cells: implications for the biology and treatment of breast cancer metastasis. *Breast Dis.* 2006; 26:87-98; Giancotti F G. Mechanisms governing metastatic dormancy and reactivation. *Cell.* 2013; 155(4): 750-64; Lee N, et al. Melanoma stem cells and metastasis: mimicking hematopoietic cell trafficking? *Lab Invest.* 2014; 94(1):13-30) and this idea is gaining significant traction in the lung cancer arena (Peacock C D, et al. Cancer stem cells and the ontogeny of lung cancer. *J Clin Oncol.* 2008; 26(17):2883-9; Singh S, et al. Lung cancer stem cells: Molecular features and therapeutic targets. *Mol Aspects Med.* 2013. Epub 2013/09/11. doi: 10.1016/j.mam.2013.08.003; Koren A, et al. Lung cancer stem cells: a biological and clinical perspective. *Cell Oncol (Dordr).* 2013; 36(4):265-75; Lundin A, et al. Lung cancer stem cells: progress and prospects. *Cancer Lett.* 2013; 338(1):89-93; Morrison B J, et al. Lung cancer-initiating cells: a novel target for cancer therapy. *Target Oncol.* 2013; 8(3):159-72; Leeman K T, et al. Lung stem and progenitor cells in tissue homeostasis and disease. *Curr Top Dev Biol.* 2014; 107: 207-33; Sutherland K D, et al. Multiple cells-of-origin of mutant K-Ras-induced mouse lung adenocarcinoma. *Proc Natl Acad Sci USA.* 2014. Epub 2014/03/04; Wang J, et al. Lung Cancer Stem Cells and Implications for Future Therapeutics. *Cell Biochem Biophys.* 2014. Epub 2014/02/20. doi: 10.1007/s12013-014-9844-4; Lau A N, et al. Tumor-propagating cells and Yap/Taz activity contribute to lung tumor progression and metastasis. *Embo J.* 2014; 33(5):468-81). In this context, our studies have shown that the oncogenic component of the Hippo signaling pathway, YAP1, contributes to the self-renewal and vascular mimicry of stem-like cells.

The classic Hippo signaling cascade leads to the activation of the kinases Lats1/2 and Mst1/2, which phosphorylate YAP1 or its orthologue TAZ resulting in their cytoplasmic sequestration and/or degradation (Yu F X, et al. The Hippo pathway: regulators and regulations. *Genes Dev.* 2013; 27(4):355-71; Zhao B, et al. The Hippo pathway in organ size control, tissue regeneration and stem cell self-renewal. *Nat Cell Biol.* 2011; 13(8):877-83). Inactivation of the Hippo pathway leads to the activation and nuclear translocation of YAP1, where it associates mainly with TEAD family transcription factors, to promote cell proliferation (Mizuno T, et al. YAP induces malignant mesothelioma cell proliferation by upregulating transcription of cell cycle-promoting genes. *Oncogene.* 2012; 31(49):5117-22; Mao B, et al. SIRT1 regulates YAP2-mediated cell proliferation and chemoresistance in hepatocellular carcinoma. *Oncogene.* 2013. Epub 2013/04/02. doi: 10.1038/onc.2013.88). YAP1 levels are elevated in multiple tumor types, and YAP1 has been found to contribute to the genesis and progression of multiple cancers including those of the pancreas and lung. YAP1 can physically interact with additional transcription factors to promote cell proliferation, angiogenesis and cancer metastasis. In this context, our studies had shown that YAP1 physically interacts with the Oct4 transcription factor to induce another embryonic stem cell transcription factor, Sox2. This interaction occurred through the WW domain of YAP1 and the PPxY motif of Oct4. We had found that disruption of the Oct4-YAP1 interaction could prevent the self-renewal of stem-like side-population cells from lung cancer cell lines, and could prevent vascular mimicry. What are thus needed are compositions and methods that disrupt the Oct4-YAP1 interaction, which will have anti-cancer effects, since such agents would prevent self-renewal, cell proliferation and potentially angiogenesis. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to cancer therapy and to anti-cancer compounds. More specifically, the subject matter disclosed herein relates to inhibitors of YAP1.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying FIGURES, which are incorporated in and constitute a part of this specification, illustrate several aspects described below.

FIG. 1 is a table of compounds as described herein.

DETAILED DESCRIPTION

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, delaying spread (e.g., metastasis) of the cancer, delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A''$ is used herein as merely a generic substituent in the definitions below.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as ($A^1A^2$)C=C($A^3A^4$) are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O⁻.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "cyano" as used herein is represented by the formula —CN

The term "azido" as used herein is repressed by the formula —$N_3$.

The term "sulfonyl" is used herein to refer to the sulfo-oxo group represented by the formula $S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid).

When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples and Figures.

Compounds

Disclosed herein are compounds of Formula I.

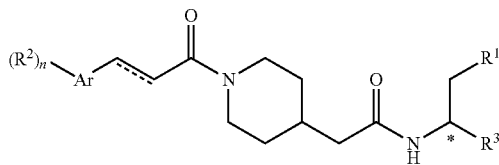

Formula I wherein, the dash line is a bond or is absent;

n is 0, 1, or 2;

Ar is phenyl, pyridinyl, pyrimidinyl, or pyrazinyl;

$R^1$ is $C_1$-$C_8$ alkyl, $C_3$-$C_6$ cycloalkyl, or $C_6$ aryl, and of which is optionally substituted with one or more groups chosen from halo, hydroxyl, cyano, $C_1$-$C_6$ alkyl, $C_1$-$C_6$ haloalkyl, $C_1$-$C_6$ alkoxyl, $C_1$-$C_6$ haloalkoxyl, $C_3$-$C_6$ cycloalkyl, $C_3$-$C_6$ heterocycloalkyl, $C_6$ aryl, heteroaryl, OCH$_2$—$C_6$ aryl, or O—CH$_2$-heteroaryl;

$R^2$ is halo, OH, $C_1$-$C_8$ alkyl, $C_1$-$C_8$ alkoxyl, $C_6$ aryl, O—$C_6$ aryl, heteroaryl, O-heteroaryl, O—CH$_2$—$C_6$ aryl, or O—CH$_2$-heteroaryl; and $R^3$ is CH$_2$OH, CO$_2$H, CO$_2$—$C_1$-$C_6$ alkyl, CO$_2$—$C_1$-$C_6$ heteroalkyl, CO$_2$—$C_3$-$C_6$ cycloalkyl, or CO$_2$—$C_1$-$C_6$ heteroalkyl or a pharmaceutically acceptable salt thereof.

In some examples, the stereochemistry at C* is R. In other examples the stereochemistry at C* is S.

In a preferred example the dashed line is absent.

In some examples, $R^1$ is chosen from $C_1$-$C_8$ alkyl, for example, methyl, ethyl, n-propyl, isopropyl, n-butyl, sec-butyl, tert-butyl, pentyl, hexyl, septyl, and octyl. Any of these can be optionally substituted with one or more groups chosen from halo, hydroxyl, cyano, $C_1$-$C_6$ alkyl, $C_1$-$C_6$ haloalkyl, $C_1$-$C_6$ alkoxyl, $C_1$-$C_6$ haloalkoxyl, $C_3$-$C_6$ cycloalkyl, $C_3$-$C_6$ heterocycloalkyl, $C_6$ aryl, heteroaryl, OCH$_2$—$C_6$ aryl, and O—CH$_2$-heteroaryl.

In some examples, $R^1$ is chosen from $C_3$-$C_6$ cycloalkyl, for example, cyclopropyl, cyclobutyl, cyclopentyl, cyclohexyl, cycloheptyl, and cyclooxytyl. Any of these can be optionally substituted with one or more groups chosen from halo, hydroxyl, cyano, $C_1$-$C_6$ alkyl, $C_1$-$C_6$ haloalkyl, $C_1$-$C_6$ alkoxyl, $C_1$-$C_6$ haloalkoxyl, $C_3$-$C_6$ cycloalkyl, $C_3$-$C_6$ heterocycloalkyl, $C_6$ aryl, heteroaryl, OCH$_2$—$C_6$ aryl, and O—CH$_2$-heteroaryl.

In some examples, $R^1$ is chosen from $C_6$ aryl, in particular, phenyl. The phenyl group can be substituted or unsubstituted. In some examples, the phenyl group can be optionally substituted with one or more groups chosen from halo, hydroxyl, cyano, $C_1$-$C_6$ alkyl, $C_1$-$C_6$ haloalkyl, $C_1$-$C_6$ alkoxyl, $C_1$-$C_6$ haloalkoxyl, $C_3$-$C_6$ cycloalkyl, $C_3$-$C_6$ heterocycloalkyl, $C_6$ aryl, heteroaryl, OCH$_2$—$C_6$ aryl, and O—CH$_2$-heteroaryl. In preferred examples, the phenyl group is substituted with one or more benzyl groups (OCH$_2$—$C_6$ aryl). In other examples, the phenyl group is substituted with one or more $C_1$-$C_6$ alkoxyl such a methoxyl, ethoxyl, or tert-butoxy. In other examples, the phenyl group is substituted with one or more halo groups, such as fluro, chloro, or iodo group. In other examples, the phenyl group is substituted with one or more cyano groups. In specific examples, the phenyl group is substituted with one or more $C_1$-$C_6$ haloalkyl, such as a CF$_3$ group. In specific examples, the phenyl group is substituted with one or more $C_1$-$C_6$ haloalkoxyl, such as an OCF$_3$ group. In specific examples, the phenyl group is substituted with one or more heteroaryl groups, such as a pyrazole, pyridinyl, pyrimidinyl, or pyrazinyl.

In some examples, Ar is phenyl. The phenyl group can be substituted or unsubstituted. In some examples, the phenyl group can be optionally substituted with one or two $R^2$ groups chosen from halo, hydroxyl, $C_1$-$C_8$ alkyl, $C_1$-$C_8$ alkoxyl, $C_6$ aryl, O—$C_6$ aryl, heteroaryl, O-heteroaryl, O—CH$_2$—$C_6$ aryl, and O—CH$_2$-heteroaryl. In specific examples, Ar is a phenyl substituted with one or two halo groups, such as a fluor, chlor, or iodo groups. In a preferred example, Ar is phenyl substituted with $R^2$ when $R^2$ is fluoro. In specific examples, Ar is a phenyl substituted with one or two $C_1$-$C_8$ alkoxyl, such as methoxyl, ethoxyl, propoxyl, tert-butoxyl. In specific examples, Ar is a phenyl substituted with one or two heteroaryl groups, such as pyrazole, pyrimidinyl, or pyrazinyl.

In some examples, Ar is pyridinyl. The pyridinyl group can be substituted or unsubstituted. In some examples, the pyridinyl group can be optionally substituted with one or two $R^2$ groups chosen from halo, hydroxyl, $C_1$-$C_8$ alkyl, $C_1$-$C_8$ alkoxyl, $C_6$ aryl, O—$C_6$ aryl, heteroaryl, O-heteroaryl, O—CH$_2$—$C_6$ aryl, and O—CH$_2$-heteroaryl.

In some examples, Ar is pyrimidinyl. The pyrimidinyl group can be substituted or unsubstituted. In some examples, the pyrimidinyl group can be optionally substituted with one or two $R^2$ groups chosen from halo, hydroxyl, $C_1$-$C_8$ alkyl, $C_1$-$C_8$ alkoxyl, $C_6$ aryl, O—$C_6$ aryl, heteroaryl, O-heteroaryl, O—CH$_2$—$C_6$ aryl, and O—CH$_2$-heteroaryl.

In some examples, Ar is pyrazinyl. The pyrazinyl group can be substituted or unsubstituted. In some examples, the pyrazinyl group can be optionally substituted with one or two $R^2$ groups chosen from halo, hydroxyl, $C_1$-$C_8$ alkyl, $C_1$-$C_8$ alkoxyl, $C_6$ aryl, O—$C_6$ aryl, heteroaryl, O-heteroaryl, O—CH$_2$—$C_6$ aryl, and O—CH$_2$-heteroaryl.

In some examples, $R^2$ is not present (i.e., n is 0).

In some examples, $R^3$ is $CH_2OH$, $CO_2H$, $CO_2$—$C_1$-$C_6$ alkyl (e.g., $CO_2Me$, $CO_2Et$, $CO_2Pr$, $CO_2iPr$, $CO_2t$-Bu), $CO_2$—$C_1$-$C_6$ heteroalkyl, $CO_2$—$C_3$-$C_6$ cycloalkyl, or $CO_2$—$C_1$-$C_6$ heteroalkyl. In a preferred example, $R^3$ is $CO_2Me$ or $CO_2H$.

In some embodiments, the compounds can have Formula I-A:

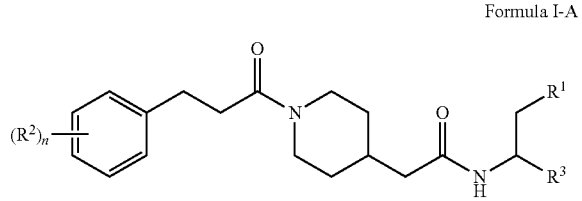

Formula I-A

In some examples, of Formula I-A, $R^3$ is $CO_2H$ or $CO_2Me$.

In some embodiments, the compounds can have Formula I-B

Formula I-B

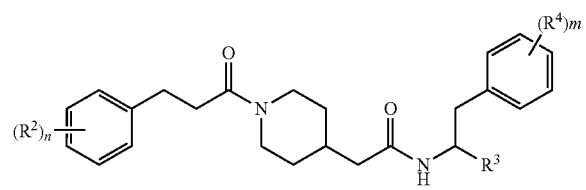

wherein m is 0, 1, or 2;

and $R^4$ is halo, OH, cyano, $C_1$-$C_6$ alkyl, $C_1$-$C_6$ haloalkyl, $C_1$-$C_6$ alkoxyl, $C_1$-$C_6$ haloalkoxyl, $C_3$-$C_6$ cycloalkyl, $C_3$-$C_6$ heterocycloalkyl, $C_6$ aryl, heteroaryl, $OCH_2$—$C_6$ aryl, or O—$CH_2$-heteroaryl.

In some examples, of Formula I-B, $R^3$ is $CO_2H$ or $CO_2Me$. In some examples, m is 1. In other examples, m is 2. In other examples, $R^4$ is halo, such as fluoro, chloro, or iodo. In a preferred example, $R^4$ is benzyl. In other examples, $R^4$ is $C_1$-$C_6$ oalkyl, such a methyl or ethyl. In other examples, $R^4$ is $C_1$-$C_6$ alkoxyl, such as methoxyl, ethoxyl, or OtBu. In other examples, $R^4$ is $C_1$-$C_6$ haloalkyl, such as $CF_3$.

In some embodiments, the compounds can have Formula I-C

Formula I-C

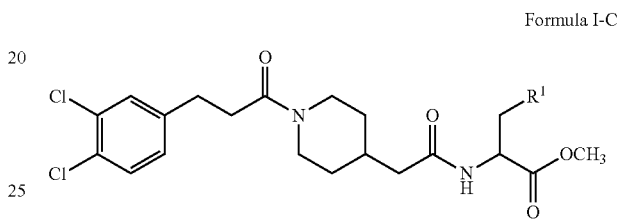

In some examples, the compounds can have Formula I-C, wherein $R^1$ is $C_{1-8}$ alkyl, e.g., methyl, ethyl, —$CH(CH_3)$, propyl, or butyl. In some examples, the compounds can have Formula I-C, wherein $R^1$ is cyclopentyl or cyclohexyl. In some examples, the compounds can have Formula I-C, wherein $R^1$ is aryl substituted with a fluoro group.

In specific examples, the compounds can be chosen from those listed in Table 1.

TABLE 1

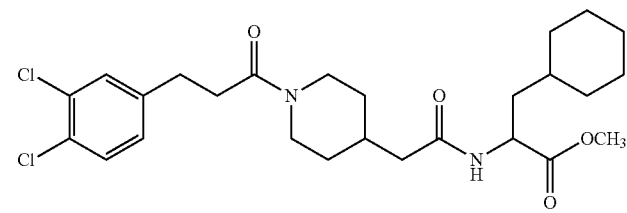 [SMILES: COC(=O)C(CC1CCCCC1)NC(=O)CC1CCN(C(=O)CCc2ccc(Cl)c(Cl)c2)CC1]

SR3-137

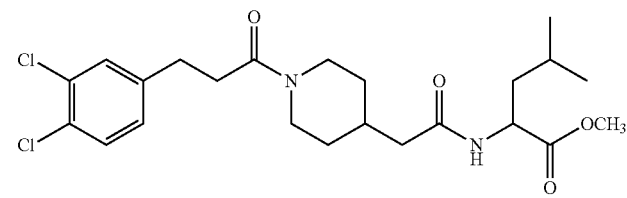 [SMILES: COC(=O)C(CC(C)C)NC(=O)CC1CCN(C(=O)CCc2ccc(Cl)c(Cl)c2)CC1]

SR3-139

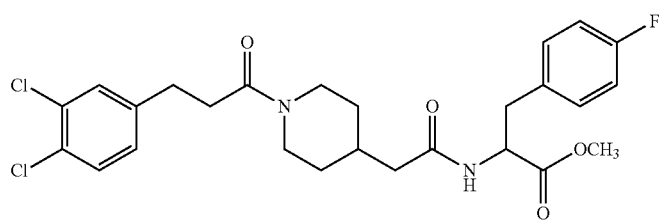 [SMILES: COC(=O)C(Cc1ccc(F)cc1)NC(=O)CC1CCN(C(=O)CCc2ccc(Cl)c(Cl)c2)CC1]

SR3-174

TABLE 1-continued
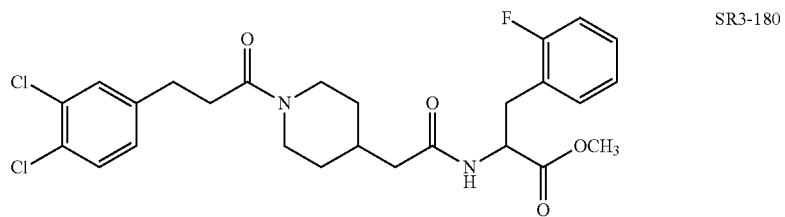 SR3-180
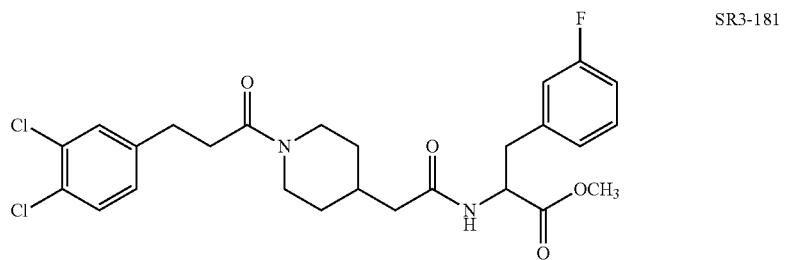 SR3-181
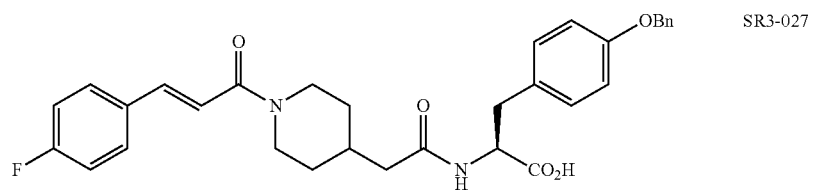 SR3-027
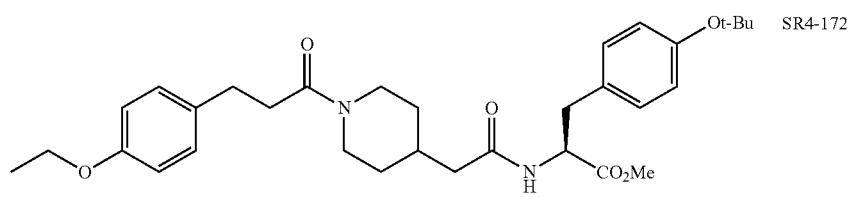 SR4-172
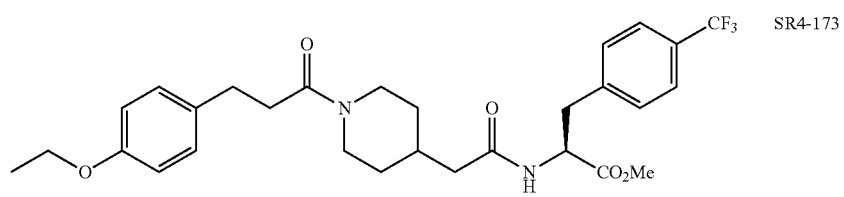 SR4-173
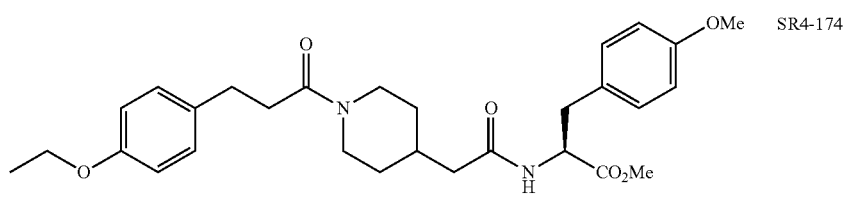 SR4-174
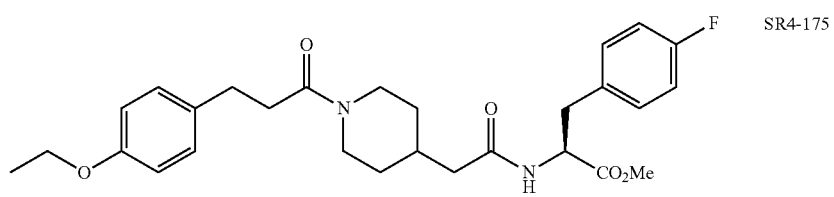 SR4-175

TABLE 1-continued
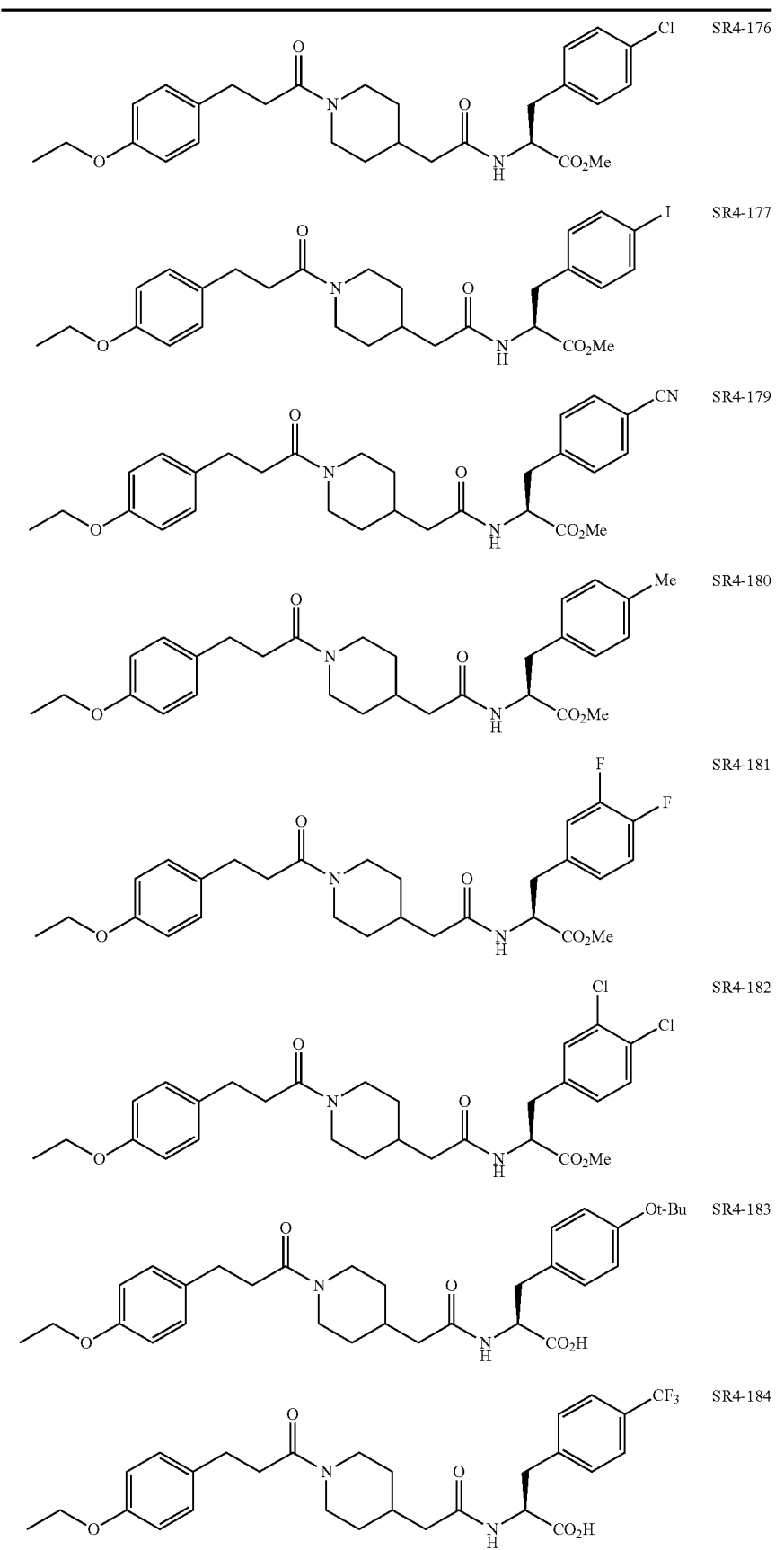

TABLE 1-continued
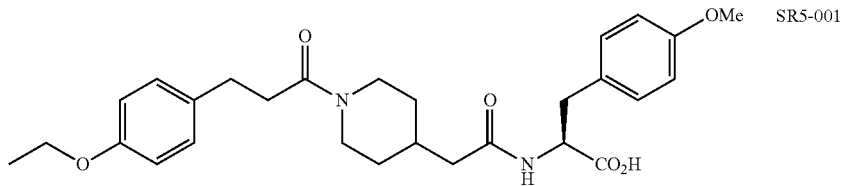 SR5-001
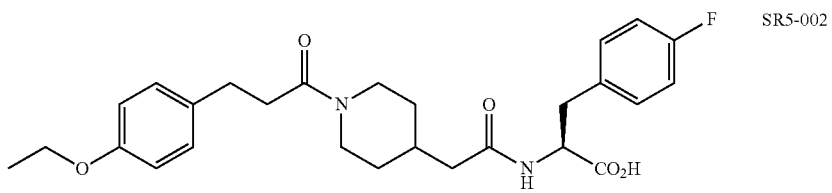 SR5-002
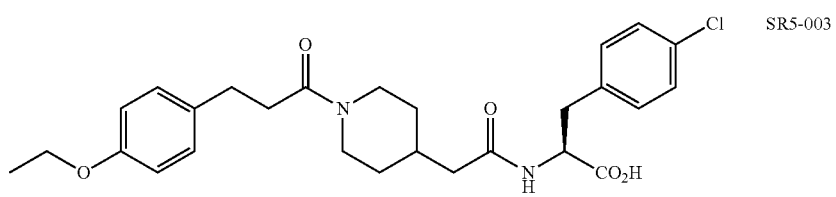 SR5-003
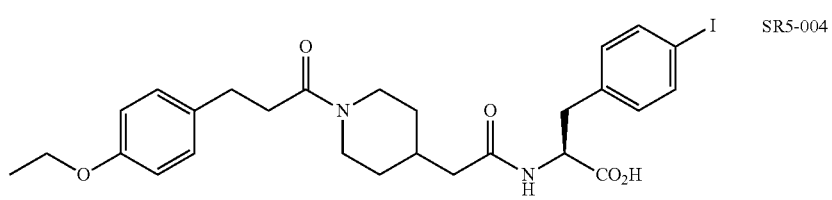 SR5-004
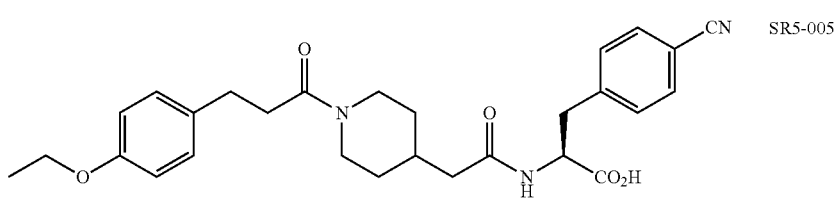 SR5-005
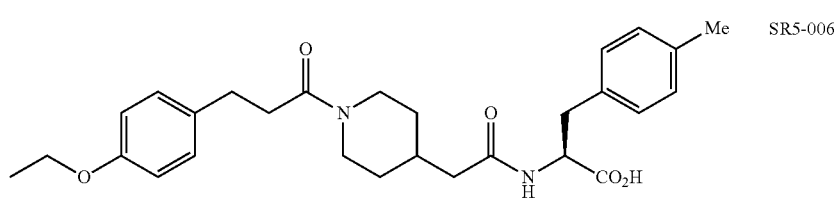 SR5-006
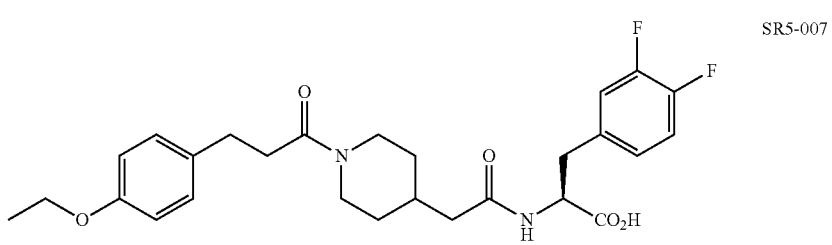 SR5-007

TABLE 1-continued
| | |
|---|---|
| 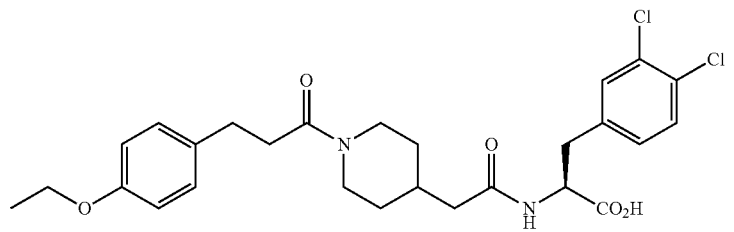 [SMILES: CCOc1ccc(CCC(=O)N2CCC(CC(=O)N[C@@H](Cc3ccc(Cl)c(Cl)c3)C(=O)O)CC2)cc1] | SR5-008 |
| 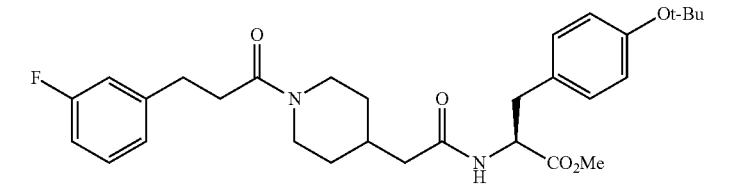 [SMILES: COC(=O)[C@H](Cc1ccc(OC(C)(C)C)cc1)NC(=O)CC1CCN(C(=O)CCc2cccc(F)c2)CC1] | SR5-012 |
| 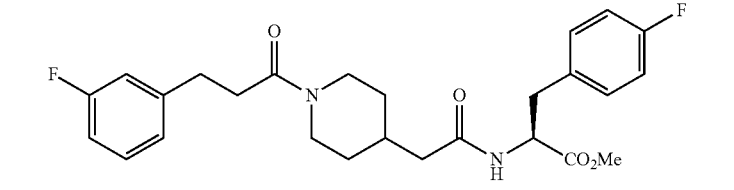 [SMILES: COC(=O)[C@H](Cc1ccc(F)cc1)NC(=O)CC1CCN(C(=O)CCc2cccc(F)c2)CC1] | SR5-013 |
| 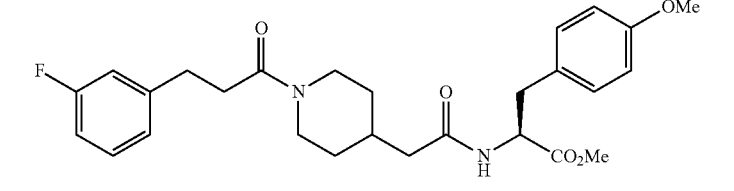 [SMILES: COC(=O)[C@H](Cc1ccc(OC)cc1)NC(=O)CC1CCN(C(=O)CCc2cccc(F)c2)CC1] | SR5-014 |
| 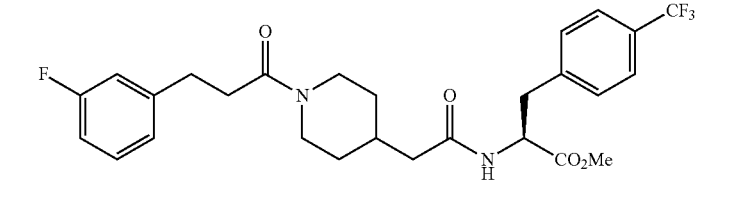 [SMILES: COC(=O)[C@H](Cc1ccc(C(F)(F)F)cc1)NC(=O)CC1CCN(C(=O)CCc2cccc(F)c2)CC1] | SR5-015 |
| 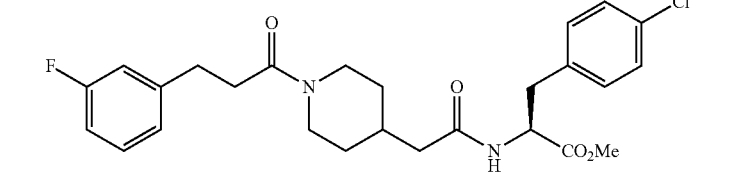 | SR5-016 |
| 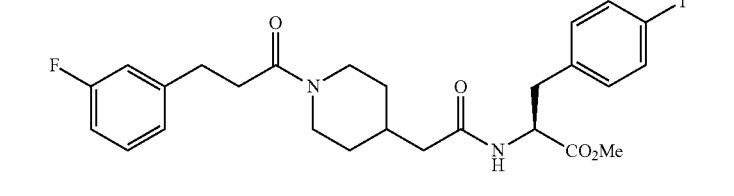 | SR5-017 |
| 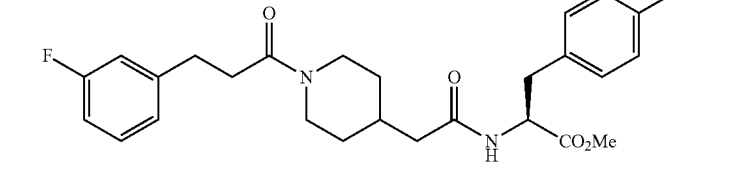 | SR5-018 |

TABLE 1-continued
| | |
|---|---|
| 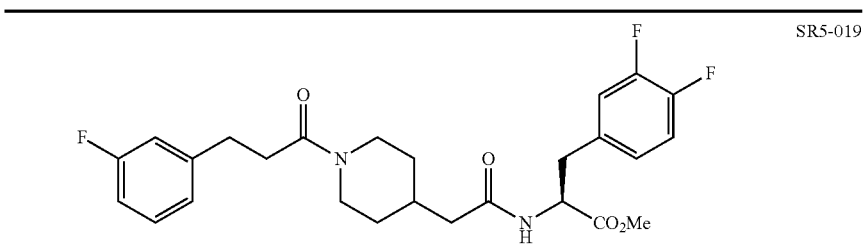 | SR5-019 |
| 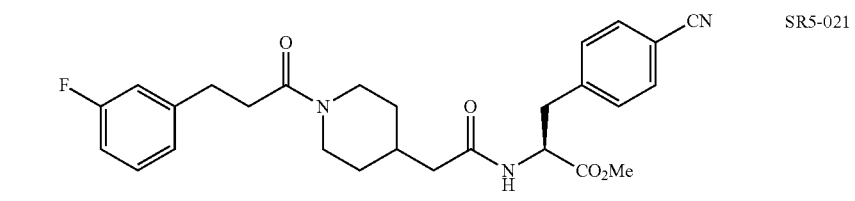 | SR5-021 |
| 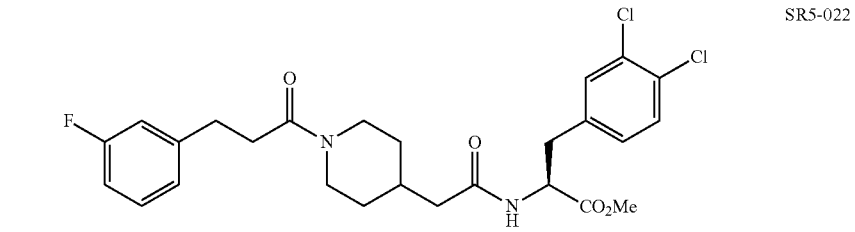 | SR5-022 |
| 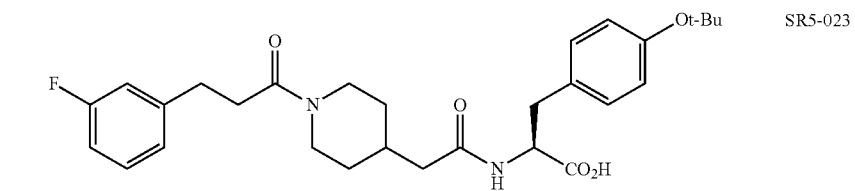 | SR5-023 |
| 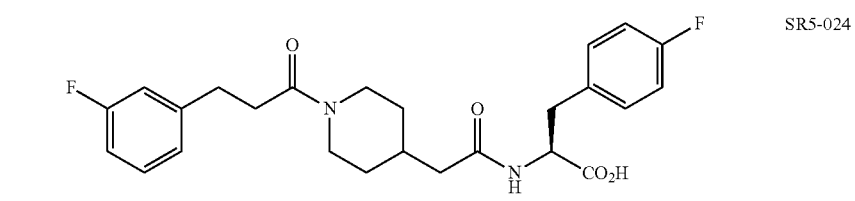 | SR5-024 |
| 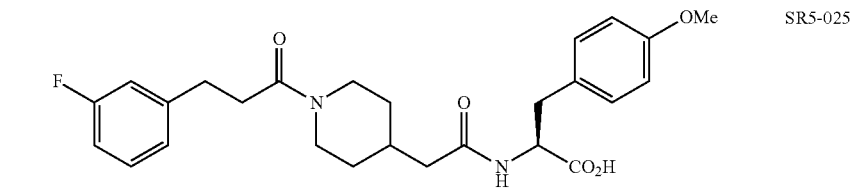 | SR5-025 |
| 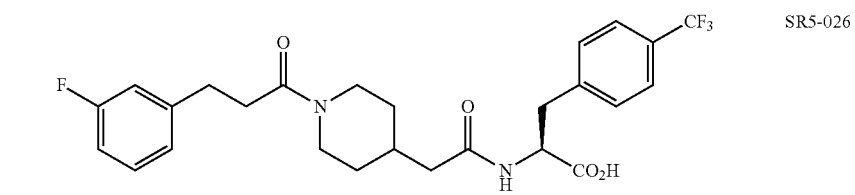 | SR5-026 |
| 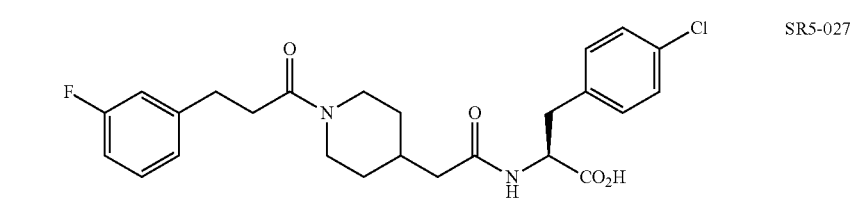 | SR5-027 |

TABLE 1-continued
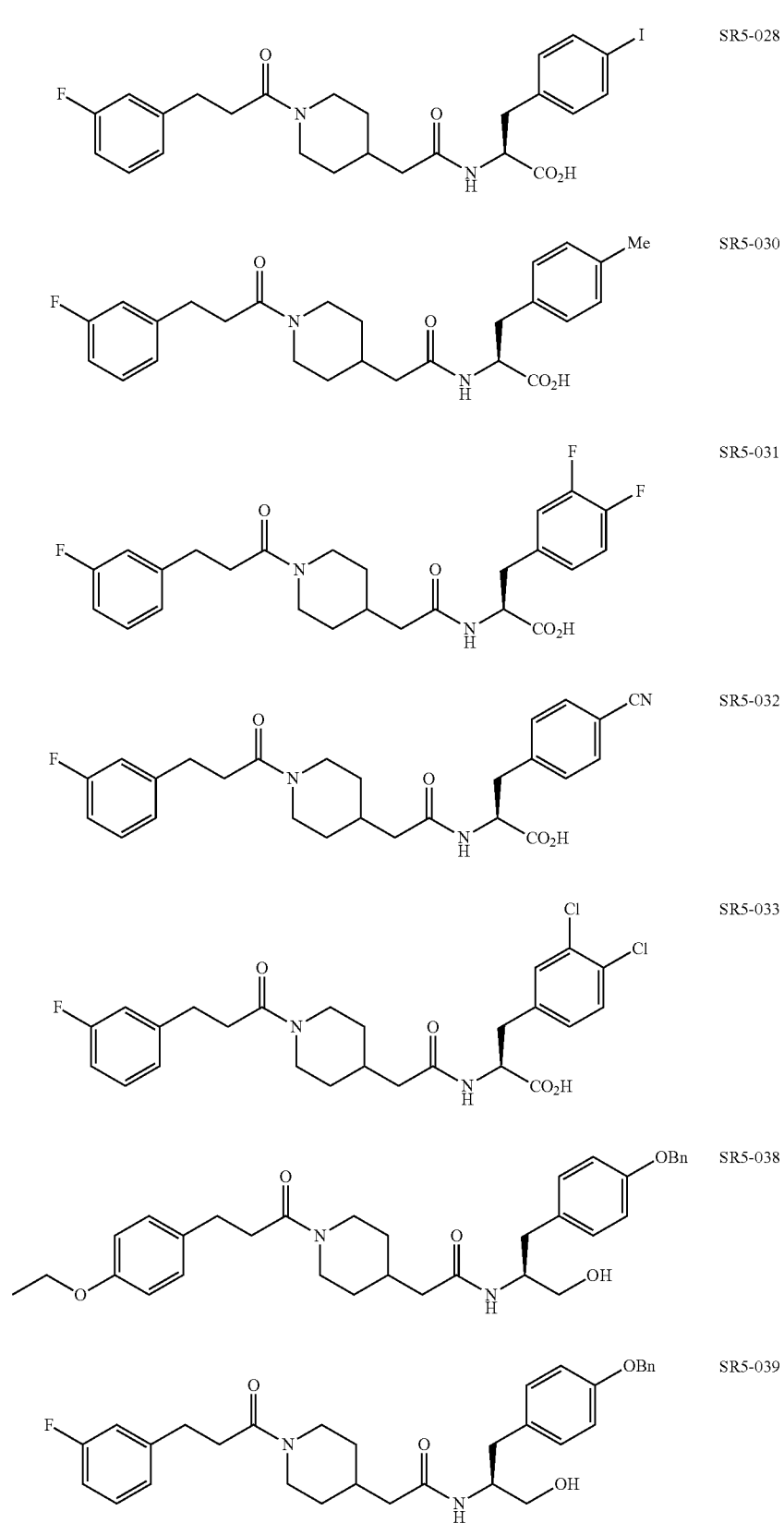

TABLE 1-continued
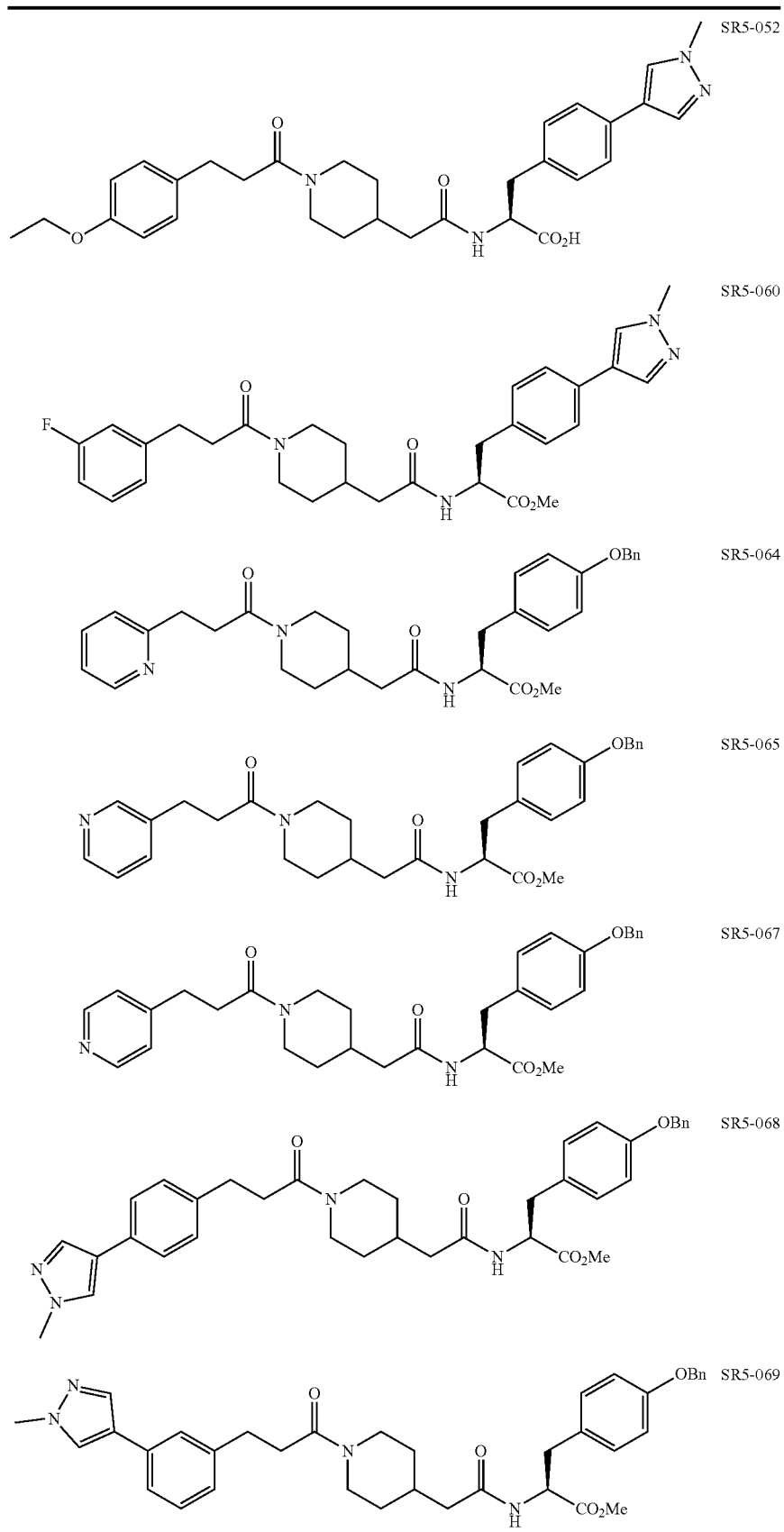

TABLE 1-continued
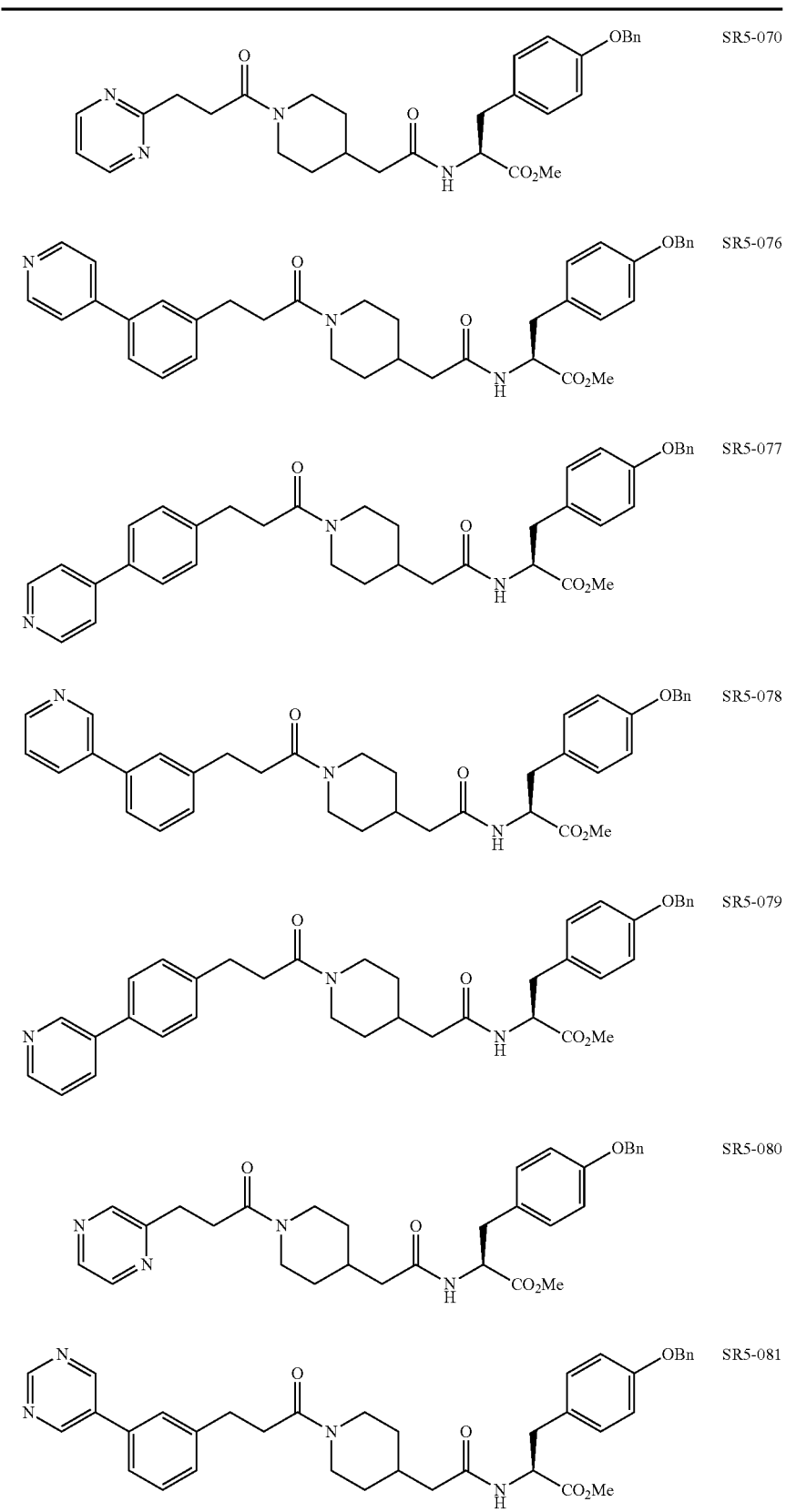

TABLE 1-continued

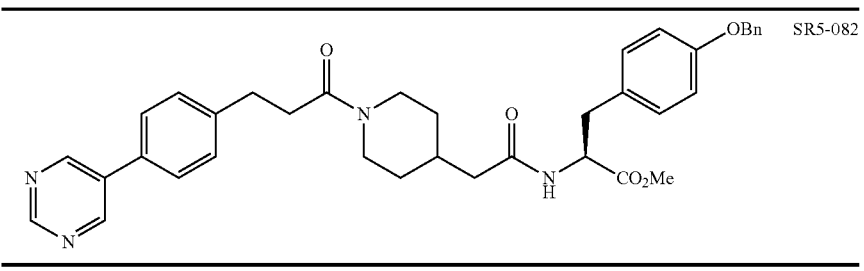

SR5-082

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents.

Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenstram's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

In specific examples, the type of cancer is lung cancer.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publiation No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy*, 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$ $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described herein. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

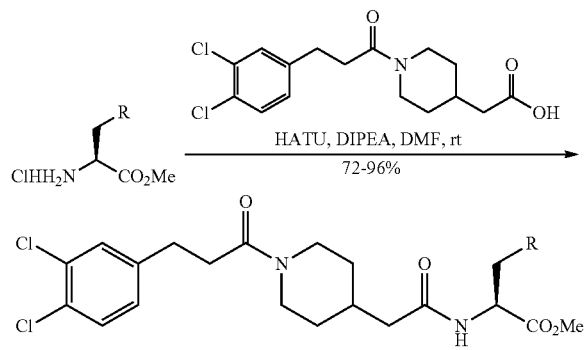

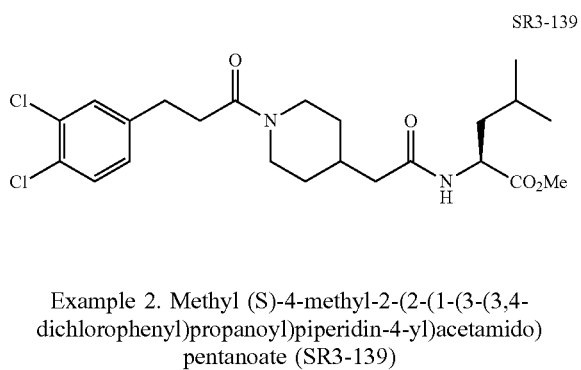

Example 2. Methyl (S)-4-methyl-2-(2-(1-(3-(3,4-dichlorophenyl)propanoyl)piperidin-4-yl)acetamido)pentanoate (SR3-139)

General procedure: The substituted methyl aminopropanoate hydrochloride salt (0.087 mmol, 1.2 eq.) was added to a mixture of DIPEA (diisopropylethylamine) (0.219 mmol, 3.0 eq.), HATU (0.087 mmol, 1.2 eq.), and 2-(1-(3-(3,4-dichlorophenyl)propanoyl)piperidin-4-yl)acetic acid (0.073 mmol, 1.0 eq.) in dry DMF (1.5-2.0 mL) under argon. The mixture was stirred at room temperature for 18-24 h and concentrated under reduced pressure. The resulting thick oil was dissolved in EtOAc (25 mL) and washed with 1N HCl (2×20 mL) and sat. aq. $NaHCO_3$ (2×20 mL). The organic layer was dried ($Na_2SO_4$) and evaporated. Purification by flash column chromatography using MeOH/DCM (0:100-10:90) as eluent afforded the corresponding amidated products.

SR3-139 was obtained as a white foam (0.032 g, 94%) from methyl L-leucinate hydrochloride (0.016 g, 0.087 mmol) using the general method. HPLC: >96% [$t_R$=5.2 min, 70% MeOH, 30% water (with 0.1% TFA), 20 min]. $^1$H NMR (500 MHz, DMSO-$d_6$) δ 8.18 (d, J=7.6 Hz, 1H), 7.54 (d, J=2.1 Hz, 1H), 7.52 (d, J=8.2 Hz, 1H), 7.25 (dd, J=8.2, 2.1 Hz, 1H), 4.40-4.18 (m, 2H), 3.84 (m, 1H), 3.61 (s, 3H), 3.02-2.88 (m, 1H), 2.88-2.73 (m, 2H), 2.68-2.58 (m, 2H), 2.56 (m, 1H), 2.05 (d, J=7.3 Hz, 2H), 1.96-1.80 (m, 1H), 1.69-1.50 (m, 4H), 1.51-1.38 (m, 1H), 1.09-0.92 (m, 2H), 0.89 (d, J=6.6 Hz, 3H), 0.84 (d, J=6.5 Hz, 3H).). HRMS (ESI+): m/z calcd for $C_{23}H_{33}Cl_2N_2O_4$ (M+H)$^+$ 471.1812, found 471.1826; m/z calcd for $C_{23}H_{32}Cl_2N_2O_4Na$ (M+Na)$^+$ 493.1631, found 493.1646; HPLC-MS (ESI+): m/z 471.3 [80%, (M+H)$^+$], m/z 493.2 [100%, (M+Na)$^+$].

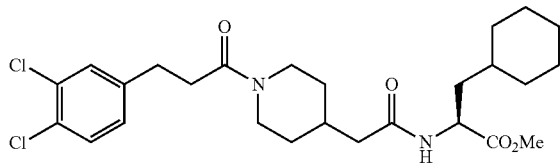

Example 1. Methyl (S)-3-cyclohexyl-2-(2-(1-(3,4-dichlorophenyl)propanoyl)piperidin-4-yl)acetamido)propanoate (SR3-137)

SR3-137 was obtained as a white foam (0.036 g, 95%) from methyl (S)-2-amino-3-cyclohexylpropanoate hydrochloride (0.019 g, 0.087 mmol) using the general method.

HPLC: >98% [$t_R$=5.0 min, 75% MeOH, 25% water (with 0.1% TFA), 20 min]. $^1$H NMR (500 MHz, DMSO-$d_6$) δ 8.18 (d, J=7.9 Hz, 1H), 7.54 (bs, 1H), 7.52 (d, J=8.2 Hz, 1H), 7.25 (dd, J=8.3, 2.1 Hz, 1H), 4.37-4.27 (m, 2H), 3.89-3.77 (m, 1H), 3.63-3.57 (m, 3H), 3.03-2.83 (m, 2H), 2.81 (t, J=7.6 Hz, 2H), 2.68-2.57 (m, 2H), 2.05 (d, J=7.1 Hz, 2H), 1.94-1.82 (m, 1H), 1.72-1.56 (m, 8H), 1.55-1.44 (m, 2H), 1.39-1.22 (m, 2H), 1.22-1.05 (m, 3H), 1.04-0.76 (m, 4H). HRMS (ESI+): m/z calcd for $C_{26}H_{37}Cl_2N_2O_4$ (M+H)$^+$ 511.2125, found 511.2142; m/z calcd for $C_{26}H_{36}Cl_2N_2O_4Na$ (M+Na)$^+$ 533.1944, found 533.1951; HPLC-MS (ESI+): m/z 533.2 [100%, (M+Na)$^+$].

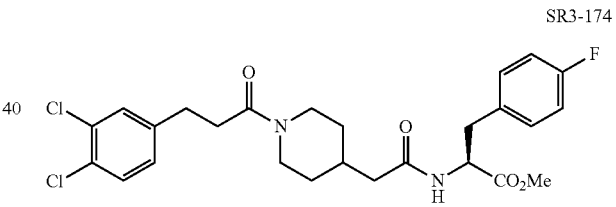

Example 3. Methyl (S)-2-(2-(1-(3-(3,4-dichlorophenyl)propanoyl)piperidin-4-yl)acetamido)-3-(4-fluorophenyl)propanoate (SR3-174)

SR3-174 was obtained as a white foam (0.034 g, 89%) from methyl (S)-2-amino-3-(4-fluorophenyl)propanoate hydrochloride (0.021 g, 0.087 mmol) using general method. HPLC: >99% [$t_R$=5.1 min, 70% MeOH, 30% water (with 0.1% TFA), 20 min]. $^1$H NMR (500 MHz, DMSO-$d_6$) δ 8.27 (d, J=8.0 Hz, 1H), 7.53 (bs, 1H), 7.51 (m, 1H), 7.25 (m, 2H), 7.10 (dd, J=8.8, 1.8 Hz, 2H), 4.50 (m, 1H), 4.26 (m, 1H), 3.76 (m, 1H), 3.61 (s, 3H), 3.04 (dd, J=13.8, 5.2 Hz, 1H), 2.91-2.75 (m, 4H), 2.61 (m, 2H), 2.48-2.36 (m, 1H), 1.97 (d, J=7.2 Hz, 2H), 1.75 (m, 1H), 1.48 (m, 1H), 1.35 (m, 1H), 0.99-0.70 (m, 2H). HRMS (ESI+): m/z calcd for $C_{26}H_{30}Cl_2FN_2O_4$ (M+H)$^+$ 523.1561, found 523.1584; m/z calcd for $C_{26}H_{29}Cl_2FN_2O_4Na$ (M+Na)$^+$ 545.1381, found 545.1493; HPLC-MS (ESI+): m/z 545.2 [100%, (M+Na)$^+$].

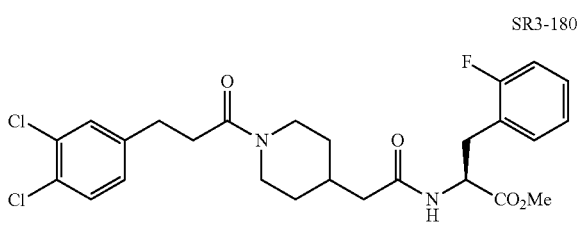 [SMILES: COC(=O)[C@H](Cc1ccccc1F)NC(=O)CC1CCN(C(=O)CCc2ccc(Cl)c(Cl)c2)CC1]

Example 4. Methyl (S)-2-(2-(1-(3-(3,4-dichlorophenyl)propanoyl)piperidin-4-yl)acetamido)-3-(2-fluorophenyl)propanoate (SR3-180)

SR3-180 was obtained as a white foam (0.035 g, 92%) from methyl (S)-2-amino-3-(2-fluorophenyl)propanoate hydrochloride (0.020 g, 0.087 mmol) using general method. HPLC: >98% [$t_R$=5.2 min, 75% MeOH, 25% water (with 0.1% TFA), 20 min]. $^1$H NMR (500 MHz, DMSO-$d_6$) δ 8.32 (d, J=8.1 Hz, 1H), 7.53 (m, 2H), 7.32-7.22 (m, 3H), 7.20-7.07 (m, 2H), 4.55 (m, 1H), 4.26 (m, 1H), 3.83-3.67 (m, 1H), 3.61 (s, 3H), 3.13 (dd, J=13.9, 5.5 Hz, 1H), 2.93-2.74 (m, 4H), 2.67-2.57 (m, 2H), 2.47-2.32 (m, 1H), 1.97 (d, J=7.1 Hz, 2H), 1.81-1.69 (m, 2H), 1.48 (m, 1H), 1.36 (m, 1H), 1.01-0.69 (m, 1H). HRMS (ESI+): m/z calcd for $C_{26}H_{30}Cl_2FN_2O_4$(M+H)$^+$ 523.1561, found 523.1580; m/z calcd for $C_{26}H_{29}Cl_2FN_2O_4$Na (M+Na)$^+$ 545.1381, found 545.1400; HPLC-MS (ESI+): m/z 545.0 [100%, (M+Na$^+$].

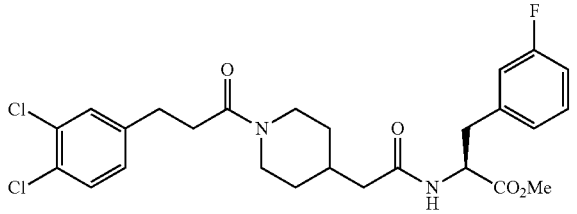 [SMILES: COC(=O)[C@H](Cc1cccc(F)c1)NC(=O)CC1CCN(C(=O)CCc2ccc(Cl)c(Cl)c2)CC1]

Example 5. Methyl (S)-2-(2-(1-(3-(3,4-dichlorophenyl)propanoyl)piperidin-4-yl)acetamido)-3-(3-fluorophenyl)propanoate (SR4-181)

SR3-181 was obtained as a white foam (0.032 g, 84%) from methyl (S)-2-amino-3-(3-fluorophenyl)propanoate hydrochloride (0.020 g, 0.087 mmol) using general method. HPLC: >98% [$t_R$=8.7 min, 70% MeOH, 30% water (with 0.1% TFA), 20 min]. $^1$H NMR (500 MHz, DMSO-$d_6$) δ 8.29 (d, J=8.0 Hz, 1H), 7.56-7.49 (m, 2H), 7.32 (m, 1H), 7.25 (d, J=8.3 Hz, 1H), 7.05 (m, 3H), 4.54 (m, 1H), 4.26 (m, 1H), 3.82-3.70 (m, 1H), 3.62 (s, 3H), 3.09 (dd, J=13.8, 5.0 Hz, 1H), 2.96-2.76 (m, 4H), 2.61 (m, 2H), 2.48-2.35 (m, 1H), 1.97 (d, J=7.2 Hz, 2H), 1.77 (m, 1H), 1.48 (m, 1H), 1.34 (m, 1H), 1.01-0.71 (m, 2H). HRMS (ESI+): m/z calcd for $C_{26}H_{30}Cl_2FN_2O_4$(M+H)$^+$ 523.1561, found 523.1567; m/z calcd for $C_{26}H_{29}Cl_2FN_2O_4$Na (M+Na)$^+$ 545.1381, found 545.1393; HPLC-MS (ESI+): m/z 545.0 [60%, (M+Na$^+$].

General Method 2

N-Boc-protected cyclic carboxylic acid derivative (0.200 g, 0.872 mmol, 1 eq.) in DMF (5 mL) under Ar at rt was added DIPEA (0.457 mL, 2.616 mmol, 3 eq.), HATU (0.365 g, 0.959 mmol, 1.1 eq), and H-Tyr(Bzl)-OMe·HCl (0.309 g, 0.959 mmol, 1.1 eq). The mixture was stirred for 16 h and concentrated. The resulting residue was dissolved in EtOAc and washed with 1N HCl (2×20 mL) and sat. aq. NaHCO$_3$ (2×20 mL). The organic layer was dried (Na$_2$SO$_4$) and evaporated. Purification by flash column chromatography using MeOH/DCM (0:100-10:90) as eluent afforded a white foam (0.410 g, 94%).

General Method 3 for Hydrolysis of Methyl Esters

Methyl ester analog was dissolved in MeOH or THF (1.5 mL) and 1M NaOH or LiOH·H$_2$O (1.5 mL) added into the mixture. The reaction was stirred for 2 h at rt and concentrated under reduced pressure. The resulting slurry was dissolved in water and washed with Et$_2$O (1×20 mL). The aqueous layer was acidified and extracted with EtOAc (2×30 mL). The organic layer was dried and evaporated to afford C-terminal carboxylic acid derivatives.

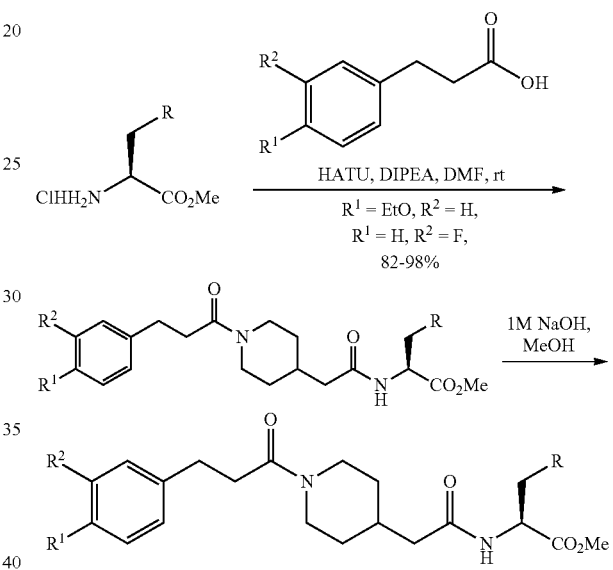

Scheme 1

General Procedure 4 for Coupling Propionic Acid to C-Terminal Amino Methyl Ester Corresponding methyl aminopropanoate hydrochloride salt (0.376 mmol, 1.2 eq.) was added into a mixture of DIPEA (0.939 mmol, 3.0 eq.), HATU (0.376 mmol, 1.2 eq.), and 2-(1-(3-(4-ethoxyphenyl)propanoyl)piperidin-4-yl)acetic acid (0.313 mmol, 1.0 eq.) or 2-(1-(3-(3-fluorophenyl)propanoyl)piperidin-4-yl)acetic acid (0.341 mmol, 1.0 eq.) in dry DMF (1.5-2.0 mL) under argon. The mixture was stirred at room temperature for 18-24 h and concentrated under reduced pressure. The resulting thick oil was dissolved in EtOAc (25 mL) and washed with 1N HCl (2×20 mL) and sat. aq. NaHCO$_3$ (2×20 mL). The organic layer was dried (Na$_2$SO$_4$) and evaporated. Purification by flash column chromatography using MeOH/DCM (0:100-10:90) as eluent afforded the corresponding amide products.

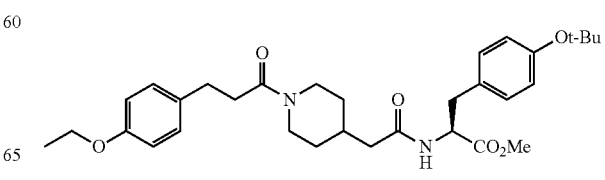

Example 6. Methyl (S)-3-(4-(tert-butoxy)phenyl)-2-(2-(1-(3-(4-ethoxyphenyl)propanoyl)piperidin-4-yl)acetamido)propanoate (SR4-172)

SR4-172 was obtained as a white foam (0.162 g, 94%) from H-Tyr(OtBu)OMe hydrochloride (0.108 g, 0.376 mmol) using general method 4. HPLC: >98% [$t_R$=3.4 min, 70% MeOH, 30% water (with 0.1% TFA), 20 min]. $^1$H NMR (500 MHz, DMSO-$d_6$) δ 8.27 (d, J=7.9 Hz, 1H), 7.16-7.06 (m, 4H), 6.89-6.77 (m, 4H), 4.47 (m, 1H), 4.26 (m, 1H), 3.98 (q, J=6.6 Hz, 2H), 3.79-3.65 (m, 2H), 3.60 (s, 3H), 2.99 (m, 1H), 2.90-2.61 (m, 6H), 2.47-2.34 (m, 1H), 1.98 (d, J=7.6 Hz, 2H), 1.76 (m, 1H), 1.50 (m, 1H), 1.33-1.28 (m, 3H), 1.28-1.20 (m, 9H), 1.01-0.72 (m, 2H). HRMS (ESI+): m/z $C_{32}H_{45}N_2O_6$ (M+H)$^+$553.3264; m/z $C_{32}H_{44}N_2O_6Na$ (M+Na)$^+$ 575.3091; HPLC-MS (ESI+): m/z 553.4 [100% (M+H)$^+$], m/z 570.2 [10%, (M+Na)$^+$].

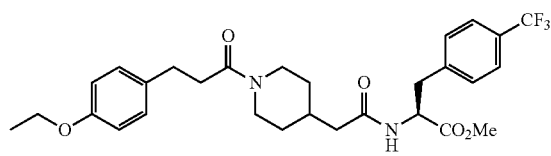 [SMILES: CCOc1ccc(CCC(=O)N2CCC(CC(=O)N[C@@H](Cc3ccc(C(F)(F)F)cc3)C(=O)OC)CC2)cc1]

Example 7. Methyl (S)-2-(2-(1-(3-(4-ethoxyphenyl)propanoyl)piperidin-4-yl)acetamido)-3-(4-(trifluoromethyl)phenyl)propanoate (SR4-173)

SR4-173 was obtained as a white foam (0.158 g, 92%) from H-Phe(4-CF$_3$)—OMe hydrochloride (0.107 g, 0.376 mmol) using general method 4. HPLC: >98% [$t_R$=7.4 min, 70% MeOH, 30% water (with 0.1% TFA), 20 min]. $^1$H NMR (500 MHz, DMSO-$d_6$) δ 8.33 (d, J=8.2 Hz, 1H), 7.65 (d, J=8.0 Hz, 2H), 7.46 (d, J=8.0 Hz, 2H), 7.12 (d, J=8.3 Hz, 2H), 6.81 (dd, J=8.5, 2.2 Hz, 2H), 4.60 (m, 1H), 4.26 (m, 1H), 3.98 (q, J=7.0 Hz, 2H), 3.77-3.65 (m, 1H), 3.64 (s, 3H), 3.18 (dd, J=13.7, 4.9 Hz, 1H), 2.94 (dd, J=13.8, 10.4 Hz, 1H), 2.82 (m, 1H), 2.71 (m, 2H), 2.56-2.51 (m, 2H), 2.46-2.34 (m, 1H), 2.03-1.84 (m, 2H), 1.81-1.62 (m, 1H), 1.44 (m, 1H), 1.30 (t, J=6.9 Hz, 3H), 1.24 (m, 1H), 0.95-0.65 (m, 2H); $^{19}$F NMR (471 MHz, DMSO-$d_6$) δ −60.8 (m). HRMS (ESI+): m/z $C_{29}H_{36}F_3N_2O_5$(M+H)$^+$ 549.2569; m/z $C_{29}H_{35}F_3N_2O_5Na$ (M+Na)$^+$ 571.2400; HPLC-MS (ESI+): m/z 549.2 [100% (M+H)$^+$], m/z 571.2 [10%, (M+Na)$^+$].

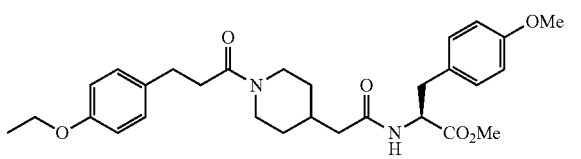 [SMILES: CCOc1ccc(CCC(=O)N2CCC(CC(=O)N[C@@H](Cc3ccc(OC)cc3)C(=O)OC)CC2)cc1]

Example 8. Methyl (S)-2-(2-(1-(3-(4-ethoxyphenyl)propanoyl)piperidin-4-yl)acetamido)-3-(4-methoxyphenyl)propanoate (SR4-174)

SR4-174 was obtained as a white foam (0.140 g, 88%) from H-Tyr(OMe)-OMe hydrochloride (0.093 g, 0.376 mmol) using general method 4. HPLC: >98% [$t_R$=4.7 min, 70% MeOH, 30% water (with 0.1% TFA), 20 min]. $^1$H NMR (500 MHz, DMSO-$d_6$) δ 8.23 (d, J=8.0 Hz, 1H), 7.13 (m, 4H), 6.83 (m, 4H), 4.46 (m, 1H), 4.27 (m, 1H), 3.98 (q, J=6.9 Hz, 2H), 3.72 (s, 2H, rotamer), 3.68 (s, 1H, rotamer), 3.61 (s, 3H), 2.98 (dd, J=13.8, 5.2 Hz, 1H), 2.90-2.63 (m, 5H), 2.55-2.52 (m, 1H), 2.49-2.32 (m, 1H), 1.96 (m, 2H), 1.74 (m, 1H), 1.48 (m, 1H), 1.31 (t, J=6.9 Hz, 3H), 1.30-1.24 (m, 1H), 1.00-0.72 (m, 2H). HRMS (ESI+): m/z $C_{29}H_{39}N_2O_6$ (M+H)$^+$ 511.2794; m/z $C_{29}H_{38}N_2O_6Na$ (M+Na)$^+$533.2619; HPLC-MS (ESI+): m/z 511.2 [100% (M+H)$^+$], m/z 533.2 [40%, (M+Na)$^+$].

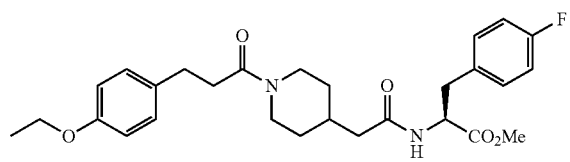 [SMILES: CCOc1ccc(CCC(=O)N2CCC(CC(=O)N[C@@H](Cc3ccc(F)cc3)C(=O)OC)CC2)cc1]

Example 9. Methyl (S)-2-(2-(1-(3-(4-ethoxyphenyl)propanoyl)piperidin-4-yl)acetamido)-3-(4-fluorophenyl)propanoate (SR4-175)

SR4-175 was obtained as a white foam (0.147 g, 94%) from H-Phe(4-F)—OMe hydrochloride (0.088 g, 0.376 mmol) using general method 4. HPLC: >98% [$t_R$=4.9 min, 70% MeOH, 30% water (with 0.1% TFA), 20 min]. $^1$H NMR (500 MHz, DMSO-$d_6$) δ 8.28 (d, J=8.1 Hz, 1H), 7.30-7.21 (m, 2H), 7.21-7.04 (m, 4H), 6.82 (dd, J=8.5, 2.2 Hz, 2H), 4.50 (dd, J=13.2, 5.1 Hz, 1H), 4.27 (m, 1H), 3.98 (q, J=6.9 Hz, 2H), 3.83-3.69 (m, 1H), 3.61 (s, 3H), 3.04 (dd, J=13.8, 5.1 Hz, 1H), 2.91-2.79 (m, 1H), 2.79-2.65 (m, 4H), 2.54 (m, 1H), 2.48-2.35 (m, 1H), 1.96 (d, J=7.2 Hz, 2H), 1.74 (m, 1H), 1.46 (m, 1H), 1.31 (t, J=7.0 Hz, 4H), 1.37-1.29 (m, 1H), 0.98-0.70 (m, 2H); $^{19}$F NMR (471 MHz, DMSO-$d_6$) δ−116.6 (m). HRMS (EST+): m/z $C_{28}H_{36}FN_2O_5$(M+H)$^+$ 499.2599; m/z $C_{28}H_{35}FN_2O_5Na$ (M+Na)$^+$ 521.2417; HPLC-MS (ESI+): m/z 499.2 [100% (M+H)$^+$], m/z 521.2 [40%, (M+Na)$^+$].

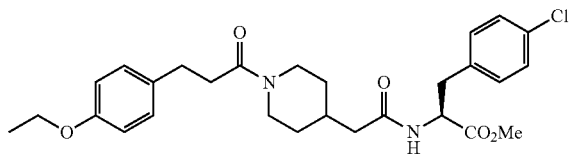 [SMILES: CCOc1ccc(CCC(=O)N2CCC(CC(=O)N[C@@H](Cc3ccc(Cl)cc3)C(=O)OC)CC2)cc1]

Example 10. Methyl (S)-3-(4-chlorophenyl)-2-(2-(1-(3-(4-ethoxyphenyl)propanoyl)piperidin-4-yl)acetamido)propanoate (SR4-176)

SR4-176 was obtained as a white foam (0.146 g, 91%) from H-Phe(4-Cl)—OMe hydrochloride (0.0128 g, 0.376 mmol) using general method 4. HPLC: >98% [$t_R$=10.1 min, 65% MeOH, 35% water (with 0.1% TFA), 20 min]. $^1$H NMR (500 MHz, DMSO-$d_6$) δ 8.28 (dd, J=8.2, 2.3 Hz, 1H), 7.33 (d, J=8.1 Hz, 2H), 7.25 (d, J=8.1 Hz, 2H), 7.17-7.10 (m, 2H), 6.88-6.77 (m, 2H), 4.53 (ddd, J=10.5, 8.1, 5.0 Hz, 1H), 4.28 (m, 1H), 3.98 (q, J=6.9 Hz, 2H), 3.82-3.66 (m, 1H), 3.62 (s, 3H), 3.06 (dd, J=10.9, 5.2 Hz, 1H), 2.84 (m, 2H), 2.76-2.68 (m, 2H), 2.58-2.52 (m, 2H), 2.41 (m, 1H), 2.02-1.88 (m, 2H), 1.45 (m, 1H), 1.31 (t, J=6.9 Hz, 4H), 1.30-1.22 (m, 1H), 1.01-0.67 (m, 2H). HRMS (ESI+): m/z $C_{28}H_{36}C_1N_2O_5$(M+H)$^+$ 515.2316; m/z $C_{28}H_{35}ClN_2O_5Na$ (M+Na)$^+$ 537.2142; HPLC-MS (ESI+): m/z 515.2 [100% (M+H)$^+$], m/z 537.2 [20%, (M+Na)$^+$].

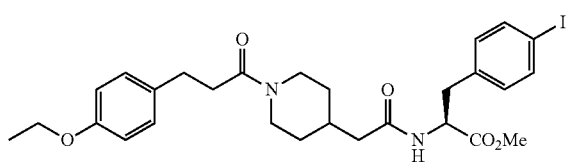 [SMILES: CCOc1ccc(CCC(=O)N2CCC(CC(=O)N[C@@H](Cc3ccc(I)cc3)C(=O)OC)CC2)cc1]

Example 11. Methyl (S)-2-(2-(1-(3-(4-ethoxyphenyl)propanoyl)piperidin-4-yl)acetamido)-3-(4-iodophenyl)propanoate (SR4-177)

SR4-177 was obtained as a white foam (0.169 g, 90%) from H-Phe(4-I)—OMe hydrochloride (0.128 g, 0.376 mmol) using general method 4. HPLC: >98% [$t_R$=5.2 min, 75% MeOH, 25% water (with 0.1% TFA), 20 min]. $^1$H NMR (500 MHz, DMSO-$d_6$) δ 8.32-8.20 (m, 1H), 7.63 (dd, J=8.4, 1.9 Hz, 2H), 7.13 (dd, J=8.4, 4.3 Hz, 2H), 7.04 (d, J=7.9 Hz, 2H), 6.87-6.77 (m, 2H), 4.52 (td, J=9.6, 5.0 Hz, 1H), 4.29 (m, 1H), 3.98 (q, J=7.0 Hz, 2H), 3.80-3.68 (m, 1H), 3.63 (s, 3H), 3.03 (m, 1H), 2.95-2.67 (m, 4H), 2.55 (m, 1H), 2.41 (m, 1H), 1.94 (m, 2H), 1.71 (m, 1H), 1.44 (m, 1H), 1.31 (t, J=7.0 Hz, 3H), 1.22 (m, 1H), 0.95-0.70 (m, 2H). HRMS (ESI+): m/z $C_{28}H_{36}IN_2O_5$(M+H)$^+$ 607.1649; m/z $C_{28}H_{35}IN_2O_5Na$ (M+Na)$^+$ 629.1475; HPLC-MS (ESI+): m/z 607.2 [100% (M+H)$^+$], m/z 629.2 [20%, (M+Na)$^+$].

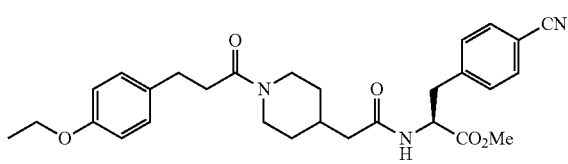

Example 12. Methyl (S)-3-(4-cyanophenyl)-2-(2-(1-(3-(4-ethoxyphenyl)propanoyl)piperidin-4-yl)acetamido)propanoate (SR4-179)

SR4-179 was obtained as a white foam (0.130 g, 82%) from H-Phe(4-CN)—OMe hydrochloride (0.090 g, 0.376 mmol) using general method 4. HPLC: >98% [$t_R$=4.7 min, 65% MeOH, 35% water (with 0.1% TFA), 20 min]. $^1$H NMR (500 MHz, DMSO-$d_6$) δ 8.32 (d, J=8.1 Hz, 1H), 7.83-7.71 (m, 2H), 7.44 (d, J=7.9 Hz, 2H), 7.13 (d, J=7.9 Hz, 2H), 6.81 (d, J=8.3 Hz, 2H), 4.65-4.55 (m, 1H), 4.27 (m, 1H), 3.98 (q, J=6.9 Hz, 2H), 3.81-3.68 (m, 1H), 3.63 (s, 3H), 3.17 (dd, J=13.7, 5.1 Hz, 1H), 2.94 (dd, J=13.8, 10.4 Hz, 1H), 2.89-2.78 (m, 1H), 2.78-2.66 (m, 2H), 2.60-2.53 (m, 2H), 2.48-2.32 (m, 1H), 1.94 (d, J=7.3 Hz, 2H), 1.71 (m, 1H), 1.44 (m, 1H), 1.30 (t, J=6.9 Hz, 3H), 1.33-1.25 (m, 1H), 0.98-0.66 (m, 2H). HRMS (ESI+): m/z $C_{29}H_{36}N_3O_5$ (M+H)$^+$ 506.2646; m/z $C_{29}H_{35}N_3O_5Na$ (M+Na)$^+$ 528.2471; HPLC-MS (ESI+): m/z 506.2 [100% (M+H)$^+$], m/z 528.2 [20%, (M+Na)$^+$].

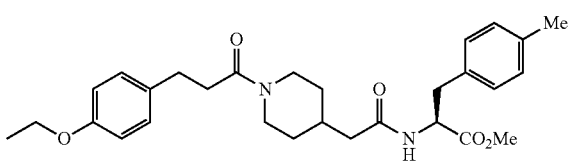 [SMILES: CCOc1ccc(CCC(=O)N2CCC(CC(=O)N[C@@H](Cc3ccc(C)cc3)C(=O)OC)CC2)cc1]

Example 13. Methyl (S)-2-(2-(1-(3-(4-ethoxyphenyl)propanoyl)piperidin-4-yl)acetamido)-3-(p-tolyl)propanoate (SR4-180)

SR4-180 was obtained as a white foam (0.146 g, 94%) from H-Phe(4-Me)-OMe hydrochloride (0.086 g, 0.376 mmol) using general method 4. HPLC: >98% [$t_R$=6.8 min, 70% MeOH, 30% water (with 0.1% TFA), 20 min]. $^1$H NMR (500 MHz, DMSO-$d_6$) δ 8.24 (d, J=8.0 Hz, 1H), 7.19-7.02 (m, 6H), 6.82 (dd, J=8.7, 2.7 Hz, 2H), 4.47 (ddd, J=12.9, 9.8, 5.3 Hz, 1H), 4.27 (m, 1H), 3.98 (q, J=7.0 Hz, 2H), 3.79-3.66 (m, 1H), 3.61 (s, 3H), 3.00 (dd, J=13.8, 5.1 Hz, 1H), 2.92-2.61 (m, 6H), 2.48-2.35 (m, 1H), 2.28-2.19 (m, 3H), 1.96 (d, J=7.2 Hz, 2H), 1.73 (m, 1H), 1.47 (m, 1H), 1.31 (t, J=7.0 Hz, 3H), 0.96-0.66 (m, 1H), 1.36-1.25 (m, 2H). HRMS (ESI+): m/z $C_{29}H_{39}N_2O_5$ (M+H)$^+$ 495.2846; m/z $C_{29}H_{38}N_2O_5Na$ (M+Na)$^+$ 517.2671; HPLC-MS (ESI+): m/z 495.2 [100% (M+H)$^+$], m/z 989.4 [60%, (2M+H)$^+$].

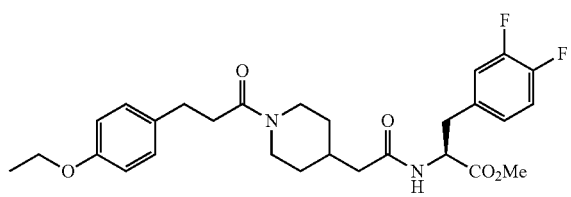 [SMILES: CCOc1ccc(CCC(=O)N2CCC(CC(=O)N[C@@H](Cc3ccc(F)c(F)c3)C(=O)OC)CC2)cc1]

Example 14. Methyl (S)-3-(3,4-difluorophenyl)-2-(2-(1-(3-(4-ethoxyphenyl)propanoyl)piperidin-4-yl)acetamido)propanoate (SR4-181)

SR4-181 was obtained as a white foam (0.153 g, 95%) from H-Phe(3,4-F$_2$)—OMe hydrochloride (0.094 g, 0.376 mmol) using general method 4. HPLC: >98% [$t_R$=9.2 min, 65% MeOH, 35% water (with 0.1% TFA), 20 min]. $^1$H NMR (500 MHz, DMSO-$d_6$) δ 8.28 (d, J=8.0 Hz, 1H), 7.41-7.24 (m, 2H), 7.12 (d, J=8.2 Hz, 2H), 7.07 (d, J=8.7 Hz, 1H), 6.87-6.75 (m, 2H), 4.54 (m, 1H), 4.28 (m, 1H), 3.98 (q, J=7.0 Hz, 2H), 3.83-3.68 (m, 1H), 3.63 (s, 3H), 3.07 (dd, J=13.8, 5.0 Hz, 1H), 2.92-2.76 (m, 2H), 2.77-2.66 (m, 2H), 2.59-2.52 (m, 2H), 2.43 (m, 1H), 2.01-1.90 (m, 2H), 1.81-1.68 (m, 1H), 1.56-1.41 (m, 1H), 1.30 (t, J=7.0 Hz, 4H), 1.37-1.31 (m, 1H), 1.01-0.72 (m, 2H); $^{19}$F NMR (471 MHz, DMSO-$d_6$) δ −139.3--139.5 (m), −141.9--142.2 (m). HRMS (ESI+): m/z $C_{28}H_{35}F_2N_2O_5$(M+H)$^+$ 517.2548; m/z $C_{28}H_{34}F_2N_2O_5Na$ (M+Na)$^+$ 539.2334; HPLC-MS (ESI+): m/z 517.2 [100% (M+H)$^+$], m/z 539.2 [20%, (M+Na)$^+$].

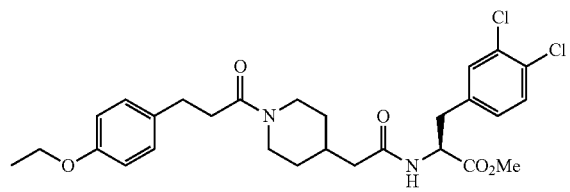 [SMILES: CCOc1ccc(CCC(=O)N2CCC(CC(=O)N[C@@H](Cc3ccc(Cl)c(Cl)c3)C(=O)OC)CC2)cc1]

Example 15. Methyl (S)-3-(3,4-dichlorophenyl)-2-(2-(1-(3-(4-ethoxyphenyl)propanoyl)piperidin-4-yl)acetamido)propanoate (SR4-182)

SR4-182 was obtained as a white foam (0.161 g, 94%) from H-Phe(3,4-Cl$_2$)—OMe hydrochloride (0.107 g, 0.376 mmol) using general method 4. HPLC: >98% [$t_R$=6.4 min, 50% MeOH, 50% water (with 0.1% TFA), 20 min]. $^1$H NMR (500 MHz, DMSO-$d_6$) δ 8.28 (d, J=8.2 Hz, 1H), 7.58-7.47 (m, 2H), 7.28-7.18 (m, 1H), 7.12 (dd, J=8.4, 1.7 Hz, 2H), 6.82 (dd, J=8.7, 2.4 Hz, 2H), 4.65-4.48 (m, 1H), 4.35-4.23 (m, 1H), 3.98 (q, J=6.9 Hz, 2H), 3.81-3.66 (m, 1H), 3.64 (s, 3H), 3.16-3.01 (m, 1H), 2.90-2.76 (m, 2H), 2.76-2.66 (m, 2H), 2.57-2.52 (m, 2H), 2.46-2.34 (m, 1H), 2.02-1.88 (m, 2H), 1.79-1.60 (m, 1H), 1.51-1.40 (m, 1H), 1.31 (t, J=7.0 Hz, 4H), 1.27-1.14 (m, 1H), 0.99-0.70 (m, 2H). HRMS (ESI+): m/z $C_{28}H_{35}Cl_2N_2O_5$ (M+H)$^+$ 549.1908; m/z $C_{28}H_{34}Cl_2N_2O_5Na$ (M+Na)$^+$ 571.1734; HPLC-MS (ESI+): m/z 517.2 [100% (M+H)$^+$], m/z 539.2 [20%, (M+Na)$^+$].

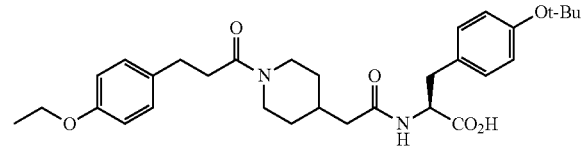 [SMILES: CCOc1ccc(CCC(=O)N2CCC(CC(=O)N[C@@H](Cc3ccc(OC(C)(C)C)cc3)C(=O)O)CC2)cc1]

Example 16. (S)-3-(4-(tert-Butoxy)phenyl)-2-(2-(1-(3-(4-ethoxyphenyl)propanoyl)piperidin-4-yl)acetamido)propanoic acid (SR4-183)

SR4-183 was obtained as a white foam (0.110 g, 89%) from SR4-172 (0.127 g, 0.230 mmol) using general method 3. HPLC: >98% [$t_R$=6.6 min, 70% MeOH, 30% water (with 0.1% formic acid), 20 min]. $^1$H NMR (500 MHz, DMSO-$d_6$) δ 8.12 (dd, J=8.1, 2.3 Hz, 1H), 7.12 (dd, J=8.7, 2.9 Hz, 4H), 6.90-6.73 (m, 4H), 4.49-4.37 (m, 1H), 4.26 (m, 1H), 3.98 (q, J=7.0 Hz, 2H), 3.80-3.59 (m, 1H), 3.03 (m, 1H), 2.93-2.59 (m, 5H), 2.50-2.27 (m, 2H), 1.97 (m, 2H), 1.75 (m, 1H), 1.50 (m, 1H), 1.40-1.33 (m, 1H), 1.31 (t, J=7.0 Hz, 3H), 1.26 (s, 4.5H, rotamer), 1.22 (s, 4.5H, rotamer), 1.03-0.65 (m, 2H). HRMS (ESI+): m/z $C_{31}H_{43}N_2O_6$ (M+H)$^+$ 539.3107; m/z $C_{31}H_{42}N_2O_6Na$ (M+Na)$^+$ 561.2936; HPLC-MS (ESI+): m/z 539.2 [100% (M+H)$^+$], m/z 561.2 [10%, (M+Na)$^+$].

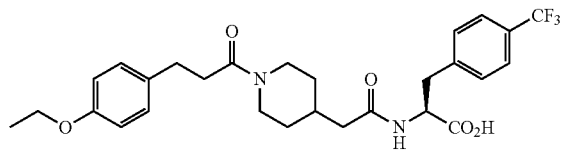 [SMILES: CCOc1ccc(CCC(=O)N2CCC(CC(=O)N[C@@H](Cc3ccc(C(F)(F)F)cc3)C(=O)O)CC2)cc1]

Example 17. (S)-2-(2-(1-(3-(4-Ethoxyphenyl)propanoyl)piperidin-4-yl)acetamido)-3-(4-(trifluoromethyl)phenyl)propanoic acid (SR4-184)

SR4-184 was obtained as a white foam (0.123 g, 93%) from SR4-173 (0.135 g, 0.246 mmol) using general method 3. HPLC: >98% [$t_R$=6.0 min, 70% MeOH, 30% water (with 0.1% formic acid), 20 min]. $^1$H NMR (500 MHz, DMSO-$d_6$) δ 12.81 (s, 1H), 8.18 (d, J=8.5 Hz, 1H), 7.64 (d, J=8.0 Hz, 2H), 7.46 (d, J=8.0 Hz, 2H), 7.16-7.07 (m, 2H), 6.81 (dd, J=8.7, 2.6 Hz, 2H), 4.61-4.49 (m, 1H), 4.31-4.19 (m, 1H), 3.98 (q, J=7.0 Hz, 2H), 3.78-3.59 (m, 1H), 3.19 (dd, J=13.7, 4.6 Hz, 1H), 2.91 (dd, J=13.7, 10.5 Hz, 1H), 2.86-2.63 (m, 4H), 2.48-2.56 (m, 1H), 2.46-2.30 (m, 1H), 1.94 (d, J=7.2 Hz, 2H), 1.77-1.67 (m, 1H), 1.44 (m, 1H), 1.31 (t, J=7.0 Hz, 3H), 1.27-1.17 (m, 1H), 0.94-0.68 (m, 2H); $^{19}$F NMR (471 MHz, DMSO-$d_6$) δ −60.8 (m). HRMS (ESI+): m/z $C_{28}H_{34}F_3N_2O_5$ (M+H)$^+$ 535.2410; m/z $C_{28}H_{33}F_3N_2O_5Na$ (M+Na)$^+$ 557.2234; HPLC-MS (ESI+): m/z 535.2 [100% (M+H)$^+$], m/z 557.2 [50%, (M+Na)$^+$].

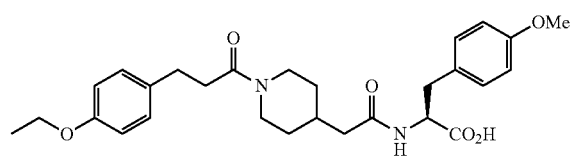 [SMILES: CCOc1ccc(CCC(=O)N2CCC(CC(=O)N[C@@H](Cc3ccc(OC)cc3)C(=O)O)CC2)cc1]

Example 18. (S)-2-(2-(1-(3-(4-Ethoxyphenyl)propanoyl)piperidin-4-yl)acetamido)-3-(4-methoxyphenyl)propanoic acid (SR5-001)

SR5-001 was obtained as a white foam (0.101 g, 90%) from SR4-174 (0.227 g, 0.246 mmol) using general method 3. HPLC: >98% [$t_R$=3.7 min, 70% MeOH, 30% water (with 0.1% formic acid), 20 min]. $^1$H NMR (500 MHz, DMSO-$d_6$) δ 8.07 (d, J=8.3 Hz, 1H), 7.19-7.07 (m, 4H), 6.86-6.77 (m, 4H), 4.47-4.34 (m, 1H), 4.33-4.19 (m, 1H), 3.97 (q, J=6.9, 2H), 3.71 (s, 2H, rotamer), 3.67 (s, 1H, rotamer), 3.00 (dd, J=13.8, 4.6 Hz, 1H), 2.90-2.77 (m, 1H), 2.77-2.63 (m, 3H), 2.55-2.51 (m, 2H), 2.44-2.33 (m, 1H), 2.00-1.92 (m, 2H), 1.77-1.68 (m, 1H), 1.53-1.41 (m, 1H), 1.30 (t, J=7.0 Hz, 3H), 1.24 (m, 1H), 0.95-0.70 (m, 2H). HRMS (ESI+): m/z $C_{28}H_{37}N_2O_6$ (M+H)$^+$ 497.2639; m/z $C_{28}H_{36}N_2O_6Na$ (M+Na)$^+$ 519.2463; HPLC-MS (ESI+): m/z 497.2 [100% (M+H)$^+$], m/z 993.4 [60%, (2M+H)$^+$].

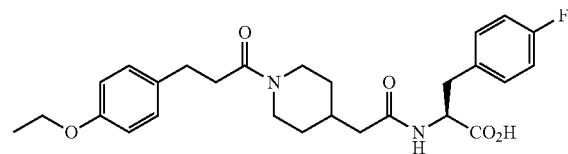 [SMILES: CCOc1ccc(CCC(=O)N2CCC(CC(=O)N[C@@H](Cc3ccc(F)cc3)C(=O)O)CC2)cc1]

Example 19. (S)-2-(2-(1-(3-(4-Ethoxyphenyl)propanoyl)piperidin-4-yl)acetamido)-3-(4-fluorophenyl)propanoic acid (SR5-002)

SR5-002 was obtained as a white foam (0.098 g, 97%) from SR4-175 (0.104 g, 0.209 mmol) using general method 3. HPLC: >98% [$t_R$=6.4 min, 65% MeOH, 35% water (with 0.1% TFA), 20 min]. $^1$H NMR (500 MHz, DMSO-$d_6$) δ 8.19-8.06 (m, 1H), 7.33-7.20 (m, 2H), 7.20-7.04 (m, 4H), 6.82 (dd, J=8.6, 2.8 Hz, 2H), 4.45 (m, 1H), 4.26 (m, 1H), 3.98 (q, J=6.9 Hz, 2H), 3.80-3.63 (m, 1H), 3.07 (dd, J=13.8, 4.6 Hz, 1H), 2.91-2.75 (m, 2H), 2.77-2.61 (m, 2H), 2.53 (m, 2H), 2.45-2.33 (m, 1H), 1.95 (d, J=7.0 Hz, 2H), 1.82-1.64 (m, 1H), 1.47 (m, 1H), 1.31 (t, J=7.0 Hz, 3H), 1.33-1.25 (m, 1H), 0.97-0.68 (m, 2H); $^{19}$F NMR (471 MHz, DMSO-$d_6$) δ −116.9 (m). HRMS (ESI+): m/z $C_{27}H_{34}FN_2O_5$(M+H)$^+$ 485.2443; m/z $C_{27}H_{33}FN_2O_5Na$ (M+Na)$^+$ 507.2269; HPLC-MS (ESI+): m/z 485.2 [100% (M+H)$^+$], m/z 507.2 [20%, (M+Na)$^+$].

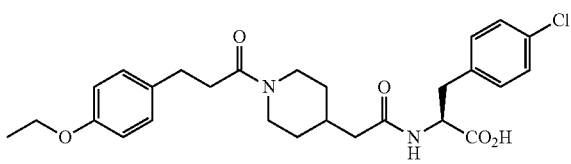 [SMILES: CCOc1ccc(CCC(=O)N2CCC(CC(=O)N[C@@H](Cc3ccc(Cl)cc3)C(=O)O)CC2)cc1]

Example 20. (S)-3-(4-Chlorophenyl)-2-(2-(1-(3-(4-ethoxyphenyl)propanoyl)piperidin-4-yl)acetamido)propanoic acid (SR5-003)

SR5-003 was obtained as a white foam (0.094 g, 92%) from SR4-176 (0.105 g, 0.203 mmol) using general method 3. HPLC: >98% [$t_R$=5.7 min, 75% MeOH, 25% water (with 0.1% TFA), 20 min]. $^1$H NMR (500 MHz, DMSO-d$_6$) δ 8.14 (dd, J=8.5, 1.9 Hz, 1H), 7.33 (d, J=8.1 Hz, 2H), 7.25 (d, J=8.2 Hz, 2H), 7.13 (dd, J=8.6, 3.4 Hz, 2H), 6.82 (dd, J=8.6, 2.9 Hz, 2H), 4.51-4.42 (m, 1H), 4.33-4.23 (m, 1H), 3.98 (q, J=6.9 Hz, 2H), 3.81-3.64 (m, 1H), 3.08 (dd, J=14.1, 4.9, Hz, 1H), 2.91-2.76 (m, 2H), 2.76-2.65 (m, 3H), 2.52 (m, 1H), 2.48-2.35 (m, 1H), 1.98-1.88 (m, 2H), 1.77-1.65 (m, 1H), 1.53-1.41 (m, 1H), 1.31 (t, J=7.0 Hz, 2H), 1.29-1.15 (m, 1H), 0.97-0.63 (m, 2H). HRMS (ESI+): m/z C$_{27}$H$_{34}$C$_1$N$_2$O$_5$ (M+H)$^+$ 501.2146; m/z C$_{27}$H$_{33}$C$_1$N$_2$O$_5$Na (M+Na)$^+$ 523.1973; HPLC-MS (ESI+): m/z 501.2 [100% (M+H)$^+$], (ESI−): m/z 499.0 [10%, (M−H)$^−$].

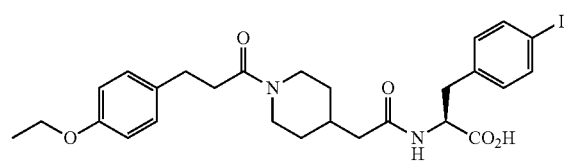 [SMILES: CCOc1ccc(CCC(=O)N2CCC(CC(=O)N[C@@H](Cc3ccc(I)cc3)C(=O)O)CC2)cc1]

Example 21. (S)-2-(2-(1-(3-(4-Ethoxyphenyl)propanoyl)piperidin-4-yl)acetamido)-3-(4-iodophenyl)propanoic acid (SR5-004)

SR5-004 was obtained as a white foam (0.130 g, 96%) from SR4-177 (0.139 g, 0.229 mmol) using general method 3. HPLC: >98% [$t_R$=6.6 min, 75% MeOH, 25% water (with 0.1% TFA), 20 min]. $^1$H NMR (500 MHz, DMSO-d$_6$) δ 12.7 (bs, 1H), 8.13 (d, J=8.5 Hz, 1H), 7.62 (dd, J=8.3, 2.0 Hz, 2H), 7.19-7.10 (m, 2H), 7.04 (d, J=8.1 Hz, 2H), 6.82 (dd, J=8.7, 3.2 Hz, 2H), 4.47 (ddd, J=10.6, 8.4, 4.6 Hz, 1H), 4.34-4.22 (m, 1H), 3.98 (q, J=6.9 Hz, 2H), 3.79-3.64 (m, 1H), 3.04 (m, 1H), 2.89-2.63 (m, 5H), 2.60-2.52 (m, 1H), 2.45-2.32 (m, 1H), 1.97-1.87 (m, 2H), 1.76-1.64 (m, 1H), 1.52-1.39 (m, 1H), 1.31 (t, J=7.0 Hz, 3H), 1.28-1.15 (m, 1H), 0.94-0.70 (m, 2H). HRMS (ESI+): m/z C$_{27}$H$_{34}$IN$_2$O$_5$ (M+H)$^+$ 593.1495; m/z C$_{27}$H$_{33}$IN$_2$O$_5$Na (M+Na)$^+$ 615.1324; HPLC-MS (ESI+): m/z 593.2 [100% (M+H)$^+$], (ESI−): m/z 591.0 [50%, (M−H)$^−$].

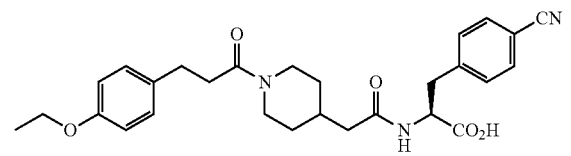 [SMILES: CCOc1ccc(CCC(=O)N2CCC(CC(=O)N[C@@H](Cc3ccc(C#N)cc3)C(=O)O)CC2)cc1]

Example 22. (S)-3-(4-Cyanophenyl)-2-(2-(1-(3-(4-ethoxyphenyl)propanoyl)piperidin-4-yl)acetamido)propanoic acid (SR5-005)

SR5-005 was obtained as a white foam (0.093 g, 89%) from SR4-179 (0.108 g, 0.213 mmol) using general method 3. HPLC: >98% [$t_R$=6.1 min, 60% MeOH, 40% water (with 0.1% TFA), 20 min]. $^1$H NMR (500 MHz, DMSO-d$_6$) δ 8.17 (d, J=8.3 Hz, 1H), 7.76 (d, J=8.3 Hz, 2H), 7.43 (d, J=8.2 Hz, 2H), 7.12 (dd, J=8.7, 2.5 Hz, 2H), 6.90-6.73 (m, 2H), 4.59-4.46 (m, 1H), 4.32-4.19 (m, 1H), 3.98 (q, J=7.0 Hz, 2H), 3.79-3.65 (m, 1H), 3.18 (dd, J=13.7, 4.6 Hz, 1H), 2.98-2.77 (m, 2H), 2.72 (m, 2H), 2.58-2.53 (m, 2H), 2.47-2.33 (m, 1H), 1.97-1.87 (m, 2H), 1.75-1.66 (m, 1H), 1.51-1.38 (m, 1H), 1.30 (t, J=7.0 Hz, 3H), 1.28-1.21 (m, 1H), 0.94-0.69 (m, 2H). HRMS (ESI+): m/z C$_{28}$H$_{34}$N$_3$O$_5$ (M+H)$^+$ 492.2486; m/z C$_{28}$H$_{33}$N$_3$O$_5$Na (M+Na)$^+$ 514.2317; HPLC-MS (ESI+): m/z 492.2 [80%, (M+H)$^+$], (ESI−): m/z 490.0 [50%, (M−H)$^−$].

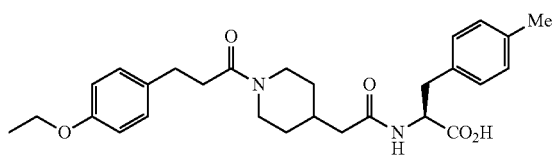 [SMILES: CCOc1ccc(CCC(=O)N2CCC(CC(=O)N[C@@H](Cc3ccc(C)cc3)C(=O)O)CC2)cc1]

Example 23. (S)-2-(2-(1-(3-(4-ethoxyphenyl)propanoyl)piperidin-4-yl)acetamido)-3-(p-tolyl)propanoic acid (SR5-006)

SR5-006 was obtained as a white foam (0.120 g, 93%) from SR4-180 (0.132 g, 0.267 mmol) using general method 3. HPLC: >98% [$t_R$=8.2 min, 65% MeOH, 35% water (with 0.1% TFA), 20 min]. $^1$H NMR (500 MHz, DMSO-d$_6$) δ 12.63 (s, 1H), 8.09 (d, J=8.3 Hz, 1H), 7.26-6.99 (m, 6H), 6.82 (dd, J=8.5, 3.6 Hz, 2H), 4.43 (m, 1H), 4.35-4.20 (m, 1H), 3.98 (q, J=6.9 Hz, 2H), 3.81-3.63 (m, 1H), 3.02 (dd, J=14.0, 4.6 Hz, 1H), 2.89-2.67 (m, 4H), 2.52 (m, 2H), 2.44-2.33 (m, 1H), 2.26 (s, 1H, rotamer), 2.23 (s, 1H, rotamer), 1.98-1.85 (m, 2H), 1.80-1.65 (m, 1H), 1.51-1.40 (m, 1H), 1.31 (t, J=7.0 Hz, 3H), 1.29-1.22 (m, 1H), 0.99-0.63 (m, 2H). HRMS (EST+): m/z C$_{28}$H$_{37}$N$_2$O$_5$ (M+H)$^+$ 481.2674; m/z C$_{28}$H$_{36}$N$_2$O$_5$Na (M+Na)$^+$ 503.2522; HPLC-MS (ESI+): m/z 481.2 [100%, (M+H)$^+$], (ESI−): m/z 479.4 [60%, (M−H)$^−$].

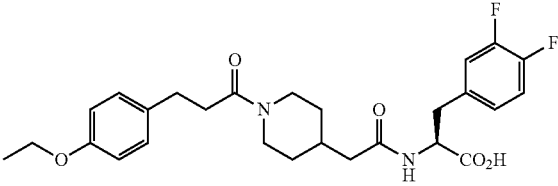

Example 24. (S)-3-(3,4-Difluorophenyl)-2-(2-(1-(3-(4-ethoxyphenyl)propanoyl)piperidin-4-yl)acetamido)propanoic acid (SR5-007)

SR5-007 was obtained as a white foam (0.110 g, 95%) from SR4-181 (0.119 g, 0.230 mmol) using general method 3. HPLC: >98% [$t_R$=7.4 min, 65% MeOH, 35% water (with 0.1% TFA), 20 min]. $^1$H NMR (500 MHz, DMSO-$d_6$) δ 12.73 (s, 1H), 8.15 (d, J=9.0 Hz, 1H), 7.42-7.24 (m, 2H), 7.12 (d, J=7.9 Hz, 2H), 7.08 (m, 1H), 6.81 (dd, J=8.7, 2.3 Hz, 2H), 4.55-4.40 (m, 1H), 4.33-4.21 (m, 1H), 3.98 (q, J=7.0 Hz, 2H), 3.81-3.65 (m, 1H), 3.09 (dd, J=13.9, 4.6 Hz, 1H), 2.90-2.67 (m, 5H), 2.51 (m, 1H), 2.41 (m, 1H), 2.02-1.93 (m, 2H), 1.78-1.69 (m, 1H), 1.54-1.41 (m, 1H), 1.30 (t, J=7.0 Hz, 3H), 1.33-1.27 (m, 1H), 1.04-0.68 (m, 2H); $^{19}$F NMR (471 MHz, DMSO-$d_6$) δ −139.5 (t, J=22.0 Hz); $^{19}$F NMR (471 MHz, DMSO-$d_6$) δ −139.3--139.5 (m), −142.3 (dd, J=22.2, 17.1 Hz). HRMS (ESI+): m/z $C_{27}H_{33}F_2N_2O_5$(M+H)$^+$ 503.2344; m/z $C_{27}H_{32}F_2N_2O_5$Na (M+Na)$^+$ 525.2171; HPLC-MS (ESI+): m/z 503.2 [100%, (M+H)$^+$], (ESI−): m/z 501.2 [100%, (M−H)$^-$].

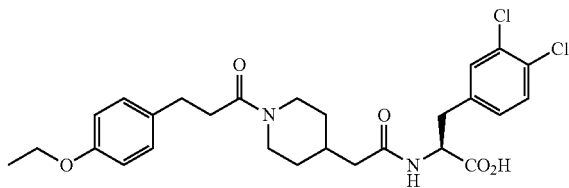 [SMILES: CCOc1ccc(CCC(=O)N2CCC(CC(=O)N[C@@H](Cc3ccc(Cl)c(Cl)c3)C(=O)O)CC2)cc1]

Example 25. (S)-3-(3,4-dichlorophenyl)-2-(2-(1-(3-(4-ethoxyphenyl)propanoyl)piperidin-4-yl)acetamido)propanoic acid (SR5-008)

SR5-008 was obtained as a white foam (0.109 g, 82%) from SR4-182 (0.134 g, 0.243 mmol) using general method 3. HPLC: >98% [$t_R$=8.3 min, 70% MeOH, 30% water (with 0.1% TFA), 20 min]. $^1$H NMR (500 MHz, DMSO-$d_6$) δ 8.16 (dd, J=8.6, 4.0 Hz, 1H), 7.54 (d, J=8.3 Hz, 1H), 7.50 (d, J=1.9 Hz, 1H), 7.24 (ddd, J=8.4, 3.8, 2.1 Hz, 1H), 7.12 (dd, J=8.7, 2.7 Hz, 2H), 6.81 (dd, J=8.6, 3.0 Hz, 2H), 4.51 (td, J=9.6, 8.9, 4.4 Hz, 1H), 4.33-4.22 (m, 1H), 4.02-3.92 (m, 2H), 3.80-3.62 (m, 1H), 3.17-3.05 (m, 1H), 2.88-2.61 (m, 5H), 2.54 (m, 1H), 2.47-2.32 (m, 1H), 1.93 (d, J=13.3 Hz, 2H), 1.70 (m, 1H), 1.46 (m, 1H), 1.31 (t, J=6.9 Hz, 3H), 1.18 (m, 1H), 0.97-0.67 (m, 2H). HRMS (ESI+): m/z $C_{27}H_{33}Cl_2N_2O_5$ (M+H)$^+$ 535.1753; m/z $C_{27}H_{32}Cl_2N_2O_5$Na (M+Na)$^+$ 557.1576; HPLC-MS (ESI+): m/z 535.2 [100%, (M+H)$^+$], (ESI−): m/z 533.1 [100%, (M−H)$^-$].

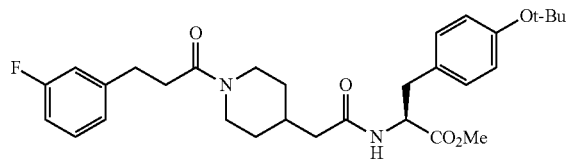 [SMILES: COC(=O)[C@H](Cc1ccc(OC(C)(C)C)cc1)NC(=O)CC1CCN(C(=O)CCc2cccc(F)c2)CC1]

Example 26. Methyl (S)-3-(4-(tert-butoxy)phenyl)-2-(2-(1-(3-(3-fluorophenyl)propanoyl)piperidin-4-yl)acetamido)propanoate (SR5-012)

SR5-012 was obtained as a white foam (0.169 g, 94%) from H-Tyr(OtBu)-OMe hydrochloride (0.118 g, 0.409 mmol) using general method 4. HPLC: >98% [$t_R$=3.5 min, 70% MeOH, 30% water (with 0.1% TFA), 20 min]. $^1$H NMR (500 MHz, DMSO-$d_6$) δ 8.28 (dd, J=7.9, 2.3 Hz, 1H), 7.36-7.27 (m, 1H), 7.15-7.04 (m, 4H), 7.01 (m, 1H), 6.86 (dd, J=8.5, 3.5 Hz, 2H), 4.55-4.42 (m, 1H), 4.27 (m, 1H), 3.81-3.68 (m, 2H), 3.60 (s, 3H), 3.04-2.93 (m, 1H), 2.91- 2.70 (m, 4H), 2.59 (m, 2H), 2.48 (m, 1H), 1.97 (m, 2H), 1.76 (m, 1H), 1.51 (m, 1H), 1.26 (s, 5H, rotamer), 1.22 (s, 4H, rotamer), 0.98-0.71 (m, 2H); $^{19}$F NMR (471 MHz, DMSO-$d_6$) δ −113.8--113.9 (m). HRMS (ESI+): m/z $C_{30}H_{40}FN_2O_5$ (M+H)$^+$ 527.2914; m/z $C_{30}H_{39}FN_2O_5$Na (M+Na)$^+$ 549.2728; HPLC-MS (ESI+): m/z 527.2 [100%, (M+H)$^+$], m/z 549.2 [90%, (M+Na)$^+$].

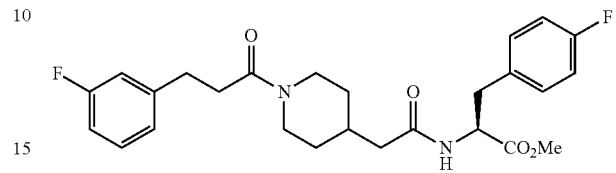

Example 27. Methyl (S)-3-(4-fluorophenyl)-2-(2-(1-(3-(3-fluorophenyl)propanoyl)piperidin-4-yl)acetamido)propanoate (SR5-013)

SR5-013 was obtained as a white foam (0.152 g, 95%) from H-Phe(4-F)—OMe hydrochloride (0.096 g, 0.409 mmol) using general method 4. HPLC: >98% [$t_R$=4.8 min, 50% MeOH, 50% water (with 0.1% TFA), 20 min]. $^1$H NMR (500 MHz, DMSO-$d_6$) δ 8.28 (d, J=8.0 Hz, 1H), 7.40-7.20 (m, 3H), 7.18-7.06 (m, 4H), 7.00 (t, J=8.8 Hz, 1H), 4.50 (ddd, J=14.3, 9.0, 5.7 Hz, 1H), 4.33-4.18 (m, 1H), 3.83-3.69 (m, 1H), 3.61 (s, 3H), 3.04 (dd, J=13.8, 5.2 Hz, 1H), 2.95-2.73 (m, 4H), 2.60 (m, 2H), 2.48-2.35 (m, 1H), 1.96 (d, J=7.2 Hz, 2H), 1.81-1.67 (m, 1H), 1.53-1.43 (m, 1H), 1.40-1.27 (m, 1H), 0.99-0.72 (m, 2H); $^{19}$F NMR (471 MHz, DMSO-$d_6$) δ −113.8--113.9 (m), −116.56--116.71 (m). HRMS (ESI+): m/z $C_{26}H_{31}F_2N_2O_4$(M+H)$^+$ 473.2246; m/z $C_{26}H_{30}F_2N_2O_4$Na (M+Na)$^+$ 495.2061; HPLC-MS (ESI+): m/z 495.2 [60%, (M+H)$^+$], m/z 549.2 [50%, (M+Na)$^+$].

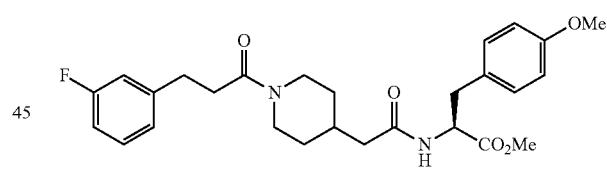

Example 28. Methyl (S)-2-(2-(1-(3-(3-fluorophenyl)propanoyl)piperidin-4-yl)acetamido)-3-(4-methoxyphenyl)propanoate (SR5-014)

SR5-014 was obtained as a white foam (0.156 g, 94%) from H-Tyr(OMe)-OMe hydrochloride (0.100 g, 0.409 mmol) using general method 4. HPLC: >98% [$t_R$=4.8 min, 55% MeOH, 45% water (with 0.1% TFA), 20 min]. $^1$H NMR (500 MHz, DMSO-$d_6$) δ 8.24 (d, J=8.0 Hz, 1H), 7.31 (m, 1H), 7.13 (d, J=8.6 Hz, 1H), 7.09 (m, 2H), 7.04-6.93 (m, 1H), 6.83 (d, J=8.6 Hz, 2H), 4.45 (ddd, J=10.2, 7.7, 4.9 Hz, 1H), 4.33-4.22 (m, 1H), 3.82-3.72 (m, 1H), 3.72 (s, 1.5H), 3.68 (s, 1H), 3.61 (s, 3H), 2.98 (dd, J=13.8, 5.2 Hz, 1H), 2.93-2.71 (m, 4H), 2.60 (m, 2H), 2.48-2.36 (m, 1H), 1.96 (d, J=7.3 Hz, 2H), 1.79-1.70 (m, 1H), 1.56-1.42 (m, 1H), 1.37-1.21 (m, 1H), 0.96-0.73 (m, 2H); $^{19}$F NMR (471 MHz, DMSO-$d_6$) δ −113.8--114.0 (m). HRMS (ESI+): m/z $C_{27}H_{34}FN_2O_5$(M+H)$^+$485.2440; m/z $C_{27}H_{33}FN_2O_5$Na (M+Na)⁺ 507.2258; HPLC-MS (ESI+): m/z 485.2 [100%, (M+H)⁺], m/z 507.2 [10%, (M+Na)⁺].

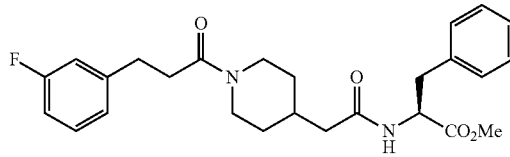

Example 29. Methyl (S)-2-(2-(1-(3-(3-fluorophenyl)propanoyl)piperidin-4-yl)acetamido)-3-(4-(trifluoromethyl)phenyl)propanoate (SR5-015)

SR5-015 was obtained as a white foam (0.172 g, 97%) from H-Phe(4-CF₃)—OMe hydrochloride (0.116 g, 0.409 mmol) using general method 4. HPLC: >98% [$t_R$=10.2 min, 60% MeOH, 40% water (with 0.1% TFA), 20 min]. ¹H NMR (500 MHz, DMSO-$d_6$) δ 8.33 (d, J=8.2 Hz, 1H), 7.65 (d, J=7.9 Hz, 2H), 7.46 (d, J=7.9 Hz, 2H), 7.37-7.26 (m, 1H), 7.08 (m, 2H), 7.00 (m, 1H), 4.66-4.54 (m, 1H), 4.33-4.17 (m, 1H), 3.82-3.66 (m, 1H), 3.64 (s, 2H), 3.18 (dd, J=13.7, 5.0 Hz, 1H), 2.94 (dd, J=13.4, 11.0 Hz, 1H), 2.89-2.73 (m, 4H), 2.59 (m, 1H), 2.49-2.34 (m, 1H), 2.03-1.87 (m, 2H), 1.72 (m, 1H), 1.45 (m, J=13.1 Hz, 1H), 1.29-1.21 (m, 1H), 0.99-0.65 (m, 2H); ¹⁹F NMR (471 MHz, DMSO-$d_6$) δ -60.8 (m), -113.9 (m). HRMS (ESI+): m/z $C_{27}H_{31}F_4N_2O_4$(M+H)⁺ 523.2209; m/z $C_{27}H_{30}F_4N_2O_4Na$ (M+Na)⁺ 545.2027; HPLC-MS (ESI+): m/z 523.2 [100%, (M+H)⁺], m/z 545.2 [100%, (M+Na)⁺].

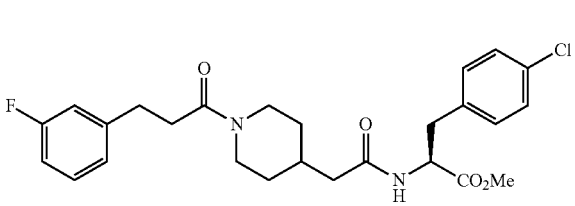 [SMILES: COC(=O)[C@H](Cc1ccc(Cl)cc1)NC(=O)CC1CCN(C(=O)CCc2cccc(F)c2)CC1]

Example 30. Methyl (S)-3-(4-chlorophenyl)-2-(2-(1-(3-(3-fluorophenyl)propanoyl)piperidin-4-yl)acetamido)propanoate (SR5-016)

SR5-016 was obtained as a white foam (0.154 g, 93%) from H-Phe(4-Cl)—OMe hydrochloride (0.102 g, 0.409 mmol) using general method 4. HPLC: >98% [$t_R$=7.4 min, 50% MeOH, 50% water (with 0.1% TFA), 20 min]. ¹H NMR (500 MHz, DMSO-$d_6$) δ 8.28 (d, J=8.1 Hz, 1H), 7.43-7.27 (m, 3H), 7.25 (d, J=8.0 Hz, 2H), 7.13-7.04 (m, 2H), 7.00 (m, 1H), 4.53 (td, J=9.2, 8.8, 5.1 Hz, 1H), 4.35-4.22 (m, 1H), 3.83-3.71 (m, 1H), 3.62 (s, 3H), 3.12-3.00 (m, 1H), 2.91-2.76 (m, 4H), 2.60 (m, 2H), 2.48-2.36 (m, 1H), 1.96 (d, J=7.2 Hz, 2H), 1.77-1.64 (m, 1H), 1.54-1.42 (m, 1H), 1.35-1.21 (m, 1H), 0.98-0.69 (m, 2H); ¹⁹F NMR (471 MHz, DMSO-$d_6$) δ -113.9 (m). HRMS (ESI+): m/z $C_{26}H_{31}C_{1}FN_2O_4$(M+H)⁺ 489.1943; m/z $C_{26}H_{30}ClFN_2O_4Na$ (M+Na)⁺ 511.1761; HPLC-MS (ESI+): m/z 489.2 [100%, (M+H)⁺], m/z 545.2 [10%, (M+Na)⁺].

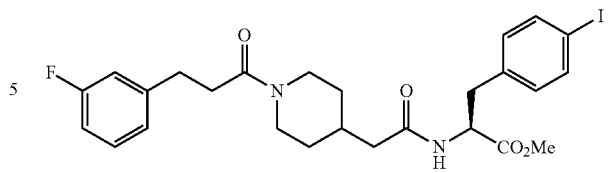

Example 31. Methyl (S)-2-(2-(1-(3-(3-fluorophenyl)propanoyl)piperidin-4-yl)acetamido)-3-(4-iodophenyl)propanoate (SR5-017)

SR5-017 was obtained as a white foam (0.189 g, 95%) from H-Phe(4-I)—OMe hydrochloride (0.140 g, 0.409 mmol) using general method 4. HPLC: >98% [$t_R$=5.2 min, 60% MeOH, 40% water (with 0.1% TFA), 20 min]. ¹H NMR (500 MHz, DMSO-$d_6$) δ 8.27 (d, J=8.1 Hz, 1H), 7.63 (d, J=8.2 Hz, 2H), 7.36-7.27 (m, 1H), 7.16-7.07 (m, 2H), 7.04 (d, J=7.7 Hz, 2H), 7.04-6.96 (m, 1H), 4.52 (ddd, J=10.3, 8.1, 5.0 Hz, 1H), 4.36-4.21 (m, 1H), 3.83-3.70 (m, 1H), 3.63 (s, 3H), 3.10-2.98 (m, 1H), 2.92-2.75 (m, 4H), 2.66-2.58 (m, 2H), 2.48-2.35 (m, 1H), 2.04-1.84 (m, 2H), 1.77-1.64 (m, 1H), 1.52-1.39 (m, 1H), 1.38-1.18 (m, 1H), 1.00-0.64 (m, 2H); ¹⁹F NMR (471 MHz, DMSO-$d_6$) δ -113.8--113.9 (m). HRMS (ESI+): m/z $C_{26}H_{31}FIN_2O_4$(M+H)⁺ 581.1298; m/z $C_{26}H_{30}FIN_2O_4Na$ (M+Na)⁺ 603.1114; HPLC-MS (ESI+): m/z 581.2 [100%, (M+H)⁺], m/z 603.2 [50%, (M+Na)⁺].

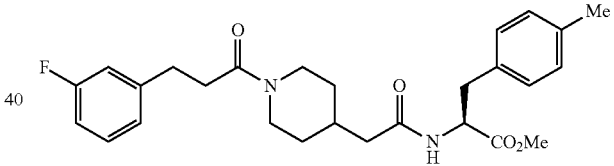

Example 32. Methyl (S)-2-(2-(1-(3-(3-fluorophenyl)propanoyl)piperidin-4-yl)acetamido)-3-(p-tolyl)propanoate (SR5-018)

SR5-018 was obtained as a white foam (0.151 g, 94%) from H-Phe(4-Me)-OMe hydrochloride (0.094 g, 0.409 mmol) using general method 4. HPLC: >98% [$t_R$=7.1 min, 45% MeOH, 55% water (with 0.1% TFA), 20 min]. ¹H NMR (500 MHz, DMSO-$d_6$) δ 8.24 (d, J=8.0 Hz, 1H), 7.38-7.25 (m, 1H), 7.25-7.03 (m, 6H), 7.04-6.93 (m, 1H), 4.55-4.41 (m, 1H), 4.35-4.20 (m, 1H), 3.81-3.68 (m, 1H), 3.61 (s, 3H), 3.00 (dd, J=13.8, 5.1 Hz, 1H), 2.91-2.73 (m, 4H), 2.66-2.56 (m, 2H), 2.48-2.36 (m, 1H), 2.26 (s, 3H), 1.96 (d, J=7.2 Hz, 2H), 1.74 (s, 1H), 1.56-1.39 (m, 1H), 1.38-1.20 (m, 1H), 0.94-0.69 (m, 2H); ¹⁹F NMR (471 MHz, DMSO-$d_6$) δ -113.8--114.0 (m). HRMS (ESI+): m/z $C_{27}H_{34}FN_2O_4$(M+H)⁺ 469.2491; m/z $C_{27}H_{33}FN_2O_4Na$ (M+Na)⁺ 491.2308; HPLC-MS (ESI+): m/z 469.2 [100%, (M+H)⁺], m/z 491.2 [40%, (M+Na)⁺].

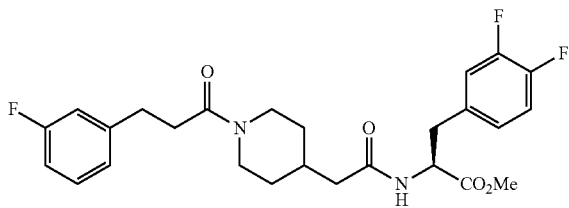 [SMILES: COC(=O)[C@H](Cc1ccc(F)c(F)c1)NC(=O)CC1CCN(C(=O)CCc2cccc(F)c2)CC1]

Example 33. Methyl (S)-3-(3,4-difluorophenyl)-2-(2-(1-(3-(3-fluorophenyl)propanoyl)piperidin-4-yl)acetamido)propanoate (SR5-019)

SR5-019 was obtained as a white foam (0.158 g, 95%) from H-Phe(3,4-$F_2$)—OMe hydrochloride (0.103 g, 0.409 mmol) using general method 4. HPLC: >98% [$t_R$=5.3 min, 45% MeOH, 55% water (with 0.1% TFA), 20 min]. $^1$H NMR (500 MHz, DMSO-$d_6$) δ 8.29 (d, J=8.2 Hz, 1H), 7.38-7.25 (m, 3H), 7.15-7.03 (m, 3H), 7.03-6.96 (m, 1H), 4.60-4.48 (m, 1H), 4.33-4.21 (m, 1H), 3.83-3.69 (m, 1H), 3.63 (s, 3H), 3.07 (dd, J=13.8, 5.0 Hz, 1H), 2.93-2.77 (m, 4H), 2.60 (m, 2H), 2.48-2.39 (m, 1H), 2.02-1.92 (m, 2H), 1.80-1.70 (m, 1H), 1.55-1.40 (m, 1H), 1.39-1.28 (m, 1H), 0.92-0.74 (m, 2H); $^{19}$F NMR (471 MHz, DMSO-$d_6$) δ −113.9 (m), −139.4 (m), −142.08 (m). HRMS (ESI+): m/z $C_{26}H_{30}F_3N_2O_4$(M+H)$^+$ 491.2154; m/z $C_{26}H_{29}F_3N_2O_4Na$ (M+Na)$^+$ 513.1963; HPLC-MS (ESI+): m/z 491.2 [100%, (M+H)$^+$], m/z 513.2 [50%, (M+Na)$^+$].

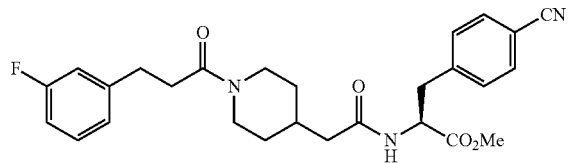 [SMILES: COC(=O)[C@H](Cc1ccc(C#N)cc1)NC(=O)CC1CCN(C(=O)CCc2cccc(F)c2)CC1]

Example 34. Methyl (S)-3-(4-cyanophenyl)-2-(2-(1-(3-(3-fluorophenyl)propanoyl)piperidin-4-yl)acetamido)propanoate (SR5-021)

SR5-021 was obtained as a white foam (0.160 g, 98%) from H-Phe(3,4-$Cl_2$)—OMe hydrochloride (0.098 g, 0.409 mmol) using general method 4. HPLC: >98% [$t_R$=4.7 min, 50% MeOH, 50% water (with 0.1% TFA), 20 min]. $^1$H NMR (500 MHz, DMSO-$d_6$) δ 8.37-8.28 (m, 1H), 7.76 (d, J=8.0 Hz, 2H), 7.44 (d, J=8.2 Hz, 2H), 7.37-7.26 (m, 1H), 7.14-7.05 (m, 2H), 7.00 (td, J=8.8, 2.6 Hz, 1H), 4.65-4.52 (m, 1H), 4.34-4.23 (m, 1H), 3.75 (m, 1H), 3.63 (s, 3H), 3.17 (dd, J=13.8, 5.0 Hz, 1H), 2.94 (dd, J=13.8, 10.4 Hz, 1H), 2.91-2.76 (m, 3H), 2.68-2.55 (m, 2H), 2.49-2.33 (m, −1H), 2.00-1.89 (m, 2H), 1.80-1.65 (m, 1H), 1.52-1.40 (m, 1H), 1.36-1.24 (m, 1H), 0.98-0.70 (m, 2H); $^{19}$F NMR (471 MHz, DMSO-$d_6$) δ −113.9 (m). HRMS (ESI+): m/z $C_{27}H_{31}FN_3O_4$ (M+H)$^+$ 480.2288; m/z $C_{27}H_{30}FN_3O_4Na$ (M+Na)$^+$ 502.2106; HPLC-MS (ESI+): m/z 480.2 [100%, (M+H)$^+$], m/z 502.2 [50%, (M+Na)$^+$].

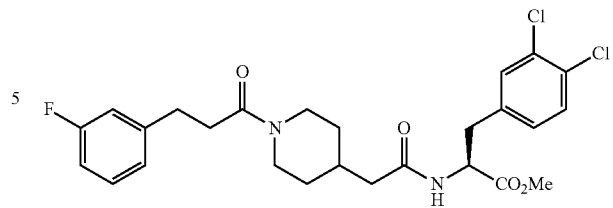

Example 35. Methyl (S)-3-(3,4-dichlorophenyl)-2-(2-(1-(3-(3-fluorophenyl)propanoyl)piperidin-4-yl)acetamido)propanoate (SR5-022)

SR5-022 was obtained as a white foam (0.170 g, 95%) from H-Phe(3,4-$Cl_2$)—OMe hydrochloride (0.116 g, 0.409 mmol) using general method 4. HPLC: >98% [$t_R$=6.2 min, 60% MeOH, 40% water (with 0.1% TFA), 20 min]. $^1$H NMR (500 MHz, DMSO-$d_6$) δ 8.30 (d, J=4.2 Hz, 1H), 7.60-7.47 (m, 2H), 7.35-7.27 (m, 1H), 7.27-7.20 (m, 1H), 7.13-7.04 (m, 2H), 7.04-6.96 (m, 1H), 4.58 (ddd, J=14.6, 7.2, 4.5 Hz, 1H), 4.33-4.24 (m, 1H), 3.81-3.67 (m, 2H), 3.64 (s, 3H), 3.15-3.05 (m, 1H), 2.92-2.77 (m, 4H), 2.66-2.54 (m, 2H), 2.49-2.33 (m, −1H), 2.02-1.88 (m, 2H), 1.77-1.65 (m, 1H), 1.52-1.40 (m, 1H), 1.35-1.14 (m, 1H), 0.95-0.71 (m, 2H); $^{19}$F NMR (471 MHz, DMSO-$d_6$) δ −113.8−−113.9 (m). HRMS (ESI+): m/z $C_{26}H_{30}Cl_2FN_2O_4$(M+H)$^+$ 480.2288; m/z $C_{26}H_{29}Cl_2FN_2O_4Na$ (M+Na)$^+$ 502.2106; HPLC-MS (ESI+): m/z 480.2 [100%, (M+H)$^+$], m/z 502.2 [50%, (M+Na)$^+$].

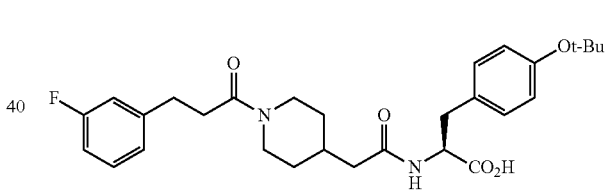

Example 36. (S)-3-(4-(tert-Butoxy)phenyl)-2-(2-(1-(3-(3-fluorophenyl)propanoyl)piperidin-4-yl)acetamido)propanoic acid (SR5-023)

SR5-023 was obtained as a white foam (0.119 g, 93%) from SR5-012 (0.131 g, 0.248 mmol) using general method 3. HPLC: >98% [$t_R$=5.8 min, 70% MeOH, 30% water (with 0.1% formic acid), 20 min]. $^1$H NMR (500 MHz, DMSO-$d_6$) δ 8.12 (d, J=8.3 Hz, 1H), 7.36-7.25 (m, 1H), 7.19-7.05 (m, 4H), 7.00 (m, 1H), 6.90-6.81 (m, 2H), 4.50-4.37 (m, 1H), 4.32-4.19 (m, 1H), 3.83-3.61 (m, 1H), 3.09-2.96 (m, 1H), 2.90-2.68 (m, 4H), 2.63-2.54 (m, 2H), 2.49-2.38 (m, −1H), 2.03-1.92 (m, −2H), 1.83-1.69 (m, 1H), 1.58-1.42 (m, 1H), 1.42-1.31 (m, 1H), 1.31-1.16 (m, 9H), 0.99-0.68 (m, 2H); $^{19}$F NMR (471 MHz, DMSO-$d_6$) δ −113.9 (m). HRMS (ESI+): m/z $C_{29}H_{38}FN_2O_5$(M+H)$^+$ 513.2751; m/z $C_{29}H_{37}FN_2O_5Na$ (M+Na)$^+$ 535.2582; HPLC-MS (ESI+): m/z 513.2 [80%, (M+H)$^+$]. (EST−): m/z 511.2 [100%. (M−H)$^−$].

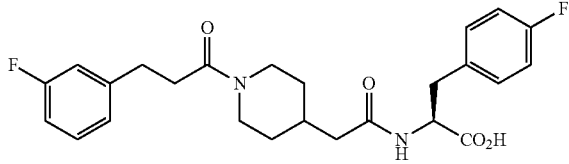 [SMILES: O=C(CC1CCN(C(=O)CCc2cccc(F)c2)CC1)N[C@@H](Cc1ccc(F)cc1)C(=O)O]

Example 37. (S)-3-(4-Fluorophenyl)-2-(2-(1-(3-(3-fluorophenyl)propanoyl)piperidin-4-yl)acetamido)propanoic acid (SR5-024)

SR5-024 was obtained as a white foam (0.094 g, 95%) from SR5-013 (0.102 g, 0.216 mmol) using general method 3. HPLC: >98% [$t_R$=8.3 min, 60% MeOH, 40% water (with 0.1% TFA), 20 min]. $^1$H NMR (500 MHz, DMSO-$d_6$) δ 7.38-7.25 (m, 2H), 7.13-7.04 (m, 4H), 7.00 (dd, J=10.0, 7.8 Hz, 3H), 4.27 (t, J=12.2 Hz, 1H), 4.04 (tt, J=7.1, 3.8 Hz, 1H), 3.76 (t, J=15.2 Hz, 1H), 3.05 (dd, J=14.3, 4.9 Hz, 1H), 2.94-2.78 (m, 3H), 2.76-2.67 (m, 1H), 2.67-2.53 (m, 2H), 2.50-2.37 (m, 1H), 1.98-1.86 (m, 2H), 1.81-1.68 (m, 1H), 1.57-1.46 (m, 1H), 1.46-1.33 (m, 1H), 1.00-0.71 (m, 2H); $^{19}$F NMR (471 MHz, DMSO-$d_6$) δ −113.9 (m), −116.9 (m). HRMS (ESI+): m/z $C_{25}H_{29}F_2N_2O_4$(M+H)$^+$ 459.2092; m/z $C_{25}H_{28}F_2N_2O_4$Na (M+Na)$^+$ 481.1918; HPLC-MS (ESI+): m/z 459.2 [80%, (M+H)$^+$], (ESI−): m/z 457.2 [50%, (M−H)$^−$].

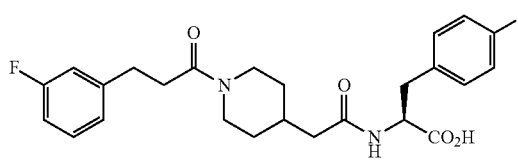

Example 38. (S)-2-(2-(1-(3-(3-Fluorophenyl)propanoyl)piperidin-4-yl)acetamido)-3-(4-methoxyphenyl)propanoic acid (SR5-025)

SR5-025 was obtained as a white foam (0.104 g, 95%) from SR5-014 (0.113 g, 0.233 mmol) using general method 3. HPLC: >98% [$t_R$=8.3 min, 60% MeOH, 40% water (with 0.1% TFA), 20 min]. $^1$H NMR (500 MHz, DMSO-$d_6$) δ 12.62 (s, 1H), 8.09 (d, J=8.3 Hz, 1H), 7.37-7.27 (m, 1H), 7.14 (d, J=8.6 Hz, 2H), 7.12-7.05 (m, 2H), 7.05-6.95 (m, 1H), 6.83 (d, J=8.6 Hz, 2H), 4.49-4.34 (m, 1H), 4.34-4.18 (m, 1H), 3.80-3.73 (m, 1H), 3.72 (s, 1.5H, rotamer), 3.68 (s, 1.5H, rotamer), 3.00 (dd, J=13.9, 4.6 Hz, 1H), 2.94-2.77 (m, 3H), 2.74 (dd, J=13.8, 10.3 Hz, 1H), 2.67-2.56 (m, 2H), 2.49-2.32 (m, -1H), 2.05-1.83 (m, 2H), 1.83-1.64 (m, 1H), 1.56-1.40 (m, 1H), 1.37-1.20 (m, 1H), 0.97-0.67 (m, 2H); $^{19}$F NMR (471 MHz, DMSO-$d_6$) δ −113.9 (m). HRMS (ESI+): m/z $C_{26}H_{32}FN_2O_5$(M+H)$^+$ 471.2287; m/z $C_{26}H_{31}FN_2O_5$Na (M+Na)$^+$ 493.2115; HPLC-MS (EST+): m/z 471.2 [80%, (M+H)$^+$], (ESI−): m/z 469.2 [40%, (M−H)$^−$].

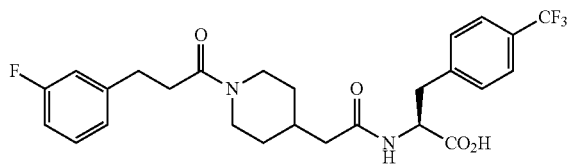 [SMILES: O=C(CC1CCN(C(=O)CCc2cccc(F)c2)CC1)N[C@@H](Cc1ccc(C(F)(F)F)cc1)C(=O)O]

Example 39. (S)-2-(2-(1-(3-(3-Fluorophenyl)propanoyl)piperidin-4-yl)acetamido)-3-(4-(trifluoromethyl)phenyl)propanoic acid (SR5-026)

SR5-026 was obtained as a white foam (0.128 g, 96%) from SR5-015 (0.137 g, 0.262 mmol) using general method 3. HPLC: >98% [$t_R$=5.2 min, 70% MeOH, 30% water (with 0.1% TFA), 20 min]. $^1$H NMR (500 MHz, DMSO-$d_6$) δ 8.20 (d, J=8.4 Hz, 1H), 7.64 (d, J=8.0 Hz, 2H), 7.46 (d, J=8.0 Hz, 2H), 7.37-7.24 (m, 1H), 7.12-7.06 (m, 2H), 7.05-6.94 (m, 1H), 4.54 (ddd, J=10.3, 8.4, 4.9 Hz, 1H), 4.31-4.17 (m, 1H), 3.81-3.61 (m, 1H), 3.19 (dd, J=13.8, 4.6 Hz, 1H), 2.90 (dd, J=13.4, 10.9 Hz, 1H), 2.85-2.69 (m, 3H), 2.65-2.53 (m, 2H), 2.48-2.31 (m, 1H), 1.97-1.89 (m, 2H), 1.81-1.64 (m, 1H), 1.50-1.40 (m, 1H), 1.27-1.16 (m, 1H), 0.94-0.65 (m, 2H); $^{19}$F NMR (471 MHz, DMSO-$d_6$) δ −60.79, (s), 6-113.8-−114.0 (m). HRMS (ESI+): m/z $C_{26}H_{29}F_4N_2O_4$(M+H)$^+$ 509.2051; m/z $C_{26}H_{28}F_4N_2O_4$Na (M+Na)$^+$ 531.1879; HPLC-MS (ESI+): m/z 509.2 [80%, (M+H)$^+$], (ESI−): m/z 531.2 [40%, (M−H)$^−$].

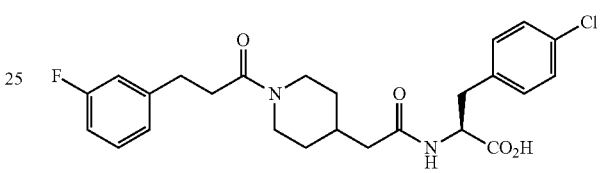

Example 40. (S)-3-(4-Chlorophenyl)-2-(2-(1-(3-(3-fluorophenyl)propanoyl)piperidin-4-yl)acetamido)propanoic acid (SR5-027)

SR5-027 was obtained as a white foam (0.121 g, 90%) from SR5-016 (0.138 g, 0.282 mmol) using general method 3. HPLC: >98% [$t_R$=4.8 min, 70% MeOH, 30% water (with 0.1% TFA), 20 min]. $^1$H NMR (500 MHz, DMSO-$d_6$) δ 12.74 (s, 1H), 8.15 (d, J=8.4 Hz, 1H), 7.36-7.28 (m, 3H), 7.25 (d, J=8.4 Hz, 2H), 7.13-7.05 (m, 2H), 7.00 (tt, J=9.0, 2.8 Hz, 1H), 4.53-4.42 (m, 1H), 4.32-4.22 (m, 1H), 3.81-3.67 (m, 1H), 3.08 (dd, J=13.6, 4.6 Hz, 1H), 2.90-2.74 (m, 4H), 2.66-2.55 (m, 2H), 2.49-2.34 (m, 1H), 1.98-1.87 (m, 2H), 1.81-1.65 (m, 1H), 1.53-1.40 (m, 1H), 1.32-1.20 (m, 1H), 0.97-0.70 (m, 2H); $^{19}$F NMR (471 MHz, DMSO-$d_6$) δ −113.9 (m). HRMS (ESI+): m/z $C_{25}H_{29}Cl_1FN_2O_4$(M+H)$^+$ 475.1788; m/z $C_{25}H_{28}ClFN_2O_4$Na (M+Na)$^+$ 497.1614; HPLC-MS (EST+): m/z 475.2 [100%, (M+H)$^+$], (ESI−): m/z 473.2 [100%, (M−H)$^−$].

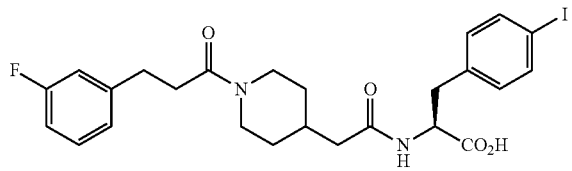 [SMILES: O=C(CC1CCN(C(=O)CCc2cccc(F)c2)CC1)N[C@@H](Cc1ccc(I)cc1)C(=O)O]

Example 41. (S)-2-(2-(1-(3-(3-Fluorophenyl)propanoyl)piperidin-4-yl)acetamido)-3-(4-iodophenyl)propanoic acid (SR5-028)

SR5-028 was obtained as a white foam (0.151 g, 95%) from SR5-017 (0.162 g, 0.279 mmol) using general method 3. HPLC: >98% [$t_R$=4.3 min, 60% MeOH, 40% water (with 0.1% TFA), 20 min]. ¹H NMR (500 MHz, DMSO-d₆) δ 8.14 (d, J=8.4 Hz, 1H), 7.63 (d, J=8.2 Hz, 2H), 7.41-7.21 (m, 1H), 7.15-7.05 (m, 2H), 7.04 (d, J=8.0 Hz, 2H), 7.04-6.96 (m, 1H), 4.56-4.36 (m, 1H), 4.29 (m, 1H), 3.84-3.67 (m, 1H), 3.09-2.95 (m, 1H), 2.91-2.68 (m, 4H), 2.67-2.58 (m, 2H), 2.48-2.34 (m, 1H), 1.98-1.87 (m, 2H), 1.79-1.63 (m, 1H), 1.49-1.40 (m, 1H), 1.35-1.16 (m, 1H), 0.97-0.68 (m, 2H); ¹⁹F NMR (471 MHz, DMSO-d₆) δ −113.9 (m). HRMS (ESI+): m/z C₂₅H₂₉FIN₂O₄(M+H)⁺567.1142; m/z C₂₅H₂₈FIN₂O₄Na (M+Na)⁺ 589.0970; HPLC-MS (ESI+): m/z 567.2 [80%, (M+H)⁺], (ESI−): m/z 565.2 [100%, (M−H)⁻].

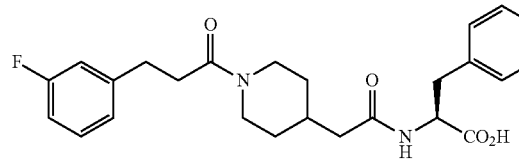

Example 42. (S)-2-(2-(1-(3-(3-Fluorophenyl)propanoyl)piperidin-4-yl)acetamido)-3-(p-tolyl)propanoic acid (SR5-030)

SR5-030 was obtained as a white foam (0.079 g, 87%) from SR5-018 (0.094 g, 0.201 mmol) using general method 3. HPLC: >98% [t$_R$=6.2 min, 50% MeOH, 50% water (with 0.1% TFA), 20 min]. ¹H NMR (500 MHz, DMSO-d₆) δ 12.63 (s, 1H), 8.10 (d, J=8.3 Hz, 1H), 7.36-7.26 (m, 1H), 7.22-7.04 (m, 6H), 7.04-6.93 (m, 1H), 4.53-4.35 (m, 1H), 4.35-4.18 (m, 1H), 3.85-3.63 (m, 1H), 3.06-2.98 (m, 1H), 2.94-2.65 (m, 4H), 2.65-2.54 (m, 2H), 2.48-2.33 (m, 1H), 2.26 (s, 1.5H, rotamer), 2.23 (s, 1.5H, rotamer), 1.99-1.86 (m, 2H), 1.82-1.65 (m, 1H), 1.53-1.40 (m, 1H), 1.36-1.21 (m, 1H), 0.97-0.66 (m, 2H); ¹⁹F NMR (471 MHz, DMSO-d₆) δ −113.9 (m). HRMS (ESI+): m/z C₂₆H₃₂FN₂O₄(M+H)⁺ 455.2331; m/z C₂₆H₃₁FN₂O₄Na (M+Na)⁺ 477.2155; HPLC-MS (ESI+): m/z 456.2 [80%, (M+H)⁺], (ESI−): m/z 453.2 [60%, (M−H)⁻].

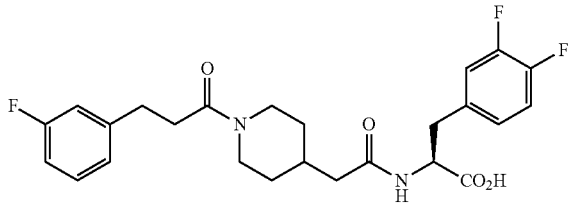 [SMILES: O=C(CC1CCN(C(=O)CCc2cccc(F)c2)CC1)N[C@@H](Cc1ccc(F)c(F)c1)C(=O)O]

Example 43. (S)-3-(3,4-Difluorophenyl)-2-(2-(1-(3-(3-fluorophenyl)propanoyl)piperidin-4-yl)acetamido)propanoic acid (SR5-031)

SR5-031 was obtained as a white foam (0.106 g, 90%) from SR5-019 (0.121 g, 0.246 mmol) using general method 3. HPLC: >98% [t$_R$=10.2 min, 60% MeOH, 40% water (with 0.1% TFA), 20 min]. ¹H NMR (500 MHz, DMSO-d₆) δ 8.16 (d, J=8.4 Hz, 1H), 7.43-7.20 (m, 3H), 7.15-7.04 (m, 3H), 7.04-6.94 (m, 1H), 4.53-4.40 (m, 1H), 4.34-4.19 (m, 1H), 3.84-3.66 (m, 1H), 3.09 (dd, J=13.9, 4.6 Hz, 1H), 2.90-2.72 (m, 4H), 2.66-2.55 (m, 2H), 2.48-2.35 (m, 1H), 1.96 (dd, J=7.0, 1.9 Hz, 2H), 1.82-1.66 (m, 1H), 1.53-1.43 (m, 1H), 1.38-1.21 (m, 1H), 0.99-0.69 (m, 2H); ¹⁹F NMR (471 MHz, DMSO-d₆) δ −113.88-−113.97 (m), −139.53 (m), 142.2-−142.4 (m); ¹⁹F NMR (471 MHz, DMSO-d₆) δ −113.9 (m), −139.4-−139.6 (m), −142.2-−142.4 (m). HRMS (ESI+): m/z C₂₅H₂₈F₃N₂O₄(M+H)⁺ 477.1989; m/z C₂₅H₂₇F₃N₂O₄Na (M+Na)⁺ 499.1816; HPLC-MS (ESI+): m/z 477.2 [100%, (M+H)⁺], (ESI−): m/z 475.2 [100%, (M−H)⁻].

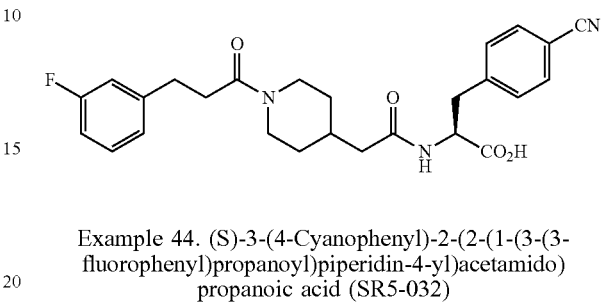

Example 44. (S)-3-(4-Cyanophenyl)-2-(2-(1-(3-(3-fluorophenyl)propanoyl)piperidin-4-yl)acetamido) propanoic acid (SR5-032)

SR5-032 was obtained as a white foam (0.119 g, 97%) from SR5-021 (0.126 g, 0.263 mmol) using general method 3. HPLC: >98% [t$_R$=4.2 min, 50% MeOH, 50% water (with 0.1% TFA), 20 min]. ¹H NMR (500 MHz, DMSO-d₆) δ 12.82 (s, 1H), 8.18 (d, J=8.4 Hz, 1H), 7.81-7.68 (m, 2H), 7.44 (d, J=8.2 Hz, 2H), 7.35-7.24 (m, 1H), 7.15-7.03 (m, 2H), 7.03-6.92 (m, 1H), 4.60-4.42 (m, 1H), 4.33-4.16 (m, 1H), 3.83-3.61 (m, 1H), 3.18 (dd, J=13.7, 4.7 Hz, 1H), 2.90 (dd, J=13.8, 10.5 Hz, 1H), 2.88-2.75 (m, 4H), 2.68-2.54 (m, 2H), 2.48-2.35 (m, 1H), 2.00-1.81 (m, 2H), 1.81-1.59 (m, 1H), 1.54-1.40 (m, 1H), 1.40-1.17 (m, 1H), 0.94-0.68 (m, 2H); ¹⁹F NMR (471 MHz, DMSO-d₆) δ −113.9 (m). HRMS (EST+): m/z C₂₆H₂₉FN₃O₄(M+H)⁺ 466.2131; m/z C₂₆H₂₈FN₃O₄Na (M+Na)⁺ 488.1958; HPLC-MS (ESI+): m/z 466.2 [100%, (M+H)⁺], (ESI−): m/z 464.2 [50%, (M−H)⁻].

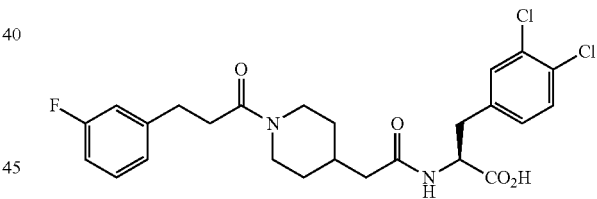

Example 45. (S)-3-(3,4-Dichlorophenyl)-2-(2-(1-(3-(3-fluorophenyl)propanoyl)piperidin-4-yl)acetamido)propanoic acid (SR5-033)

SR5-033 was obtained as a white foam (0.114 g, 96%) from SR5-022 (0.121 g, 0.231 mmol) using general method 3. HPLC: >98% [t$_R$=6.8 min, 70% MeOH, 30% water (with 0.1% TFA), 20 min]. ¹H NMR (500 MHz, DMSO-d₆) δ 12.79 (s, 1H), 8.16 (dd, J=8.6, 2.4 Hz, 1H), 7.59-7.46 (m, 2H), 7.36-7.28 (m, 1H), 7.24 (ddd, J=8.3, 3.5, 2.0 Hz, 1H), 7.13-7.04 (m, 2H), 7.04-6.95 (m, 1H), 4.55-4.45 (m, 1H), 4.33-4.22 (m, 1H), 3.83-3.66 (m, 1H), 3.11 (dt, J=13.8, 4.0 Hz, 1H), 2.90-2.75 (m, 4H), 2.67-2.56 (m, 2H), 2.48-2.35 (m, 1H), 2.01-1.89 (m, 2H), 1.80-1.60 (m, 1H), 1.51-1.41 (m, 1H), 1.33-1.15 (m, 1H), 0.96-0.68 (m, 2H); ¹⁹F NMR (471 MHz, DMSO-d₆) δ −113 (m). HRMS (ESI+): m/z C₂₅H₂₈Cl₂FN₂O₄(M−H)⁻ 507.1255; m/z C₂₅H₂₇Cl₂FN₂O₄Na (M+Na)⁺531.1230; HPLC-MS (ESI+): m/z 509.2 [100%, (M+H)⁺], (ESI−): m/z 507.2 [70%, (M−H)⁻].

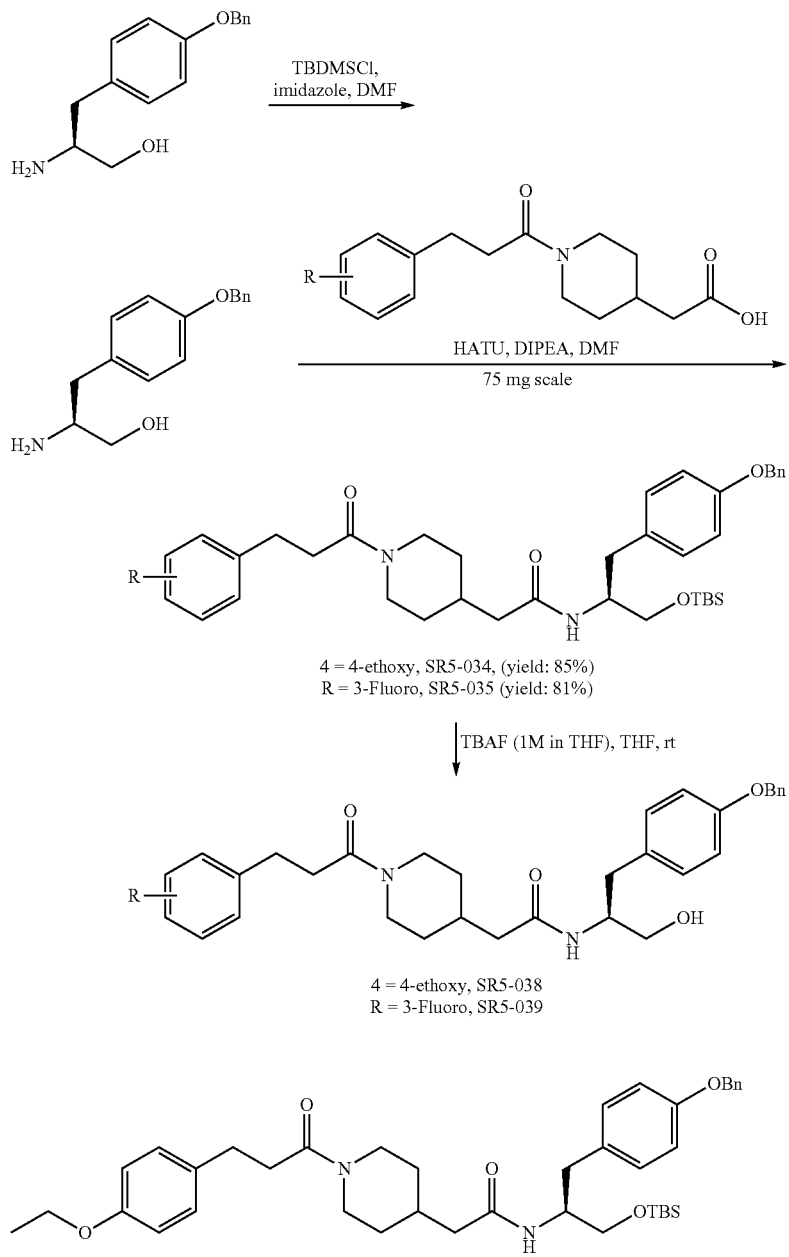

Example 46. (S)—N-(1-(4-(benzyloxy)phenyl)-3-((tert-butyldimethylsilyl)oxy)propan-2-yl)-2-(1-(3-(4-ethoxyphenyl)propanoyl)piperidin-4-yl)acetamide (SR5-034)

SR5-034 was prepared (0.135 g, 85%) from 2-(1-(3-(4-ethoxyphenyl)propanoyl)piperidin-4-yl)acetic acid (0.075 g, 0.235 mmol) and (S)-1-(4-(benzyloxy)phenyl)-3-((tert-butyldimethylsilyl)oxy)propan-2-amine (0.105 g, 0.282 mmol) by following the general method 4. $^1$H NMR (500 MHz, DMSO-$d_6$) δ 7.56 (d, J=8.5 Hz, 1H), 7.46-7.25 (m, 5H), 7.12-7.04 (m, 4H), 6.87 (d, J=8.2 Hz, 2H), 6.77 (dd, J=8.3, 4.7 Hz, 2H), 5.02 (s, 1H), 4.99 (s, 1H, rotamer), 4.29-4.18 (m, 1H), 3.98-3.83 (m, 3H), 3.73-3.60 (m, 1H), 3.49-3.38 (m, 2H), 2.86-2.73 (m, 2H), 2.73-2.63 (m, 3H), 2.46-2.29 (m, 3H), 1.87 (d, J=7.3 Hz, 2H), 1.75-1.63 (m, 1H), 1.50-1.37 (m, 1H), 1.34-1.20 (m, 4H), 0.85 (s, 9H), 0.83-0.66 (m, 2H), 0.00 (d, J=3.2 Hz, 6H). HRMS (ESI+): m/z $C_{40}H_{57}N_2O_5Si$ (M+H)$^+$ 673.4047; m/z $C_{40}H_{56}N_2O_5Si$ Na (M+Na)$^+$ 695.3856; HPLC-MS (ESI+): m/z 673.4 [80% (M+H)$^+$], m/z 695.4 [40%, (M+Na)$^+$].

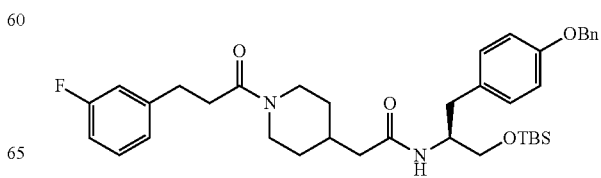

Example 47. (S)—N-(1-(4-(benzyloxy)phenyl)-3-((tert-butyldimethylsilyl)oxy)propan-2-yl)-2-(1-(3-(3-fluorophenyl)propanoyl)piperidin-4-yl)acetamide (SR5-035)

SR5-035 was prepared (0.133 g, 881%) from 2-(1-(3-(3-fluorophenyl)propanoyl)piperidin-4-yl)acetic acid (0.075 g, 0.255 mmol) and (S)-1-(4-(benzyloxy)phenyl)-3-((tert-butyldimethylsilyl)oxy)propan-2-amine (0.1145 g, 0.306 mmol) by following the general method 4. $^1$H NMR (500 MHz, DMSO-$d_6$) δ 7.59 (d, J=8.4 Hz, 1H), 7.49-7.33 (m, 4H), 7.34-7.24 (m, 2H), 7.15-7.03 (m, 4H), 7.03-6.94 (m, 1H), 6.90 (d, J=8.5 Hz, 2H), 5.05 (s, 1H), 5.03 (s, 1H, rotamer), 4.33-4.23 (m, 1H), 3.98-3.85 (m, 1H), 3.79-3.66 (m, 1H), 3.54-3.39 (m, 2H), 2.90-2.75 (m, 4H), 2.65-2.52 (m, 2H), 2.47-2.32 (m, 2H), 1.97-1.83 (m, 2H), 1.81-1.64 (m, 1H), 1.56-1.40 (m, 1H), 1.40-1.22 (m, 1H), 0.87 (s, 9H), 0.81 (m, 2H), 0.00 (s, 6H); $^{19}$F NMR (471 MHz, DMSO-$d_6$) δ −113.9 (m). HRMS (ESI+): m/z $C_{38}H_{52}FN_2O_4Si$ (M+H)$^+$ 647.3672; m/z $C_{38}H_{51}FN_2O_4Si$ Na (M+Na)$^+$ 669.3490; HPLC-MS (ESI+): m/z 647.4 [100% (M+H)$^+$], m/z 669.2 [40%, (M+Na)$^+$].

Example 48. (S)—N-(1-(4-(benzyloxy)phenyl)-3-hydroxypropan-2-yl)-2-(1-(3-(4-ethoxyphenyl)propanoyl)piperidin-4-yl)acetamide (SR5-038)

SR5-034 (0.116 g, 0.172 mmol) was dissolved in THF (2 mL) and 1M solution of TBAF in THF (0.344 mL, 0.344 mmol) added. The mixture was stirred for 6 h at rt and concentrated under reduced pressure. The resulting residue was dissolved in EtOAc (30 mL) and washed with sat. NH$_4$Cl (1×20 mL). The organic layer was dried (Na$_2$SO$_4$) and evaporated. Purification by flash column chromatography using MeOH/DCM (0:100-10:90) as eluent afforded the corresponding C-terminal alcohol product (0.081 g, 84%). HPLC: >97% [t$_R$=10.5 min, 50% MeOH, 50% water (with 0.1% TFA), 20 min]. $^1$H NMR (500 MHz, DMSO-$d_6$) δ 7.58 (d, J=8.5 Hz, 1H), 7.51-7.29 (m, 5H), 7.16-7.04 (m, 4H), 6.89 (d, J=8.3 Hz, 2H), 6.86-6.76 (m, 2H), 5.05 (s, 1H), 5.03 (s, 1H, rotamer), 4.74 (t, J=5.5 Hz, 1H), 4.33-4.23 (m, 1H), 4.02-3.93 (m, 2H), 3.93-3.85 (m, 1H), 3.78-3.64 (m, 1H), 3.39-3.33 (m, 1H), 3.30-3.24 (m, 1H), 2.90-2.75 (m, 2H), 2.75-2.66 (m, 2H), 2.57-2.52 (m, 3H), 2.50-2.45 (m, 1H), 2.45-2.36 (m, 1H), 1.90 (dd, J=7.3, 2.8 Hz, 2H), 1.77-1.67 (m, 1H), 1.52-1.40 (m, 1H), 1.35-1.22 (m, 4H), 0.98-0.72 (m, 2H). HRMS (ESI+): m/z $C_{34}H_{43}N_2O_5$ (M+H)$^+$ 559.3159; m/z $C_{34}H_{42}N_2O_5Na$ (M+Na)$^+$ 581.2977; HPLC-MS (ESI+): m/z 559.2 [100% (M+H)$^+$], m/z 581.2 [50%, (M+Na)$^+$].

Example 49. (S)—N-(1-(4-(Benzyloxy)phenyl)-3-hydroxypropan-2-yl)-2-(1-(3-(3-fluorophenyl)propanoyl)piperidin-4-yl)acetamide (SR5-039)

SR5-039 (0.084 g, 90%) was prepared from compound SR5-035 (0.113 g, 0.175 mmol) using the same method reported in preparation of SR5-038. HPLC: >98% [t$_R$=8.5 min, 50% MeOH, 50% water (with 0.1% TFA), 20 min]. $^1$H NMR (500 MHz, DMSO-$d_6$) δ 7.58 (d, J=8.6 Hz, 1H), 7.47-7.35 (m, 3H), 7.34-7.26 (m, 2H), 7.11 (d, J=8.6 Hz, 2H), 7.09-7.05 (m, 2H), 7.04-6.95 (m, 1H), 6.90 (d, J=8.6 Hz, 2H), 5.05 (s, 1H), 5.03 (s, 1H, rotamer), 4.73 (t, J=5.5 Hz, 1H), 4.32-4.23 (m, 1H), 3.98-3.84 (m, 1H), 3.84-3.65 (m, 1H), 3.35 (m, 1H), 3.27 (m, 1H), 2.90-2.75 (m, 4H), 2.66-2.53 (m, 2H), 2.48-2.30 (m, 2H), 1.90 (dd, J=7.2, 2.0 Hz, 2H), 1.78-1.66 (m, 1H), 1.52-1.41 (m, 1H), 1.36-1.20 (m, 1H), 0.94-0.70 (m, 2H); $^{19}$F NMR (471 MHz, DMSO-$d_6$) δ −113.9 (m). HRMS (ESI+): m/z $C_{32}H_{38}N_2O_4$ (M+H)$^+$ 533.2812; m/z $C_{32}H_{37}N_2O_4Na$ (M+Na)$^+$ 555.2621; HPLC-MS (ESI+): m/z 533.2 [100% (M+H)$^+$], m/z 555.2 [30%, (M+Na)$^+$].

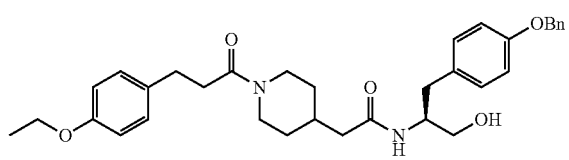 [SMILES: CCOc1ccc(CCC(=O)N2CCC(CC(=O)N[C@H](CO)Cc3ccc(OCc4ccccc4)cc3)CC2)cc1]

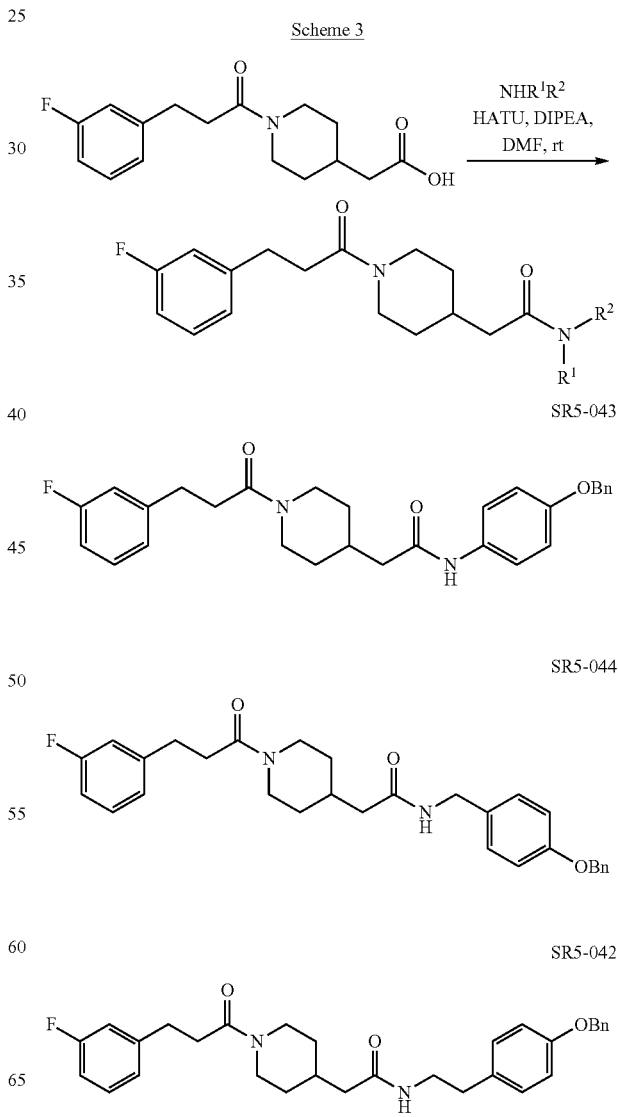

Scheme 3

-continued

SR5-040
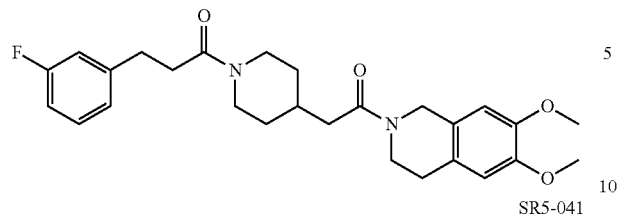

SR5-041
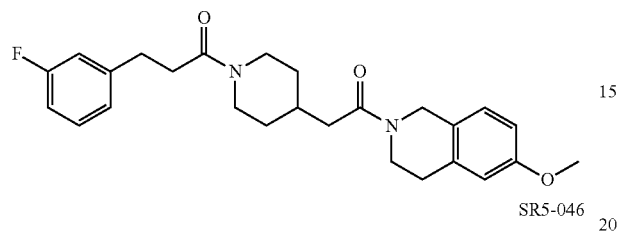

SR5-046
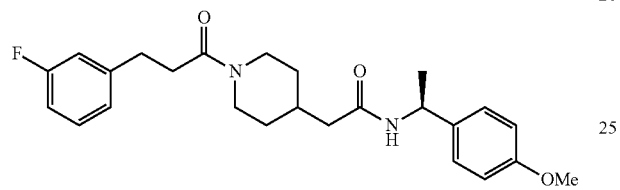

SR5-047
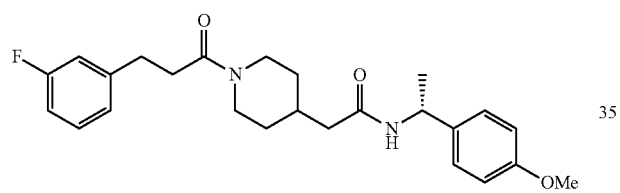

SR5-048
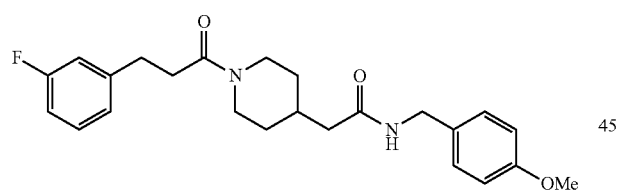

SR5-049
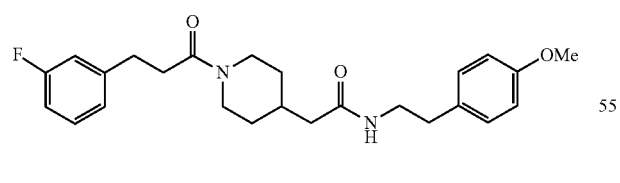

SR5-050
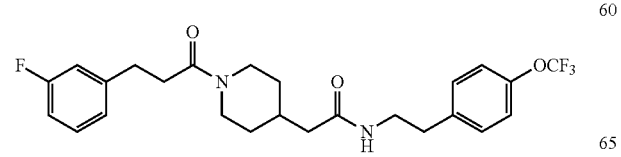

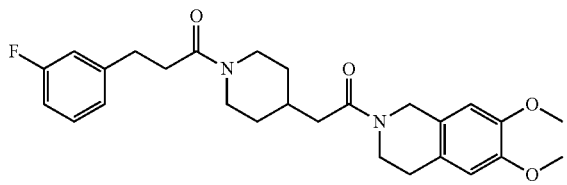 [SMILES: COc1cc2c(cc1OC)CN(C(=O)CC1CCN(C(=O)CCc3cccc(F)c3)CC1)CC2]

Example 50. 1-(4-(2-(6,7-Dimethoxy-3,4-dihydroisoquinolin-2(1H)-yl)-2-oxoethyl)piperidin-1-yl)-3-(3-fluorophenyl)propan-1-one (SR5-040)

SR5-040 (0.076 g, 95%) was prepared from 2-(1-(3-(3-fluorophenyl)propanoyl)piperidin-4-yl)acetic acid (0.050 g, 0.170 mmol) and 6,7-dimethyl-1,2,3,4-tetrahydroisoquinoline (0.047 g, 0.204 mmol) using the general method 4. HPLC: >98% [$t_R$=7.8 min, 60% MeOH, 40% water (with 0.1% TFA), 20 min]. $^1$H NMR (500 MHz, DMSO-$d_6$) δ 7.37-7.26 (m, 1H), 7.13-7.06 (m, 2H), 7.04-6.96 (m, 1H), 6.78 (d, J=2.7 Hz, 1H), 6.74 (d, J=3.8 Hz, 1H), 4.56 (s, 1H), 4.52 (s, 1H), 4.42-4.29 (m, 1H), 3.90-3.79 (m, 1H), 3.78-3.69 (m, 6H), 3.69-3.58 (m, 2H), 3.00-2.87 (m, 1H), 2.82 (t, J=7.6 Hz, 2H), 2.75 (t, J=5.8 Hz, 1H), 2.69-2.57 (m, 3H), 2.53-0.2.49 (m, 1H), 2.31 (d, J=6.8 Hz, 2H), 2.01-1.88 (m, 1H), 1.72-1.61 (m, 2H), 1.10-0.89 (m, 2H); $^{19}$F NMR (471 MHz, DMSO-$d_6$) δ −113.8-−113.9 (m). HRMS (ESI+): m/z $C_{27}H_{35}FN_2O_4$(M+H)$^+$ 469.2498; m/z $C_{27}H_{34}FN_2O_4Na$ (M+Na)$^+$ 491.2312; HPLC-MS (ESI+): m/z 469.4 [100% (M+H)$^+$], m/z 491.2 [40%, (M+Na)$^+$].

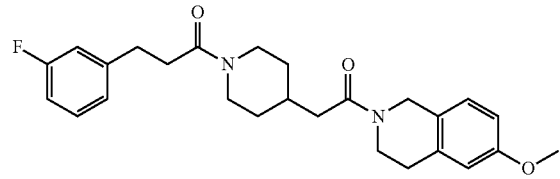 [SMILES: COc1ccc2c(c1)CCN(C(=O)CC1CCN(C(=O)CCc3cccc(F)c3)CC1)C2]

Example 51. 3-(3-Fluorophenyl)-1-(4-(2-(6-methoxy-3,4-dihydroisoquinolin-2(1H)-yl)-2-oxoethyl)piperidin-1-yl)propan-1-one (SR5-041)

SR5-041 (0.072 g, 96%) was prepared from 2-(1-(3-(3-fluorophenyl)propanoyl)piperidin-4-yl)acetic acid (0.050 g, 0.170 mmol) and 6-methyl-1,2,3,4-tetrahydroisoquinoline (0.041 g, 0.204 mmol) using the general method 4. HPLC: >97% [$t_R$=7.7 min, 65% MeOH, 35% water (with 0.1% TFA), 20 min]. $^1$H NMR (500 MHz, DMSO-$d_6$) δ 7.36-7.26 (m, 1H), 7.16-7.06 (m, 3H), 7.05-6.95 (m, 1H), 6.83-6.71 (m, 2H), 4.65 (s, 1H), 4.55 (m, 1H), 4.41-4.27 (m, 1H), 3.89-3.78 (m, 1H), 3.72 (s, 3H), 3.64 (t, J=6.0 Hz, 2H), 3.02-2.87 (m, 2H), 2.82 (t, J=7.6 Hz, 3H), 2.78-2.68 (m, 1H), 2.67-2.57 (m, 2H), 2.31 (dd, J=6.9, 4.0 Hz, 2H), 2.03-1.86 (m, 1H), 1.73-1.61 (m, 2H), 1.09-0.87 (m, 2H); $^{19}$F NMR (471 MHz, DMSO-$d_6$) δ −113.9 (m). HRMS (ESI+): m/z $C_{26}H_{32}FN_2O_3$(M+H)$^+$ 439.2389; m/z $C_{26}H_{31}FN_2O_3Na$ (M+Na)$^+$ 461.2209; HPLC-MS (ESI+): m/z 439.2 [100% (M+H)$^+$], m/z 461.2 [30%, (M+Na)$^+$].

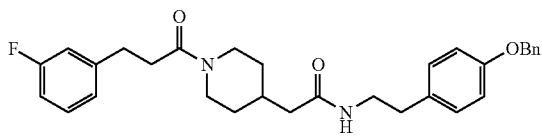 [SMILES: O=C(CC1CCN(C(=O)CCc2cccc(F)c2)CC1)NCCc1ccc(OCc2ccccc2)cc1]

Example 52. N-(4-(Benzyloxy)phenethyl)-2-(1-(3-(3-fluorophenyl)propanoyl)piperidin-4-yl)acetamide (SR5-042)

SR5-042 (0.081 g, 94%) was prepared from 2-(1-(3-(3-fluorophenyl)propanoyl)piperidin-4-yl)acetic acid (0.050 g, 0.170 mmol) and 2(4-benzyloxyphenyl)-ethylamine·HCl (0.054 g, 0.204 mmol) using the general method 4. HPLC: >99% [$t_R$=5.3 min, 75% MeOH, 25% water (with 0.1% TFA), 20 min]. $^1$H NMR (500 MHz, DMSO-$d_6$) δ 7.83 (t, J=5.7 Hz, 1H), 7.47-7.41 (m, 2H), 7.41-7.35 (m, 2H), 7.35-7.26 (m, 2H), 7.11 (d, J=8.6 Hz, 2H), 7.09-7.06 (m, 2H), 7.03-6.96 (m, 1H), 6.92 (d, J=8.6 Hz, 2H), 5.06 (s, 2H), 4.38-4.27 (m, 1H), 3.85-3.76 (m, 1H), 3.23 (m, 2H), 2.96-2.86 (m, 1H), 2.82 (t, J=7.7 Hz, 3H), 2.67-2.55 (m, 3H), 2.49-2.42 (m, 1H), 1.94 (d, J=7.1 Hz, 2H), 1.86-1.78 (m, 1H), 1.58-1.46 (m, 2H), 1.00-0.79 (m, 2H); $^{19}$F NMR (471 MHz, DMSO-$d_6$) δ −113.9 (m). HRMS (ESI+): m/z $C_{31}H_{36}FN_2O_3$(M+H)$^+$503.2698; m/z $C_{31}H_{35}FN_2O_3$Na (M+Na)$^+$ 525.2517; HPLC-MS (ESI+): m/z 503.2 [100% (M+H)$^+$], m/z 525.2 [40%, (M+Na)$^+$].

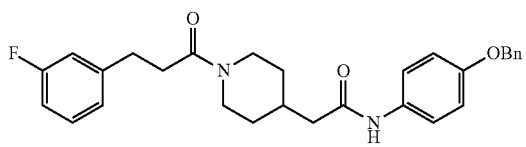 [SMILES: O=C(CC1CCN(C(=O)CCc2cccc(F)c2)CC1)Nc1ccc(OCc2ccccc2)cc1]

Example 53. N-(4-(Benzyloxy)phenyl)-2-(1-(3-(3-fluorophenyl)propanoyl)piperidin-4-yl)acetamide (SR5-043)

SR5-043 (0.077 g, 94%) was prepared from 2-(1-(3-(3-fluorophenyl)propanoyl)piperidin-4-yl)acetic acid (0.050 g, 0.170 mmol) and 2(4-benzyloxyaniline·HCl (0.048 g, 0.204 mmol) using the general method 4. HPLC: >99% [$t_R$=3.5 min, 55% MeOH, 45% water (with 0.1% TFA), 20 min]. $^1$H NMR (500 MHz, DMSO-$d_6$) δ 9.74 (s, 1H), 7.49 (d, J=9.0 Hz, 2H), 7.45-7.41 (m, 2H), 7.41-7.37 (m, 2H), 7.35-7.27 (m, 2H), 7.13-7.04 (m, 2H), 7.03-6.96 (m, 1H), 6.94 (d, J=9.0 Hz, 2H), 5.06 (s, 2H), 4.37 (m, 1H), 3.86 (m, 1H), 3.01-2.91 (m, 1H), 2.89-2.78 (m, 3H), 2.70-2.58 (m, 2H), 2.25-2.13 (m, 2H), 2.08-1.90 (m, 1H), 1.73-1.60 (m, 2H), 1.15-0.88 (m, 2H); $^{19}$F NMR (471 MHz, DMSO-$d_6$) δ −113.9 (m). HRMS (ESI+): m/z $C_{29}H_{32}FN_2O_3$(M+H)$^+$ 475.2387; m/z $C_{29}H_{31}FN_2O_3$Na (M+Na)$^+$ 497.2205; HPLC-MS (ESI+): m/z 475.3 [100% (M+H)$^+$], m/z 497.3 [60%, (M+Na)$^+$].

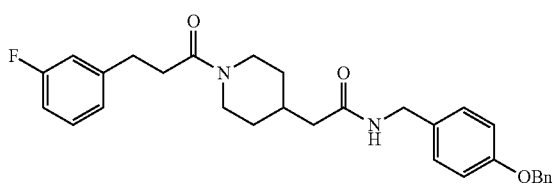 [SMILES: O=C(CC1CCN(C(=O)CCc2cccc(F)c2)CC1)NCc1ccc(OCc2ccccc2)cc1]

Example 54. N-(4-(Benzyloxy)benzyl)-2-(1-(3-(3-fluorophenyl)propanoyl)piperidin-4-yl)acetamide (SR5-044)

SR5-044 (0.073 g, 88%) was prepared from 2-(1-(3-(3-fluorophenyl)propanoyl)piperidin-4-yl)acetic acid (0.050 g, 0.170 mmol) and 2(4-benzyloxybenzylamine·HCl (0.044 g, 0.204 mmol) using the general method 4. HPLC: >96% [$t_R$=7.5 min, 70% MeOH, 30% water (with 0.1% TFA), 20 min]. $^1$H NMR (500 MHz, DMSO-$d_6$) δ 8.24 (t, J=5.9 Hz, 1H), 7.47-7.42 (m, 2H), 7.42-7.35 (m, 2H), 7.35-7.27 (m, 2H), 7.16 (d, J=8.7 Hz, 2H), 7.12-7.06 (m, 2H), 7.02-6.97 (m, 1H), 6.96 (d, J=8.6 Hz, 2H), 5.09 (s, 2H), 4.39-4.30 (m, 1H), 4.18 (d, J=5.9 Hz, 2H), 3.89-3.74 (m, 1H), 3.00-2.87 (m, 1H), 2.82 (t, J=7.7 Hz, 2H), 2.62 (m, 2H), 2.52-2.49 (m, 1H), 2.04 (d, J=7.1 Hz, 2H), 1.91 (m, 1H), 1.67-1.52 (m, 2H), 1.31-1.23 (m, 0.5H), 1.12 (m, 0.5H), 1.08-0.80 (m, 2H)$^{19}$F NMR (471 MHz, DMSO-$d_6$) δ −113.9 (m). HRMS (ESI+): m/z $C_{30}H_{34}FN_2O_3$(M+H)$^+$ 489.2544; m/z $C_{30}H_{33}FN_2O_3$Na (M+Na)$^+$ 511.2361; HPLC-MS (ESI+): m/z 489.2 [100% (M+H)$^+$], m/z 511.2 [90%, (M+Na)$^+$].

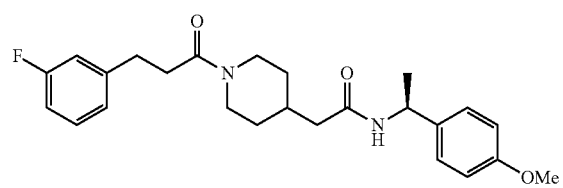 [SMILES: COc1ccc([C@H](C)NC(=O)CC2CCN(C(=O)CCc3cccc(F)c3)CC2)cc1]

Example 55. (S)-2-(1-(3-(3-Fluorophenyl)propanoyl)piperidin-4-yl)-N-(1-(4-methoxyphenyl)ethyl)acetamide (SR5-046)

SR5-046 (0.056 g, 97%) was prepared from 2-(1-(3-(3-fluorophenyl)propanoyl)piperidin-4-yl)acetic acid (0.040 g, 0.136 mmol) and (S)-(−)-1-(4-methoxyphenyl)ethylamine (0.025 mL, 0.164 mmol) using the general method 4. HPLC: >99% [$t_R$=6.0 min, 50% MeOH, 50% water (with 0.1% TFA), 20 min]. $^1$H NMR (500 MHz, DMSO-$d_6$) δ 8.17 (d, J=8.1 Hz, 1H), 7.35-7.27 (m, 1H), 7.21 (d, J=8.6 Hz, 2H), 7.14-7.05 (m, 2H), 7.04-6.96 (m, 1H), 6.87 (dd, J=8.8, 2.3 Hz, 2H), 4.93-4.82 (m, 1H), 4.39-4.26 (m, 1H), 3.86-3.77 (m, 1H), 3.73 (s, 3H), 2.98-2.86 (m, 1H), 2.82 (t, J=7.7 Hz, 2H), 2.67-2.57 (m, 2H), 2.55-2.52 (m, 1H), 2.02 (d, J=7.1 Hz, 2H), 1.96-1.80 (m, 1H), 1.65-1.48 (m, 2H), 1.30 (d, J=7.0 Hz, 3H), 0.94 (m, 2H); $^{19}$F NMR (471 MHz, DMSO-$d_6$) δ −113.93 (m). HRMS (ESI+): m/z $C_{25}H_{32}FN_2O_3$(M+H)$^+$ 427.2387; m/z $C_{25}H_{31}FN_2O_3$Na (M+Na)$^+$ 449.2206; HPLC-MS (ESI+): m/z 427.2 [100% (M+H)$^+$], m/z 449.2 [90%, (M+Na)$^+$].

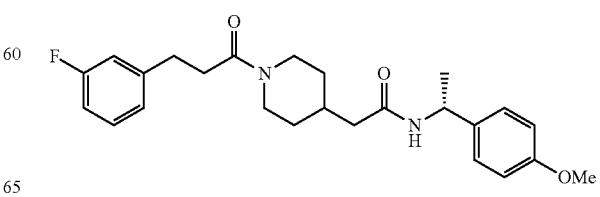

Example 56. (R)-2-(1-(3-(3-Fluorophenyl)propanoyl)piperidin-4-yl)-N-(1-(4-methoxyphenyl)ethyl)acetamide (SR5-047)

SR5-047 (0.053 g, 91%) was prepared from 2-(1-(3-(3-fluorophenyl)propanoyl)piperidin-4-yl)acetic acid (0.040 g, 0.136 mmol) and (R)-(+)-1-(4-methoxyphenyl)ethylamine (0.025 mL, 0.164 mmol) using the general method 4. HPLC: >99% [$t_R$=6.6 min, 50% MeOH, 50% water (with 0.1% TFA), 20 min]. $^1$H NMR (500 MHz, DMSO-$d_6$) δ 8.17 (d, J=8.1 Hz, 1H), 7.35-7.27 (m, 1H), 7.21 (d, J=8.6 Hz, 2H), 7.14-7.05 (m, 2H), 7.04-6.96 (m, 1H), 6.87 (dd, J=8.8, 2.3 Hz, 2H), 4.93-4.82 (m, 1H), 4.39-4.26 (m, 1H), 3.86-3.77 (m, 1H), 3.73 (s, 3H), 2.98-2.86 (m, 1H), 2.82 (t, J=7.7 Hz, 2H), 2.67-2.57 (m, 2H), 2.55-2.52 (m, 1H), 2.02 (d, J=7.1 Hz, 2H), 1.96-1.80 (m, 1H), 1.65-1.48 (m, 2H), 1.30 (d, J=7.0 Hz, 3H), 0.94 (m, 2H); $^{19}$F NMR (471 MHz, DMSO-$d_6$) δ −113.93 (m). HRMS (ESI+): m/z $C_{25}H_{32}FN_2O_3$(M+H)$^+$ 427.2386; m/z $C_{25}H_{31}FN_2O_3Na$ (M+Na)$^+$ 449.2205; HPLC-MS (ESI+): m/z 427.2 [90% (M+H)$^+$], m/z 449.2 [100%, (M+Na)$^+$].

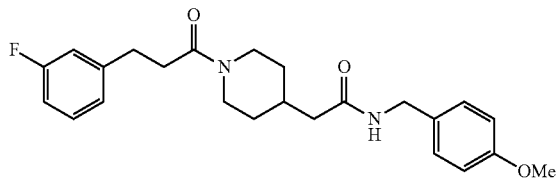 [SMILES: COc1ccc(CNC(=O)CC2CCN(C(=O)CCc3cccc(F)c3)CC2)cc1]

Example 57. 2-(1-(3-(3-Fluorophenyl)propanoyl)piperidin-4-yl)-N-(4-methoxybenzyl)acetamide (SR5-048)

SR5-048 (0.051 g, 91%) was prepared from 2-(1-(3-(3-fluorophenyl)propanoyl)piperidin-4-yl)acetic acid (0.040 g, 0.136 mmol) and 4-methoxybenzylamine (0.023 mL, 0.164 mmol) using the general method 4. HPLC: >99% [$t_R$=4.4 min, 50% MeOH, 50% water (with 0.1% TFA), 20 min]. $^1$H NMR (500 MHz, DMSO-$d_6$) δ 8.25 (t, J=5.9 Hz, 1H), 7.35-7.26 (m, 1H), 7.16 (d, J=8.6 Hz, 2H), 7.14-7.06 (m, 2H), 7.03-6.96 (m, 1H), 6.88 (d, J=8.6 Hz, 2H), 4.38-4.30 (m, 1H), 4.19 (d, J=5.9 Hz, 2H), 3.89-3.78 (m, 1H), 3.73 (s, 3H), 2.99-2.87 (m, 1H), 2.82 (t, J=7.7 Hz, 2H), 2.62 (m, 2H), 2.51 (m, 9H), 2.04 (d, J=7.1 Hz, 2H), 1.97-1.85 (m, 1H), 1.65-1.56 (m, 2H), 1.06-0.86 (m, 2H); $^{19}$F NMR (471 MHz, DMSO-$d_6$) δ −113.93 (m). HRMS (ESI+): m/z $C_{24}H_{30}FN_2O_3$(M+H)$^+$ 413.2187; m/z $C_{24}H_{29}FN_2O_3Na$ (M+Na)$^+$ 435.2005; HPLC-MS (ESI+): m/z 413.4 [100% (M+H)$^+$], m/z 435.2 [40%, (M+Na)$^+$].

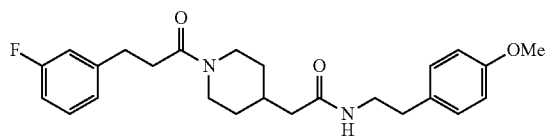 [SMILES: COc1ccc(CCNC(=O)CC2CCN(C(=O)CCc3cccc(F)c3)CC2)cc1]

Example 58. 2-(1-(3-(3-Fluorophenyl)propanoyl)piperidin-4-yl)-N-(4-methoxyphenethyl)acetamide (SR5-049)

SR5-049 (0.054 g, 93%) was prepared from 2-(1-(3-(3-fluorophenyl)propanoyl)piperidin-4-yl)acetic acid (0.040 g, 0.136 mmol) and 2-(4-methoxyphenyl)ethylamine (0.025 g, 0.164 mmol) using the general method 4. HPLC: >98% [$t_R$=6.4 min, 50% MeOH, 50% water (with 0.1% TFA), 20 min]. $^1$H NMR (500 MHz, DMSO-$d_6$) δ 7.82 (t, J=5.6 Hz, 1H), 7.35-7.27 (m, 1H), 7.15-7.05 (m, 4H), 7.05-6.94 (m, 1H), 6.84 (d, J=8.6 Hz, 2H), 4.38-4.26 (m, 1H), 3.85-3.76 (m, 1H), 3.71 (s, 3H), 3.28-3.19 (m, 2H), 2.96-2.85 (m, 1H), 2.84-2.79 (m, 2H), 2.67-2.57 (m, 4H), 2.49-2.44 (m, 1H), 1.95 (d, J=7.1 Hz, 2H), 1.88-1.75 (m, 1H), 1.59-1.46 (m, 2H), 1.01-0.80 (m, 2H); $^{19}$F NMR (471 MHz, DMSO-$d_6$) δ −113.9 (m). HRMS (ESI+): m/z $C_{25}H_{32}FN_2O_3$(M+H)$^+$ 427.2387; m/z $C_{25}H_{31}FN_2O_3Na$ (M+Na)$^+$ 449.2205; HPLC-MS (ESI+): m/z 427.2 [100% (M+H)$^+$], m/z 449.2 [50%, (M+Na)$^+$].

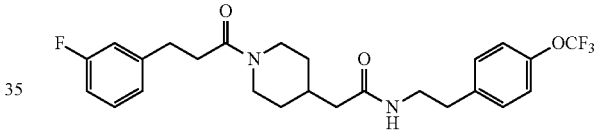

Example 59. 2-(1-(3-(3-Fluorophenyl)propanoyl)piperidin-4-yl)-N-(4-(trifluoromethoxy)phenethyl)acetamide (SR5-050)

SR5-050 (0.059 g, 90%) was prepared from 2-(1-(3-(3-fluorophenyl)propanoyl)piperidin-4-yl)acetic acid (0.040 g, 0.136 mmol) and 2-(4-(trifluoromethoxy)phenyl)ethylamine (0.034 g, 0.164 mmol) using the general method 4. HPLC: >96% [$t_R$=13.8 min, 30% MeOH, 70% water (with 0.1% TFA), 20 min]. $^1$H NMR (500 MHz, DMSO-$d_6$) δ 7.87 (t, J=5.6 Hz, 1H), 7.34-7.23 (m, 5H), 7.16-7.05 (m, 2H), 7.05-6.95 (m, 1H), 4.35-4.27 (m, 1H), 3.84-3.74 (m, 1H), 3.31-3.25 (m, 2H), 2.89 (m, 1H), 2.82 (t, J=7.6 Hz, 2H), 2.74 (t, J=7.1 Hz, 2H), 2.61 (m, 2H), 2.49-2.43 (m, 1H), 1.94 (d, J=7.1 Hz, 2H), 1.88-1.76 (m, 1H), 1.55-1.46 (m, 2H), 0.99-0.81 (m, 2H); $^{19}$F NMR (471 MHz, DMSO-$d_6$) δ −56.8, −113.9 (m). HRMS (ESI+): m/z $C_{25}H_{29}F_4N_2O_3$(M+H)$^+$ 481.2104; m/z $C_{25}H_{28}F_4N_2O_3Na$ (M+Na)$^+$ 503.1923; HPLC-MS (ESI+): m/z 481.2 [100% (M+H)$^+$], m/z 503.2 [30%, (M+Na)$^+$].

Scheme 4

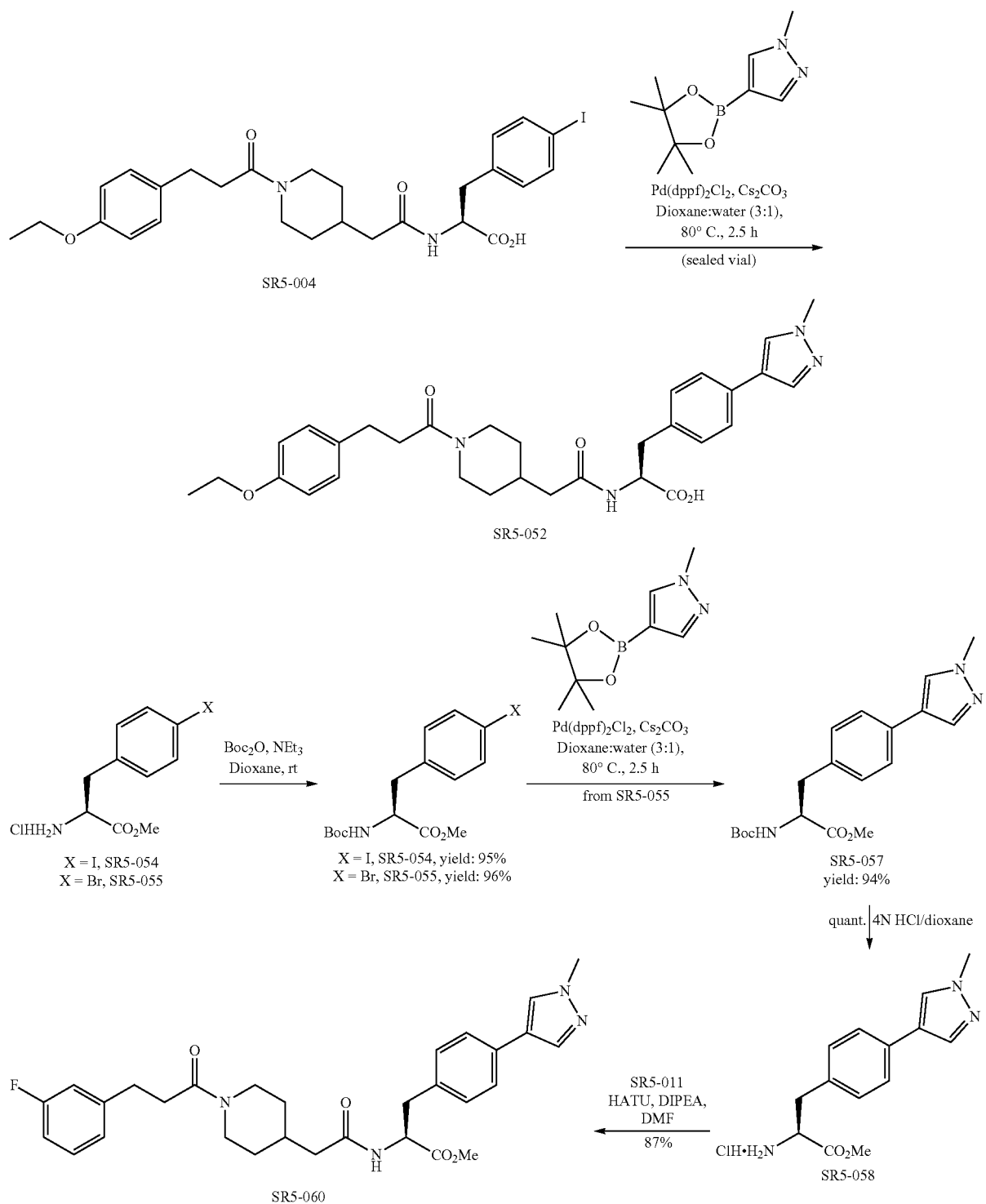

General Method 5 for Suzuki Coupling Reaction

Corresponding bromo- or iodophenyl derivative (1 eq.) was dissolved in a mixture of dioxane:water (3:1) and $Cs_2CO_3$ (3 eq.), boronic acid pinacol ester (1.3 eq.), and $Pd(dppf)Cl_2$ (5 mol %) were added. The mixture was heated at 80° C. in a sealed vial for 2 h with stirring. The mixture was diluted with EtOAc (25 mL) and washed with sat. $NH_4Cl$ (1×20 mL). The aqueous layer was extracted with EtOAc (2×20 mL) and the combined organic layer dried ($Na_2SO_4$) and evaporated under reduced pressure. Purification by flash column chromatography using MeOH/DCM (0:100-20:80) as eluent afforded the corresponding coupling product.

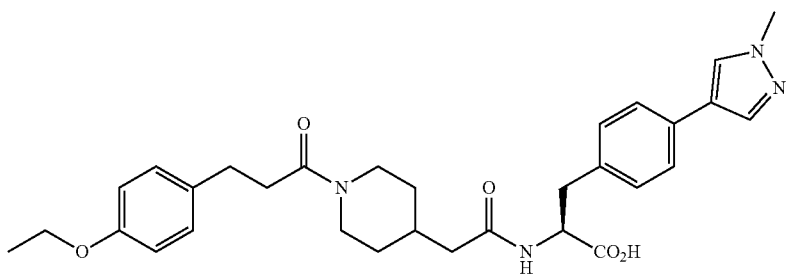 [SMILES: CCOc1ccc(CCC(=O)N2CCC(CC(=O)N[C@@H](Cc3ccc(-c4cnn(C)c4)cc3)C(=O)O)CC2)cc1]

Example 60. (S)-2-(2-(1-(3-(4-Ethoxyphenyl)propanoyl)piperidin-4-yl)acetamido)-3-(4-(1-methyl-1H-pyrazol-4-yl)phenyl)propanoic acid (SR5-052)

SR5-052 (0.014 g, 31%) was prepared from iodo derivative SR5-004 (0.050 g, 0.084 mmol) and (1-methylpyrazole-4-boronic acid pinacol ester (0.023 g, 0.109 mmol) using general method 5. HPLC: >98% [$t_R$=4.7 min, 50% MeOH, 50% water (with 0.1% TFA), 20 min]. $^1$H NMR (500 MHz, DMSO-$d_6$) δ 8.08 (s, 1H), 8.06-7.96 (m, 1H), 7.81 (d, J=4.5 Hz, 1H), 7.44 (d, J=7.7 Hz, 2H), 7.19 (d, J=8.0 Hz, 2H), 7.10 (d, J=8.4 Hz, 2H), 6.81 (dd, J=8.7, 2.7 Hz, 2H), 4.48-4.38 (m, 1H), 4.30-4.18 (m, 1H), 3.98 (q, J=7.0 Hz, 2H), 3.91-3.77 (m, 4H), 3.73-3.55 (m, 1H), 3.06 (dd, J=13.6, 4.2 Hz, 1H), 2.88-2.72 (m, 2H), 2.69 (t, J=7.7 Hz, 2H), 2.52 (m, 2H), 2.49-2.28 (m, -1H), 2.05-1.88 (m, 2H), 1.80-1.66 (m, 1H), 1.54-1.39 (m, 1H), 1.30 (t, J=6.9 Hz, 3H), 1.36-1.18 (m, 1H), 0.95-0.68 (m, 2H). HRMS (ESI+): m/z $C_{31}H_{39}N_4O_5$ (M+H)$^+$ 547.2913; m/z $C_{31}H_{38}N_4O_5Na$ (M+Na)$^+$ 569.2735; HPLC-MS (ESI+): m/z 547.2 [80%, (M+H)$^+$], (ESI−): m/z 545.2 [90%, (M−H)$^−$].

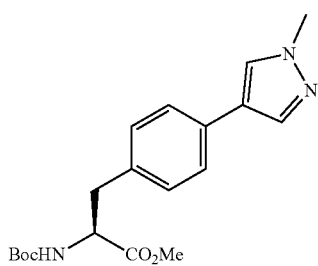 [SMILES: COC(=O)[C@H](Cc1ccc(-c2cnn(C)c2)cc1)NC(=O)OC(C)(C)C]

Example 61. Methyl (S)-2-((tert-butoxycarbonyl)amino)-3-(4-(1-methyl-1H-pyrazol-4-yl)phenyl)propanoate (SR5-057)

SR5-057 (0.284 g, 94%) was prepared from Boc-Phe(4-Br)—OMe (0.300 g, 0.837 mmol) and (1-methylpyrazole-4-boronic acid pinacol ester (0.209 g, 1.004 mmol) using general method 5.

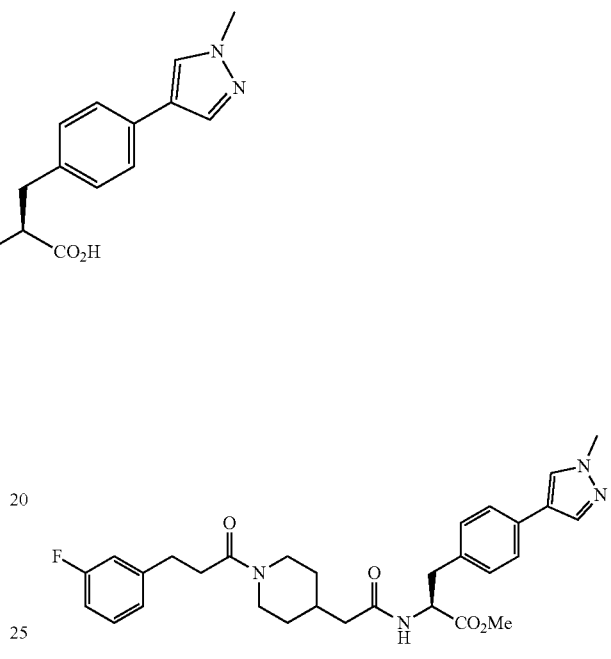

Example 62. Methyl (S)-2-(2-(1-(3-(3-fluorophenyl)propanoyl)piperidin-4-yl)acetamido)-3-(4-(1-methyl-1H-pyrazol-4-yl)phenyl)propanoate (SR5-060)

SR5-057 was dissolved in 4N HCl/dioxane (2.5 mL) and stirred for 2 h at rt. The mixture was concentrated and triturated with DCM/hexane to afford HCl salt SR5-058 (0.155 g, quant.). SR5-060 (0.157 g, 87%) was prepared from above HCl salt SR5-058 (0.050 g, 0.169 mmol) and 2-(1-(3-(3-fluorophenyl)propanoyl)piperidin-4-yl)acetic acid (0.050 g, 0.170 mmol) using general method 4. HPLC: >98% [$t_R$=5.1 min, 50% MeOH, 50% water (with 0.1% TFA), 20 min]. $^1$H NMR (500 MHz, DMSO-$d_6$) δ 8.27 (dd, J=8.1, 4.4 Hz, 1H), 8.08 (d, J=6.7 Hz, 1H), 7.82 (d, J=1.7 Hz, 1H), 7.46 (dd, J=8.2, 2.6 Hz, 2H), 7.38-7.25 (m, 1H), 7.19 (d, J=8.2 Hz, 2H), 7.12-7.04 (m, 2H), 7.00 (dd, J=9.9, 7.6 Hz, 1H), 4.58-4.47 (m, 1H), 4.31-4.20 (m, 1H), 3.83 (s, 3H), 3.63 (s, 3H), 3.11-2.97 (m, 1H), 2.67-2.60 (m, 4H), 2.59-2.53 (m, 2H), 2.48-2.33 (m, 1H), 2.03-1.85 (m, 2H), 1.78-1.69 (m, 1H), 1.51-1.40 (m, 1H), 1.40-1.17 (m, 1H), 0.94-0.69 (m, 2H); $^{19}$F NMR (471 MHz, DMSO-$d_6$) δ −113.9 (m). HRMS (ESI+): m/z $C_{30}H_{36}FN_4O_4$ (M+H)$^+$ 535.2705; m/z $C_{30}H_{35}FN_4O_4Na$ (M+Na)$^+$ 557.2530; HPLC-MS (ESI+): m/z 535.3 [80%, (M+H)$^+$], (ESI+): m/z 557.4 [40%, (M+Na)$^+$].

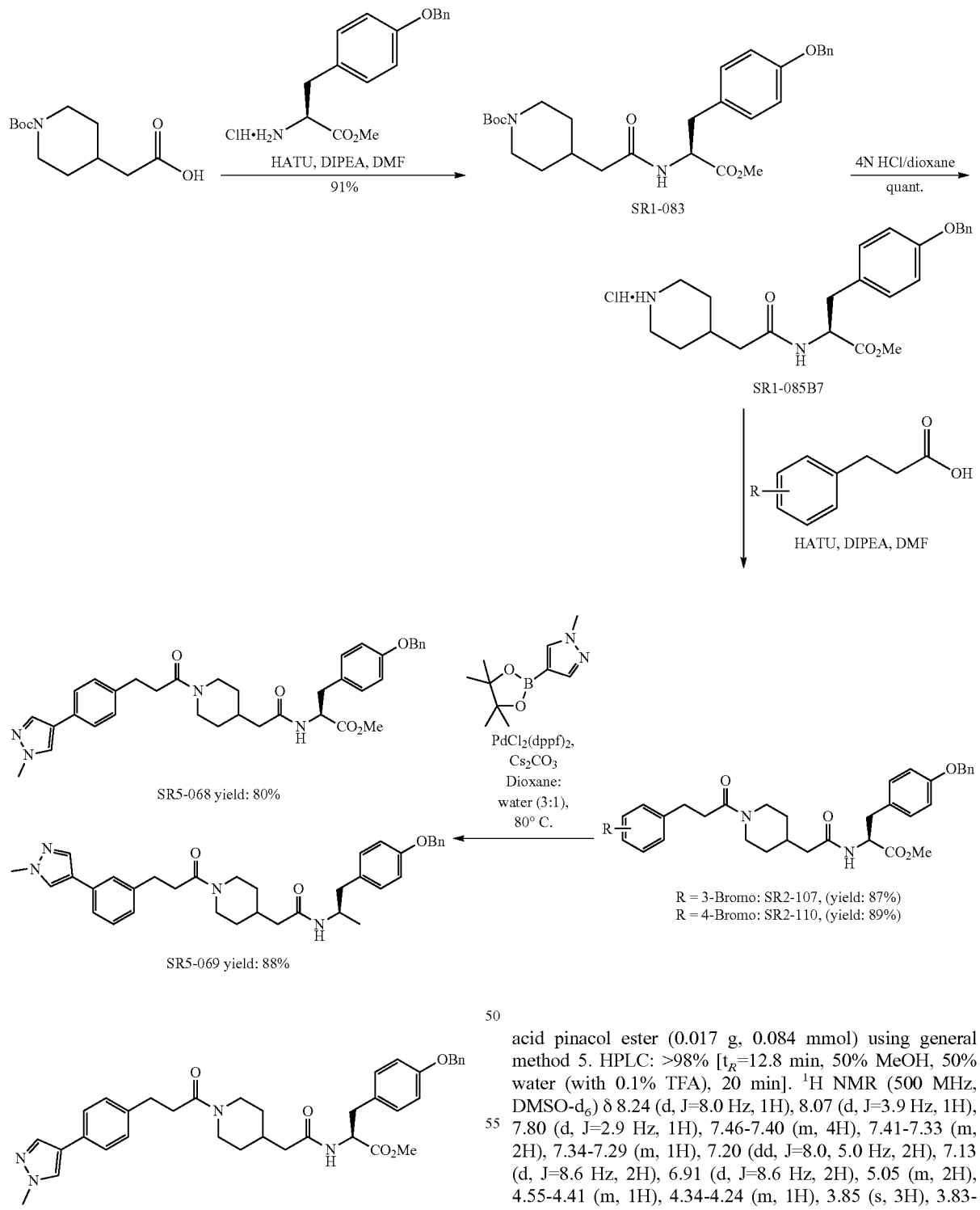

Scheme 5

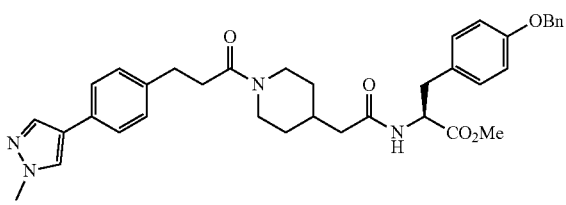 [SMILES: COC(=O)[C@H](Cc1ccc(OCc2ccccc2)cc1)NC(=O)CC1CCN(C(=O)CCc2ccc(-c3cnn(C)c3)cc2)CC1]

Example 63. Methyl (S)-3-(4-(Benzyloxy)phenyl)-2-(2-(1-(3-(4-(1-methyl-1H-pyrazol-4-yl)phenyl)propanoyl)piperidin-4-yl)acetamido)propanoate (SR5-068)

SR5-068 (0.040 g, 89%) was prepared from SR2-110 (0.045 g, 0.072 mmol) and (1-methylpyrazole-4-boronic acid pinacol ester (0.017 g, 0.084 mmol) using general method 5. HPLC: >98% [$t_R$=12.8 min, 50% MeOH, 50% water (with 0.1% TFA), 20 min]. $^1$H NMR (500 MHz, DMSO-$d_6$) δ 8.24 (d, J=8.0 Hz, 1H), 8.07 (d, J=3.9 Hz, 1H), 7.80 (d, J=2.9 Hz, 1H), 7.46-7.40 (m, 4H), 7.41-7.33 (m, 2H), 7.34-7.29 (m, 1H), 7.20 (dd, J=8.0, 5.0 Hz, 2H), 7.13 (d, J=8.6 Hz, 2H), 6.91 (d, J=8.6 Hz, 2H), 5.05 (m, 2H), 4.55-4.41 (m, 1H), 4.34-4.24 (m, 1H), 3.85 (s, 3H), 3.83-3.69 (m, 1H), 3.61 (s, 3H), 2.98 (dd, J=13.8, 5.1 Hz, 1H), 2.92-2.72 (m, 4H), 2.62-2.54 (m, 1H), 2.48-2.43 (m, 1H), 2.42 (m, 1H), 1.96 (d, J=7.3 Hz, 2H), 1.81-1.67 (m, 1H), 1.54-1.43 (m, 1H), 1.37-1.27 (m, 1H), 0.98-0.68 (m, 2H). HRMS (ESI+): m/z $C_{37}H_{43}N_4O_5$ (M+H)$^+$ 623.3215; m/z $C_{37}H_{42}N_4O_5Na$ (M+Na)$^+$ 645.3039; HPLC-MS (ESI+): m/z 623, 4 [100%, (M+H)$^+$], (ESI+): m/z 645.4 [30%, (M+Na)$^+$].

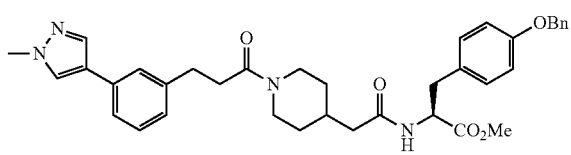 [SMILES: COC(=O)[C@H](Cc1ccc(OCc2ccccc2)cc1)NC(=O)CC1CCN(C(=O)CCc2cccc(-c3cnn(C)c3)c2)CC1]

Example 64. Methyl (S)-3-(4-(Benzyloxy)phenyl)-2-(2-(1-(3-(3-(1-methyl-1H-pyrazol-4-yl)phenyl)propanoyl)piperidin-4-yl)acetamido)propanoate (SR5-069)

SR5-069 (0.044 g, 88%) was prepared from SR2-107 (0.050 g, 0.080 mmol) and (1-methylpyrazole-4-boronic acid pinacol ester (0.020 g, 0.096 mmol) using general method 5. HPLC: >98% [$t_R$=5.0 min, 60% MeOH, 40% water (with 0.1% TFA), 20 min]. $^1$H NMR (500 MHz, DMSO-d$_6$) δ 8.24 (d, J=8.0 Hz, 1H), 8.09 (d, J=2.7 Hz, 1H), 7.83 (s, 1H), 7.49-7.29 (m, 7H), 7.29-7.18 (m, 1H), 7.13 (d, J=8.0 Hz, 2H), 7.08-6.98 (m, 1H), 6.91 (d, J=8.7 Hz, 2H), 5.05 (s, 2H), 4.56-4.37 (m, 1H), 4.37-4.20 (m, 1H), 3.86 (s, 3H), 3.83-3.71 (m, 1H), 3.60 (s, 3H), 2.98 (dd, J=13.8, 4.9 Hz, 1H), 2.93-2.71 (m, 4H), 2.67-2.54 (m, 2H), 2.49-2.36 (m, 1H), 1.96 (d, J=7.2 Hz, 2H), 1.80-1.66 (m, 1H), 1.54-1.41 (m, 1H), 1.39-1.27 (m, 1H), 1.01-0.71 (m, 2H). HRMS (ESI+): m/z C$_{37}$H$_{43}$N$_4$O$_5$ (M+H)$^+$ 623.3217; m/z C$_{37}$H$_{42}$N$_4$O$_5$Na (M+Na)$^+$ 645.3042; HPLC-MS (ESI+): m/z 623.4 [100%, (M+H)$^+$], (ESI+): m/z 645.2 [10%, (M+Na)$^+$].

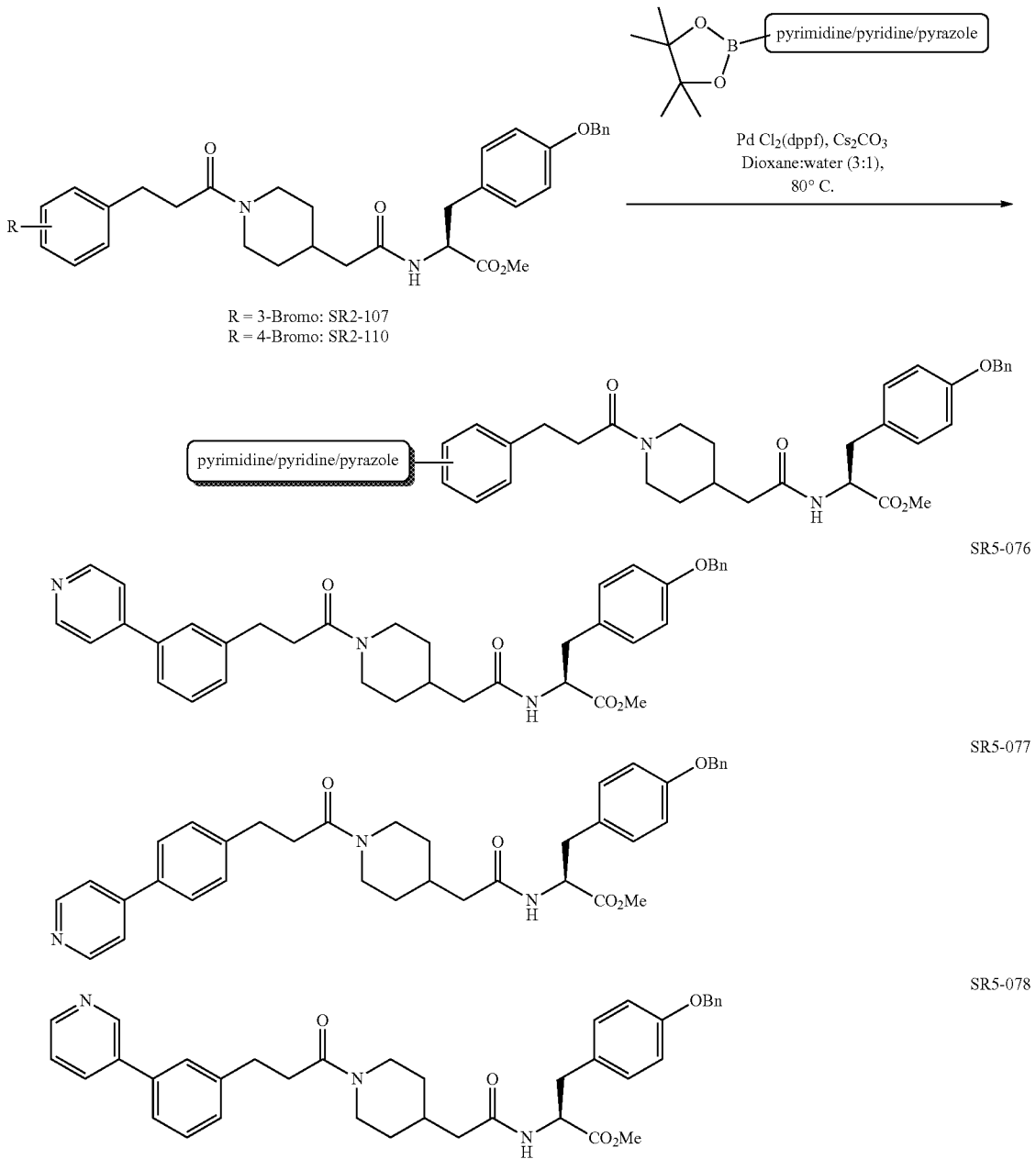

Scheme 6

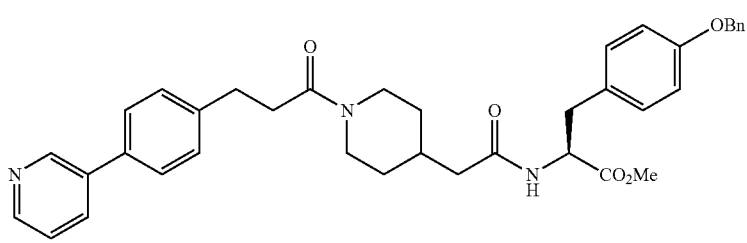

SR5-079

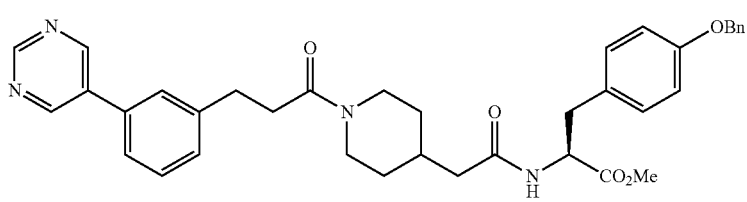

SR5-081

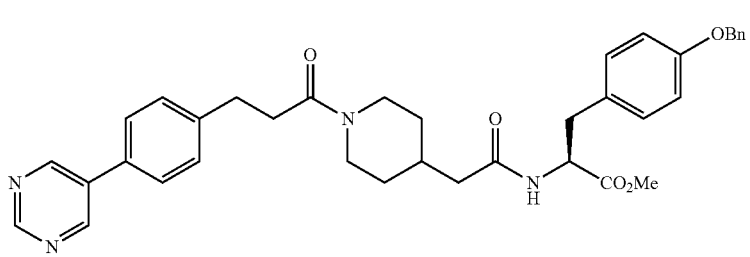

SR5-082

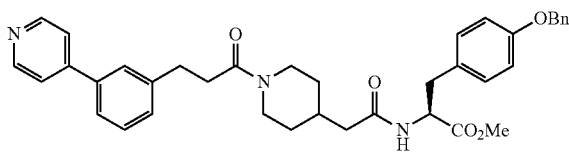 [SMILES: COC(=O)[C@H](Cc1ccc(OCc2ccccc2)cc1)NC(=O)CC1CCN(C(=O)CCc2cccc(-c3ccncc3)c2)CC1]

Example 65. Methyl (S)-3-(4-(Benzyloxy)phenyl)-2-(2-(1-(3-(3-(pyridin-4-yl)phenyl)propanoyl)piperidin-4-yl)acetamido)propanoate (SR5-076)

SR5-076 (0.038 g, 77%) was prepared from SR2-107 (0.050 g, 0.080 mmol) and pyridine-4-boronic acid pinacol ester (0.018 g, 0.088 mmol) using general method 5. HPLC: >98% [$t_R$=4.8 min, 50% MeOH, 50% water (with 0.1% TFA), 20 min]. $^1$H NMR (500 MHz, DMSO-$d_6$) δ 8.63 (m, 2H), 8.23 (d, J=8.0 Hz, 1H), 7.73-7.65 (m, 3H), 7.63-7.47 (m, 2H), 7.46-7.38 (m, 3H), 7.38-7.28 (m, 3H), 7.13 (d, J=8.4 Hz, 2H), 6.91 (d, J=8.6 Hz, 2H), 5.06 (s, 1H), 5.03 (s, 1H, rotamer), 4.51-4.40 (m, 1H), 4.37-4.25 (m, 1H), 3.86-3.70 (m, 1H), 3.60 (s, 3H), 2.98 (dd, J=13.8, 5.1 Hz, 1H), 2.95-2.75 (m, 4H), 2.69-2.56 (m, 2H), 2.50-2.33 (m, 1H), 1.96 (d, J=7.2 Hz, 2H), 1.83-1.66 (m, 1H), 1.51-1.44 (m, 1H), 1.37-1.21 (m, 1H), 1.00-0.71 (m, 2H). HRMS (ESI+): m/z $C_{38}H_{42}N_3O_5$ (M+H)$^+$ 620.3105; m/z $C_{38}H_{41}N_3O_5Na$ (M+Na)$^+$ 642.2936; HPLC-MS (ESI+): m/z 620.4 [100%, (M+H)$^+$], (ESI+): m/z 642.2 [10%, (M+Na)$^+$].

Example 66. Methyl (S)-3-(4-(Benzyloxy)phenyl)-2-(2-(1-(3-(4-(pyridin-4-yl)phenyl)propanoyl)piperidin-4-yl)acetamido)propanoate (SR5-077)

SR5-077 (0.039 g, 78%) was prepared from SR2-110 (0.050 g, 0.080 mmol) and pyridine-4-boronic acid pinacol ester (0.018 g, 0.088 mmol) using general method 5. HPLC: >98% [$t_R$=4.4 min, 50% MeOH, 50% water (with 0.1% TFA), 20 min]. $^1$H NMR (500 MHz, DMSO-$d_6$) δ 8.67-8.56 (m, 2H), 8.23 (d, J=8.0 Hz, 1H), 7.77-7.61 (m, 4H), 7.48-7.28 (m, 7H), 7.17-7.09 (m, 2H), 6.98-6.85 (m, 2H), 5.05 (s, 2H), 4.46 (m, 1H), 3.84-3.67 (m, 1H), 3.61 (s, 3H), 2.98 (dd, J=13.8, 5.1 Hz, 1H), 2.93-2.81 (m, 3H), 2.78 (dd, J=13.8, 10.1 Hz, 1H), 2.67-2.55 (m, 2H), 2.47-2.31 (m, −1H), 1.97 (d, J=7.3 Hz, 2H), 1.81-1.67 (m, 1H), 1.56-1.43 (m, 1H), 1.39-1.28 (m, 1H), 1.01-0.73 (m, 2H). HRMS (ESI+): m/z $C_{38}H_{42}N_3O_5$ (M+H)$^+$ 620.3105; m/z $C_{38}H_{41}N_3O_5Na$ (M+Na)$^+$ 642.2931; HPLC-MS (ESI+): m/z 620.4 [100%, (M+H)$^+$], (ESI+): m/z 642.2 [10%, (M+Na)$^+$].

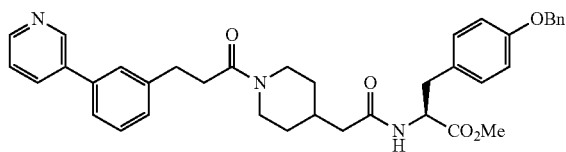 [SMILES: COC(=O)[C@H](Cc1ccc(OCc2ccccc2)cc1)NC(=O)CC1CCN(C(=O)CCc2cccc(-c3cccnc3)c2)CC1]

Example 67. Methyl (S)-3-(4-(benzyloxy)phenyl)-2-(2-(1-(3-(3-(pyridin-3-yl)phenyl)propanoyl)piperidin-4-yl)acetamido)propanoate (SR5-078)

SR5-078 (0.043 g, 72%) was prepared from SR2-107 (0.060 g, 0.096 mmol) and pyridine-3-boronic acid pinacol ester (0.022 g, 0.106 mmol) using general method 5. HPLC: >98% [$t_R$=6.9 min, 60% MeOH, 40% water (with 0.1% TFA), 20 min]. $^1$H NMR (500 MHz, DMSO-$d_6$) δ 8.95-8.84 (m, 1H), 8.62-8.52 (m, 1H), 8.23 (d, J=8.0 Hz, 1H), 8.11-8.02 (m, 1H), 7.74-7.46 (m, 56), 7.47-7.25 (m, 4H), 7.13 (d, J=8.2 Hz, 2H), 6.91 (d, J=8.7 Hz, 2H), 5.04 (s, 2H), 4.51-4.39 (m, 1H), 4.30 (s, 1H), 3.77 (m, 1H), 3.60 (s, 3H), 2.98 (dd, J=14.0, 5.1 Hz, 1H), 2.94-2.81 (m, 3H), 2.78 (dd, J=13.8, 10.1 Hz, 1H), 2.73-2.61 (m, 2H), 2.47-2.36 (m, 1H), 1.96 (d, J=7.1 Hz, 2H), 1.74 (s, 1H), 1.48 (m, 1H), 1.32 (m, 1H), 0.94-0.72 (m, 2H). HRMS (ESI+): m/z $C_{38}H_{42}N_3O_5$ (M+H)$^+$ 620.3105; m/z $C_{38}H_{41}N_3O_5Na$ (M+Na)$^+$ 642.2938; HPLC-MS (ESI+): m/z 620.4 [100%, (M+H)$^+$], (ESI+): m/z 642.2 [10%, (M+Na)$^+$].

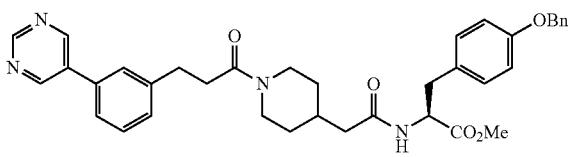 [SMILES: COC(=O)[C@H](Cc1ccc(OCc2ccccc2)cc1)NC(=O)CC1CCN(C(=O)CCc2cccc(-c3cncnc3)c2)CC1]

Example 68. Methyl (S)-3-(4-(benzyloxy)phenyl)-2-(2-(1-(3-(4-(pyridin-3-yl)phenyl)propanoyl)piperidin-4-yl)acetamido)propanoate (SR5-079)

SR5-079 (0.046 g, 77%) was prepared from SR2-110 (0.060 g, 0.096 mmol) and pyridine-3-boronic acid pinacol ester (0.022 g, 0.106 mmol) using general method 5. HPLC: >98% [$t_R$=5.1 min, 50% MeOH, 50% water (with 0.1% TFA), 20 min]. $^1$H NMR (500 MHz, DMSO-$d_6$) δ 8.86 (d, J=2.6 Hz, 1H), 8.60-8.51 (m, 1H), 8.23 (d, J=8.0 Hz, 1H), 8.10-7.99 (m, 1H), 7.67-7.58 (m, 2H), 7.54-7.26 (m, 8H), 7.13 (d, J=8.7 Hz, 2H), 6.91 (d, J=8.6 Hz, 2H), 5.06 (s, 1H), 5.04 (s, 1H, rotamer), 4.46 (m, 1H), 4.34-4.26 (m, 1H), 3.87-3.69 (m, 1H), 3.61 (s, 3H), 2.98 (dd, J=13.8, 5.1 Hz, 1H), 2.93-2.73 (m, 4H), 2.69-2.56 (m, 2H), 2.48-2.36 (m, 1H), 1.97 (d, J=7.2 Hz, 2H), 1.83-1.67 (m, 1H), 1.55-1.42 (m, 1H), 1.38-1.30 (m, 1H), 1.02-0.68 (m, 2H). HRMS (ESI+): m/z $C_{38}H_{42}N_3O_5$ (M+H)$^+$ 620.3104; m/z $C_{38}H_{41}N_3O_5Na$ (M+Na)$^+$ 642.2939; HPLC-MS (ESI+): m/z 620.4 [100%, (M+H)$^+$], (ESI+): m/z 642.2 [10%, (M+Na)$^+$].

Example 69. Methyl (S)-3-(4-(benzyloxy)phenyl)-2-(2-(1-(3-(3-(pyrimidin-5-yl)phenyl)propanoyl)piperidin-4-yl)acetamido)propanoate (SR5-081)

SR5-081 (0.034 g, 69%) was prepared from SR2-107 (0.050 g, 0.080 mmol) and pyrimidine-5-boronic acid pinacol ester (0.018 g, 0.088 mmol) using general method 5. HPLC: >98% [$t_R$=12.8 min, 50% MeOH, 50% water (with 0.1% TFA), 20 min]. $^1$H NMR (500 MHz, DMSO-$d_6$) δ 9.19 (d, J=1.8 Hz, 1H), 9.14 (m, 2H), 8.23 (d, J=8.0 Hz, 1H), 7.72-7.67 (m, 1H), 7.62 (d, J=7.8 Hz, 1H), 7.48-7.25 (m, 7H), 7.13 (d, J=8.0 Hz, 2H), 6.91 (d, J=8.6 Hz, 2H), 5.05 (s, 1H), 5.03 (s, 1H, rotamer), 4.53-4.40 (m, 1H), 4.35-4.23 (m, 1H), 3.87-3.72 (m, 1H), 3.60 (s, 3H), 2.98 (dd, J=14.0, 4.9 Hz, 1H), 2.94-2.83 (m, 3H), 2.78 (dd, J=13.8, 10.0 Hz, 1H), 2.72-2.59 (m, 2H), 2.49-2.34 (m, 1H), 1.96 (m, 2H), 1.82-1.66 (m, 1H), 1.55-1.43 (m, 1H), 1.38-1.22 (m, 1H), 0.95-0.73 (m, 2H). HRMS (ESI+): m/z $C_{37}H_{41}N_4O_5$ (M+H)$^+$ 621.3057; m/z $C_{37}H_{40}N_4O_5Na$ (M+Na)$^+$ 643.2882; HPLC-MS (ESI+): m/z 621.3 [100%, (M+H)$^+$], (ESI+): m/z 643.3 [10%, (M+Na)$^+$].

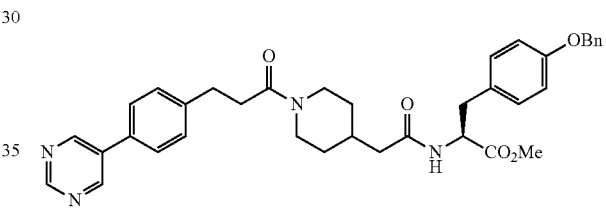

Example 70. Methyl (S)-3-(4-(benzyloxy)phenyl)-2-(2-(1-(3-(4-(pyrimidin-5-yl)phenyl)propanoyl)piperidin-4-yl)acetamido)propanoate (SR5-082)

SR5-082 (0.038 g, 76%) was prepared from SR2-110 (0.050 g, 0.080 mmol) and pyrimidine-5-boronic acid pinacol ester (0.018 g, 0.088 mmol) using general method 5. HPLC: >98% [$t_R$=5.8 min, 55% MeOH, 45% water (with 0.1% TFA), 20 min]. $^1$H NMR (500 MHz, DMSO-$d_6$) δ 9.16 (d, J=7.6 Hz, 1H), 9.11 (m, 2H), 8.23 (d, J=8.0 Hz, 1H), 7.75-7.61 (m, 2H), 7.62-7.49 (m, 1H), 7.47-7.28 (m, 7H), 7.16-7.09 (m, 2H), 6.94-6.88 (m, 2H), 5.06 (s, 1H), 5.03 (s, 1H, rotamer), 4.47 (td, J=9.3, 4.7 Hz, 1H), 4.35-4.23 (m, 1H), 3.84-3.68 (m, 1H), 3.61 (s, 3H), 2.98 (dd, J=13.8, 5.1 Hz, 1H), 2.92-2.81 (m, 3H), 2.78 (dd, J=13.8, 10.1 Hz, 1H), 2.69-2.55 (m, 2H), 2.49-2.36 (m, 1H), 1.97 (d, J=7.4 Hz, 2H), 1.82-1.65 (m, 1H), 1.54-1.42 (m, 1H), 1.33 (m, 1H), 1.01-0.70 (m, 2H). HRMS (ESI+): m/z $C_{37}H_{41}N_4O_5$ (M+H)$^+$ 621.3059; m/z $C_{37}H_{40}N_4O_5Na$ (M+Na)$^+$ 643.2884; HPLC-MS (ESI+): m/z 621.4 [100%, (M+H)$^+$], (ESI+): m/z 643.2 [40%, (M+Na)$^+$].

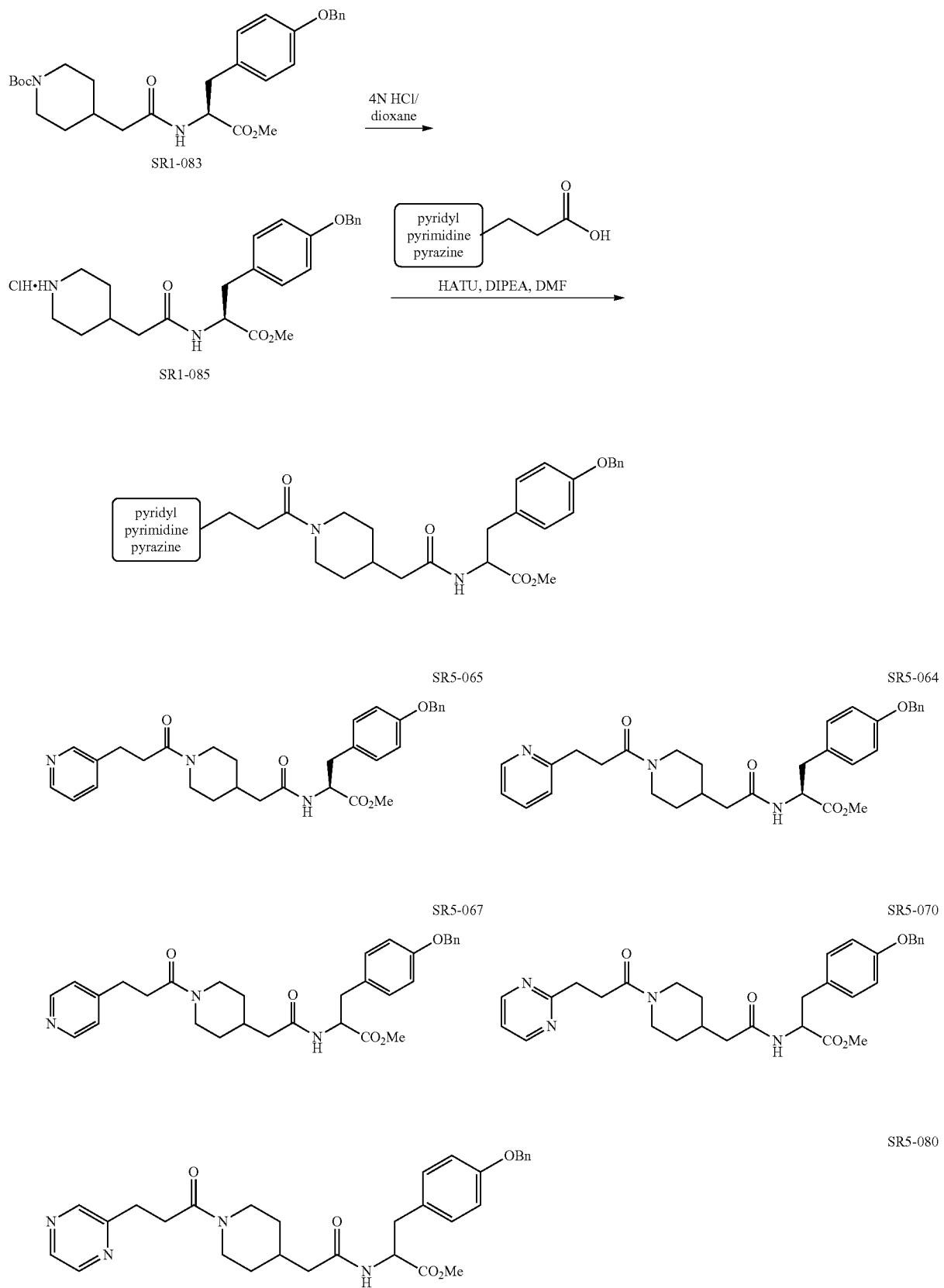

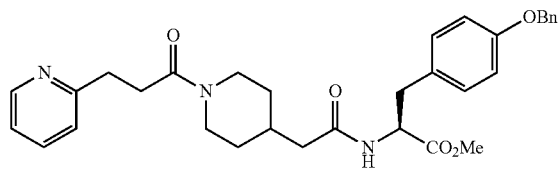 [SMILES: COC(=O)[C@H](Cc1ccc(OCc2ccccc2)cc1)NC(=O)CC1CCN(C(=O)CCc2ccccn2)CC1]

Example 71. Methyl (S)-3-(4-(benzyloxy)phenyl)-2-(2-(1-(3-(pyridin-2-yl)propanoyl)piperidin-4-yl)acetamido)propanoate (SR5-064)

SR5-064 (0.056 g, 91%) was prepared from SR1-085 (0.050 g, 0.112 mmol) and 3-(pyridyl-2-yl)propionic acid (0.020 g, 0.34 mmol) using general method 4. HPLC: >98% [$t_R$=5.1 min, 60% MeOH, 40% water (with 0.1% TFA), 20 min]. $^1$H NMR (500 MHz, DMSO-$d_6$) δ 8.46 (d, J=4.2 Hz, 1H), 8.25 (d, J=8.0 Hz, 1H), 7.71-7.62 (m, 1H), 7.47-7.33 (m, 4H), 7.34-7.24 (m, 2H), 7.22-7.16 (m, 1H), 7.13 (d, J=8.3 Hz, 2H), 6.92 (dd, J=8.7, 2.8 Hz, 2H), 5.06 (s, 1H), 5.04 (s, 1H, rotamer), 4.50-4.42 (m, 1H), 4.31-4.20 (m, 1H), 3.86-3.72 (m, 1H), 3.61 (s, 3H), 3.03-2.83 (m, 4H), 2.83-2.63 (m, 3H), 2.48-2.37 (m, 1H), 1.97 (d, J=7.2 Hz, 2H), 1.81-1.72 (m, 1H), 1.55-1.41 (m, 1H), 1.39-1.27 (m, 1H), 1.02-0.73 (m, 2H). HRMS (ESI+): m/z $C_{32}H_{38}N_3O_5$ (M+H)$^+$ 544.2807; m/z $C_{32}H_{37}N_3O_5Na$ (M+Na)$^+$ 566.2611; HPLC-MS (ESI+): m/z 544.3 [100%, (M+H)$^+$], (ESI+): m/z 566.3 [10%, (M+Na)$^+$].

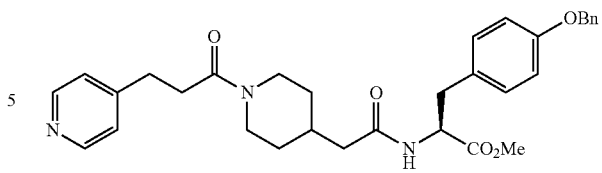

Example 73. Methyl (S)-3-(4-(benzyloxy)phenyl)-2-(2-(1-(3-(pyridin-4-yl)propanoyl)piperidin-4-yl)acetamido)propanoate (SR5-067)

SR5-067 (0.053 g, 87%) was prepared from SR1-085 (0.050 g, 0.112 mmol) and 3-(pyridyl-4-yl)propionic acid (0.020 g, 0.34 mmol) using general method 4. HPLC: >98% [$t_R$=4.0 min, 50% MeOH, 50% water (with 0.1% TFA), 20 min]. $^1$H NMR (500 MHz, DMSO-$d_6$) δ 8.49-8.39 (m, 2H), 8.25 (d, J=8.0 Hz, 1H), 7.47-7.39 (m, 2H), 7.41-7.34 (m, 2H), 7.35-7.29 (m, 1H), 7.29-7.22 (m, 2H), 7.13 (d, J=8.5 Hz, 2H), 6.92 (dd, J=8.7, 2.2 Hz, 2H), 5.09-5.00 (m, 2H), 4.51-4.41 (m, 1H), 4.32-4.22 (m, 1H), 3.83-3.68 (m, 1H), 3.61 (s, 3H), 2.98 (dd, J=13.8, 5.1 Hz, 1H), 2.95-2.73 (m, 4H), 2.69-2.57 (m, 2H), 2.49-2.36 (m, 1H), 1.96 (d, J=7.2 Hz, 2H), 1.81-1.66 (m, 1H), 1.54-1.45 (m, 1H), 1.40-1.26 (m, 1H), 1.01-0.66 (m, 2H). HRMS (ESI+): m/z $C_{32}H_{38}N_3O_5$ (M+H)$^+$544.2793; m/z $C_{32}H_{37}N_3O_5Na$ (M+Na)$^+$ 566.2625; HPLC-MS (ESI+): m/z 544.4 [100%, (M+H)$^+$], (ESI+): m/z 566.4 [10%, (M+Na)$^+$].

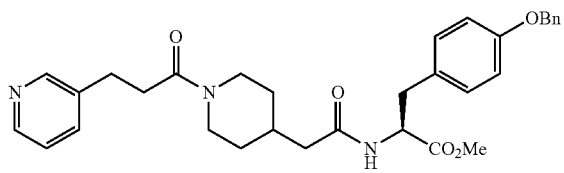 [SMILES: COC(=O)[C@H](Cc1ccc(OCc2ccccc2)cc1)NC(=O)CC1CCN(C(=O)CCc2cccnc2)CC1]

Example 72. Methyl (S)-3-(4-(benzyloxy)phenyl)-2-(2-(1-(3-(pyridin-3-yl)propanoyl)piperidin-4-yl)acetamido)propanoate (SR5-065)

SR5-065 (0.057 g, 92%) was prepared from SR1-085 (0.050 g, 0.112 mmol) and 3-(pyridyl-3-yl)propionic acid (0.020 g, 0.34 mmol) using general method 4. HPLC: >98% [$t_R$=4.1 min, 60% MeOH, 40% water (with 0.1% TFA), 20 min]. $^1$H NMR (500 MHz, DMSO-$d_6$) δ 8.46 (dd, J=4.4, 2.2 Hz, 1H), 8.43-8.34 (m, 1H), 8.25 (d, J=8.0 Hz, 1H), 7.71-7.61 (m, 1H), 7.48-7.23 (m, 6H), 7.13 (d, J=8.6 Hz, 2H), 6.92 (dd, J=8.5, 1.8 Hz, 2H), 5.06 (s, 1H), 5.04 (s, 1H), 4.53-4.41 (m, 1H), 4.34-4.20 (m, 1H), 3.83-3.68 (m, 1H), 3.61 (s, 3H), 2.98 (dd, J=13.8, 5.1 Hz, 1H), 2.90-2.72 (m, 4H), 2.69-2.53 (m, 2H), 2.48-2.33 (m, 1H), 2.01-1.92 (m, 2H), 1.82-1.67 (m, 1H), 1.53-1.44 (m, 1H), 1.38-1.25 (m, 1H), 0.95-0.69 (m, 2H). HRMS (ESI+): m/z $C_{32}H_{38}N_3O_5$ (M+H)$^+$ 544.2801; m/z $C_{32}H_{37}N_3O_5Na$ (M+Na)$^+$ 566.2624; HPLC-MS (ESI+): m/z 544.3 [100%, (M+H)$^+$], (ESI+): m/z 566.3 [10%, (M+Na)$^+$].

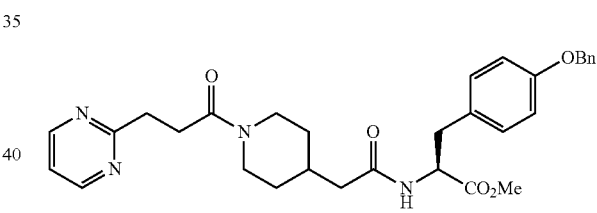

Example 74. Methyl (S)-3-(4-(benzyloxy)phenyl)-2-(2-(1-(3-(pyrimidin-2-yl)propanoyl)piperidin-4-yl)acetamido)propanoate (SR5-070)

SR5-070 (0.045 g, 74%) was prepared from SR1-085 (0.050 g, 0.112 mmol) and 3-(pyrimidin-2-yl)propionic acid (0.020 g, 0.34 mmol) using general method 4. HPLC: >98% [$t_R$=6.9 min, 50% MeOH, 50% water (with 0.1% TFA), 20 min]. $^1$H NMR (500 MHz, DMSO-$d_6$) δ 8.70 (dd, J=4.9, 2.1 Hz, 2H), 8.26 (d, J=8.0 Hz, 1H), 7.49-7.38 (m, 1H), 7.40-7.33 (m, 3H), 7.35-7.28 (m, 2H), 7.14 (dd, J=8.7, 2.9 Hz, 2H), 6.92 (dd, J=8.5, 5.9 Hz, 2H), 5.05 (s, 2H), 4.51-4.42 (m, 1H), 4.29-4.19 (m, 1H), 3.90-3.74 (m, 1H), 3.61 (s, 3H), 3.17-3.05 (m, 2H), 2.99 (dd, J=13.9, 5.1 Hz, 1H), 2.97-2.85 (m, 1H), 2.86-2.69 (m, 3H), 2.48-2.35 (m, 1H), 1.98 (dd, J=7.7, 2.1 Hz, 2H), 1.83-1.70 (m, 1H), 1.61-1.43 (m, 1H), 1.39-1.26 (m, 1H), 1.13-0.71 (m, 2H). HRMS (ESI+): m/z $C_{31}H_{37}N_4O_5$ (M+H)$^+$ 545.2751; m/z $C_{31}H_{36}N_4O_5Na$ (M+Na)$^+$ 567.2580; HPLC-MS (ESI+): m/z 545.3 [100%, (M+H)$^+$], (ESI+): m/z 567.3 [20%, (M+Na)$^+$].

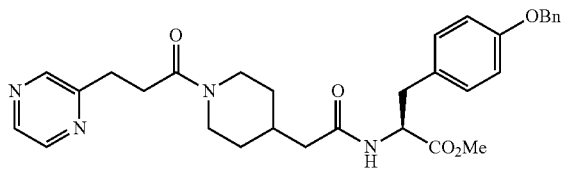 [SMILES: COC(=O)[C@H](Cc1ccc(OCc2ccccc2)cc1)NC(=O)CC1CCN(C(=O)CCc2cnccn2)CC1]

Example 75. Methyl (S)-3-(4-(benzyloxy)phenyl)-2-(2-(1-(3-(pyrazin-2-yl)propanoyl)piperidin-4-yl)acetamido)propanoate (SR5-080)

SR5-080 (0.041 g, 57%) was prepared from SR1-085 (0.059 g, 0.133 mmol) and 3-(pyrimidin-3-yl)propionic acid (0.025 g, 0.133 mmol) using general method 4. HPLC: >98% [$t_R$=7.0 min, 50% MeOH, 50% water (with 0.1% TFA), 20 min]. $^1$H NMR (500 MHz, DMSO-$d_6$) δ 8.58 (d, J=2.5 Hz, 1H), 8.55-8.50 (m, 1H), 8.44 (t, J=2.8 Hz, 1H), 8.24 (d, J=8.0 Hz, 1H), 7.47-7.39 (m, 2H), 7.41-7.33 (m, 2H), 7.34-7.28 (m, 1H), 7.13 (dd, J=8.6, 1.7 Hz, 2H), 6.92 (dd, J=8.5, 5.4 Hz, 2H), 5.05 (s, 2H), 4.51-4.42 (m, 1H), 4.31-4.18 (m, 1H), 3.87-3.71 (m, 1H), 3.65-3.55 (m, 3H), 3.05-2.94 (m, 3H), 2.94-2.83 (m, 1H), 2.83-2.67 (m, 3H), 2.46-2.34 (m, 1H), 1.97 (d, J=7.2 Hz, 2H), 1.79-1.70 (m, 1H), 1.58-1.42 (m, 1H), 1.42-1.19 (m, 1H), 1.04-0.72 (m, 2H). HRMS (ESI+): m/z $C_{31}H_{37}N_4O_5$ (M+H)$^+$ 545.2749; m/z $C_{31}H_{36}N_4O_5Na$ (M+Na)$^+$ 567.2567; HPLC-MS (ESI+): m/z 545.3 [100%, (M+H)$^+$], (ESI+): m/z 567.3 [30%, (M+Na)$^+$].

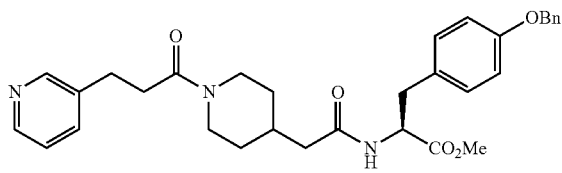 [SMILES: COC(=O)[C@H](Cc1ccc(OCc2ccccc2)cc1)NC(=O)CC1CCN(C(=O)CCc2cccnc2)CC1]

Example 76. Methyl (S)-3-(4-methoxyphenyl)-2-(2-(1-(3-(pyridin-3-yl)propanoyl)piperidin-4-yl)acetamido)propanoate (SR5-086)

SR5-086 (0.042 g, 67%) was prepared from SR2-133 (0.050 g, 0.135 mmol) and 3-(pyridyl-3-yl)propionic acid (0.022 g, 0.148 mmol) using general method 4. HPLC: >98% [$t_R$=3.7 min, 45% MeOH, 55% water (with 0.1% TFA), 20 min]. $^1$H NMR (500 MHz, DMSO-$d_6$) δ 8.47 (s, 1H), 8.44-8.36 (m, 1H), 8.23 (d, J=8.0 Hz, 1H), 7.71-7.63 (m, 1H), 7.30 (m, 1H), 7.13 (d, J=8.6 Hz, 2H), 6.83 (d, J=8.7 Hz, 2H), 4.53-4.40 (m, 1H), 4.33-4.22 (m, 1H), 3.81-3.74 (m, 1H), 3.72 (s, 2H), 3.68 (s, 1H, rotamer), 3.61 (s, 3H), 2.98 (dd, J=13.9, 5.1 Hz, 1H), 2.93-2.73 (m, 4H), 2.69-2.57 (m, 2H), 2.46-2.35 (m, 1H), 1.96 (d, J=7.3 Hz, 2H), 1.80-1.68 (m, 1H), 1.55-1.44 (m, 1H), 1.36-1.26 (m, 1H), 1.00-0.71 (m, 2H). HRMS (ESI+): m/z $C_{26}H_{34}N_3O_5$ (M+H)$^+$ 468.2491; m/z $C_{26}H_{33}N_3O_5Na$ (M+Na)$^+$ 490.2309; HPLC-MS (ESI+): m/z 468.2 [100%, (M+H)$^+$], (ESI+): m/z 490.2 [10%, (M+Na)$^+$].

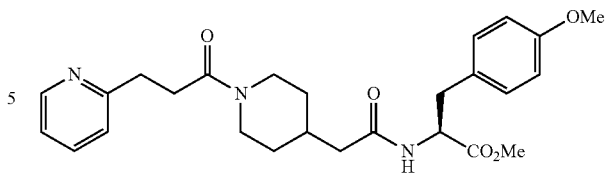

Example 77. Methyl (S)-3-(4-methoxyphenyl)-2-(2-(1-(3-(pyridin-2-yl)propanoyl)piperidin-4-yl)acetamido)propanoate (SR5-087)

SR5-087 (0.040 g, 63%) was prepared from SR2-133 (0.050 g, 0.135 mmol) and 3-(pyridyl-2-yl)propionic acid (0.022 g, 0.148 mmol) using general method 4. HPLC: >99% [$t_R$=4.7 min, 45% MeOH, 55% water (with 0.1% TFA), 20 min]. $^1$H NMR (500 MHz, DMSO-$d_6$) δ 8.47 (s, 1H), 8.24 (d, J=8.0 Hz, 1H), 7.74-7.63 (m, 1H), 7.28 (d, J=7.8 Hz, 1H), 7.25-7.16 (m, 1H), 7.13 (d, J=8.3 Hz, 2H), 6.83 (d, J=8.2 Hz, 3H), 4.50-4.43 (m, 1H), 4.32-4.20 (m, 1H), 3.88-3.74 (m, 1H), 3.72 (s, 1.5H), 3.69 (s, 1.5H), 3.61 (s, 3H), 3.04-2.91 (m, 3H), 2.90-2.82 (m, 1H), 2.78 (dd, J=13.8, 10.0 Hz, 1H), 2.76-2.66 (m, 1H), 2.47-2.34 (m, 1H), 1.97 (dd, J=7.5, 2.2 Hz, 2H), 1.82-1.67 (m, 1H), 1.56-1.43 (m, 1H), 1.37-1.26 (m, 1H), 1.03-0.73 (m, 2H). HRMS (ESI+): m/z $C_{26}H_{34}N_3O_5$ (M+H)$^+$ 468.2487; m/z $C_{26}H_{33}N_3O_5Na$ (M+Na)$^+$ 490.2303; HPLC-MS (ESI+): m/z 468.3 [100%, (M+H)$^+$], (ESI+): m/z 490.0 [10%, (M+Na)$^+$].

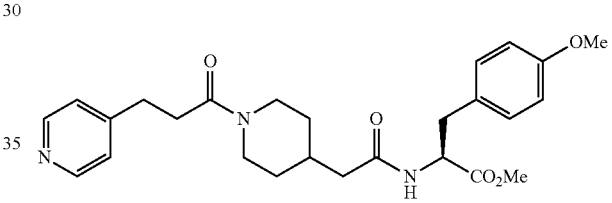

Example 78. Methyl (S)-3-(4-methoxyphenyl)-2-(2-(1-(3-(pyridin-4-yl)propanoyl)piperidin-4-yl)acetamido)propanoate (SR5-088)

SR5-088 (0.039 g, 62%) was prepared from SR2-133 (0.050 g, 0.135 mmol) and 3-(pyridyl-4-yl)propionic acid (0.022 g, 0.148 mmol) using general method 4. HPLC: >99% [$t_R$=6.6 min, 40% MeOH, 60% water (with 0.1% TFA), 20 min]. $^1$H NMR (500 MHz, DMSO-$d_6$) δ 8.50-8.40 (m, 2H), 8.23 (d, J=8.0 Hz, 1H), 7.30-7.24 (m, 2H), 7.13 (d, J=8.6 Hz, 2H), 6.83 (d, J=8.3 Hz, 2H), 4.46 (ddd, J=13.2, 10.1, 5.3 Hz, 1H), 4.34-4.17 (m, 1H), 3.81-3.73 (m, 1H), 3.72 (s, 2H), 3.69 (s, 1H, rotamer), 3.61 (s, 3H), 2.98 (dd, J=13.8, 5.1 Hz, 1H), 2.93-2.72 (m, 4H), 2.64 (m, 2H), 2.47-2.34 (m, 1H), 2.04-1.89 (m, 2H), 1.80-1.70 (m, 1H), 1.60-1.44 (m, 1H), 1.37-1.19 (m, 1H), 1.00-0.65 (m, 2H). HRMS (ESI+): m/z $C_{26}H_{34}N_3O_5$ (M+H)$^+$ 468.2490; m/z $C_{26}H_{33}N_3O_5Na$ (M+Na)$^+$ 490.2302; HPLC-MS (ESI+): m/z 468.3 [100%, (M+H)$^+$], (ESI+): m/z 490.2 [10%, (M+Na)$^+$].

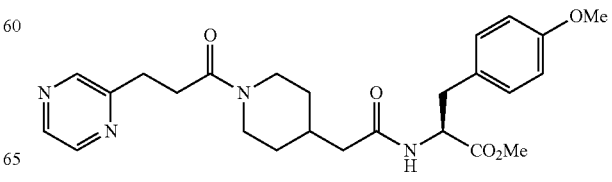

Example 79. Methyl (S)-3-(4-methoxyphenyl)-2-(2-(1-(3-(pyrazin-2-yl)propanoyl)piperidin-4-yl)acetamido)propanoate (SR5-091)

SR5-091 (0.038 g, 61%) was prepared from SR2-133 (0.050 g, 0.135 mmol) and 3-(pyrazin-2-yl)propanoic acid (0.022 g, 0.148 mmol) using general method 4. HPLC: >99% [$t_R$=3.8 min, 40% MeOH, 60% water (with 0.1% TFA), 20 min]. $^1$H NMR (500 MHz, DMSO-$d_6$) δ 8.59 (s, 1H), 8.54 (s, 1H), 8.48-8.43 (m, 1H), 8.24 (d, J=8.0 Hz, 1H), 7.13 (dd, J=8.5, 1.9 Hz, 2H), 6.83 (dd, J=8.6, 3.3 Hz, 2H), 4.46 (dt, J=13.2, 4.5 Hz, 1H), 4.32-4.17 (m, 1H), 3.85-3.74 (m, 1H), 3.71 (s, 1.5H), 3.70 (s, 1.5H), 3.61 (s, 3H), 3.05-2.94 (m, 3H), 2.94-2.83 (m, 1H), 2.83-2.71 (m, 3H), 2.47-2.32 (m, 1H), 2.04-1.88 (m, 2H), 1.86-1.67 (m, 1H), 1.61-1.44 (m, 1H), 1.30-1.18 (m, 1H), 1.05-0.69 (m, 2H). HRMS (ESI+): m/z $C_{25}H_{33}N_4O_5$ (M+H)$^+$ 469.2437; m/z $C_{25}H_{32}N_4O_5Na$ (M+Na)$^+$ 491.2251; HPLC-MS (ESI+): m/z 469.3 [100%, (M+H)$^+$], (ESI+): m/z 491.2 [30%, (M+Na)$^+$].

Example 81. Methyl (S)-3-(4-methoxyphenyl)-2-(2-(1-(3-(3-(1-methyl-1H-pyrazol-4-yl)phenyl)propanoyl)piperidin-4-yl)acetamido)propanoate (SR5-097)

SR5-097 (0.030 g, 67%) was prepared from SR2-089 (0.045 g, 0.082 mmol) and 1-methylpyrazole-4-boronic acid pinacol ester (0.019 g, 0.090 mmol) using general method 5. HPLC: >98% [$t_R$=6.4 min, 60% MeOH, 40% water (with 0.1% TFA), 20 min]. $^1$H NMR (500 MHz, DMSO-$d_6$) δ 8.22 (d, J=7.9 Hz, 1H), 8.10 (s, 1H), 7.84 (s, 1H), 7.43 (d, J=3.3 Hz, 1H), 7.39-7.32 (m, 1H), 7.29-7.21 (m, 1H), 7.13 (d, J=8.6 Hz, 2H), 7.06 (d, J=7.6 Hz, 1H), 6.83 (d, J=8.1 Hz, 2H), 4.54-4.39 (m, 1H), 4.34-4.23 (m, 1H), 3.86 (s, 3H), 3.83-3.73 (m, 1H), 3.73-3.70 (s, 1.5H), 3.67 (s, 1.5H, rotamer), 3.61 (s, 3H), 2.98 (dd, J=13.9, 5.2 Hz, 1H), 2.93-2.72 (m, 4H), 2.67-2.57 (m, 2H), 2.48-2.32 (m, 1H), 1.96 (d, J=7.2 Hz, 2H), 1.80-1.64 (m, 1H), 1.49 (m, 1H), 1.35-1.22 (m, 1H), 1.03-0.66 (m, 2H). HRMS (ESI+): m/z $C_{31}H_{39}N_4O_5$ (M+H)$^+$ 547.2902; m/z $C_{31}H_{38}N_4O_5Na$ (M+Na)$^+$571.2781; HPLC-MS (ESI+): m/z 547.3 [100%, (M+H)$^+$], (ESI+): m/z 571.0 [10%, (M+Na)$^+$].

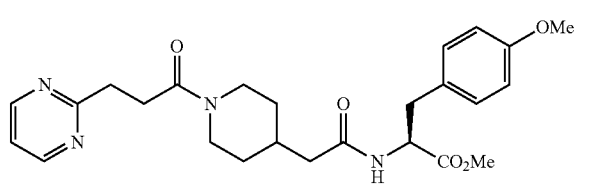 [SMILES: COC(=O)[C@H](Cc1ccc(OC)cc1)NC(=O)CC1CCN(C(=O)CCc2ncccn2)CC1]

Example 80. Methyl (S)-3-(4-methoxyphenyl)-2-(2-(1-(3-(pyrimidin-2-yl)propanoyl)piperidin-4-yl)acetamido)propanoate (SR5-092)

SR5-092 (0.039 g, 62%) was prepared from SR2-133 (0.050 g, 0.135 mmol) and 3-(pyridine-2-yl)propanoic acid (0.022 g, 0.148 mmol) using general method 4. HPLC: >99% [$t_R$=8.3 min, 30% MeOH, 70% water (with 0.1% TFA), 20 min]. $^1$H NMR (500 MHz, DMSO-$d_6$) δ 8.71 (dd, J=4.9, 2.5 Hz, 2H), 8.24 (d, J=8.0 Hz, 1H), 7.32 (t, J=4.9 Hz, 1H), 7.13 (dd, J=8.2, 1.6 Hz, 2H), 6.84 (dd, J=8.5, 3.1 Hz, 2H), 4.55-4.42 (m, 1H), 4.31-4.16 (m, 1H), 3.91-3.74 (m, 1H), 3.71 (s, 1.5H), 3.70 (s, 1.5H), 3.62 (s, 3H), 3.15-3.05 (m, 2H), 2.99 (dd, J=13.9, 5.1 Hz, 1H), 2.94-2.86 (m, 1H), 2.85-2.72 (m, 3H), 2.47-2.34 (m, 1H), 1.99 (dd, J=7.4, 2.9 Hz, 2H), 1.82-1.72 (m, 1H), 1.60-1.42 (m, 1H), 1.40-1.22 (m, 1H), 1.17-0.70 (m, 2H). HRMS (ESI+): m/z $C_{25}H_{33}N_4O_5$ (M+H)$^+$ 469.2445; m/z $C_{25}H_{32}N_4O_5Na$ (M+Na)$^+$ 491.2261; HPLC-MS (ESI+): m/z 469.3 [100%, (M+H)$^+$], (ESI+): m/z 491.2 [10%, (M+Na)$^+$].

Example 82. Methyl (S)-3-(4-methoxyphenyl)-2-(2-(1-(3-(4-(1-methyl-1H-pyrazol-4-yl)phenyl)propanoyl)piperidin-4-yl)acetamido)propanoate (SR5-098)

SR5-098 (0.041 g, 82%) was prepared from SR2-090 (0.050 g, 0.092 mmol) and 1-methylpyrazole-4-boronic acid pinacol ester (0.021 g, 0102 mmol) using general method 5. HPLC: >97% [$t_R$=6.3 min, 60% MeOH, 40% water (with 0.1% TFA), 20 min]. $^1$H NMR (500 MHz, DMSO-$d_6$) δ 8.22 (d, J=7.9 Hz, 1H), 8.07 (s, 1H), 7.81 (d, J=2.2 Hz, 1H), 7.45 (dd, J=8.3, 3.1 Hz, 2H), 7.21 (dd, J=8.1, 2.7 Hz, 2H), 7.13 (d, J=8.6 Hz, 2H), 6.83 (d, J=8.6 Hz, 2H), 4.53-4.41 (m, 1H), 4.34-4.20 (m, 1H), 3.85 (s, 3H), 3.81-3.74 (m, 1H), 3.72 (s, 1.5H), 3.68 (s, 1.5H, rotamer), 3.61 (s, 3H), 2.98 (dd, J=13.8, 5.1 Hz, 1H), 2.93-2.81 (m, 1H), 2.81-2.72 (m, 3H), 2.62-2.54 (m, 2H), 2.48-2.33 (m, –1H), 1.96 (d, J=7.1 Hz, 2H), 1.80-1.66 (m, 1H), 1.55-1.43 (m, 1H), 1.37-1.27 (m, 1H), 1.01-0.75 (m, 2H). HRMS (ESI+): m/z $C_{31}H_{39}N_4O_5$ (M+H)$^+$ 547.2907; m/z $C_{31}H_{38}N_4O_5Na$ (M+Na)$^+$ 571.2777; HPLC-MS (ESI+): m/z 547.3 [100%, (M+H)$^+$], (ESI+): m/z 571.3 [20%, (M+Na)$^+$].

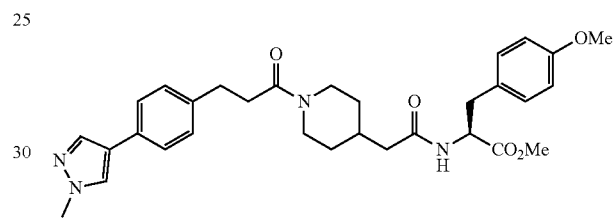

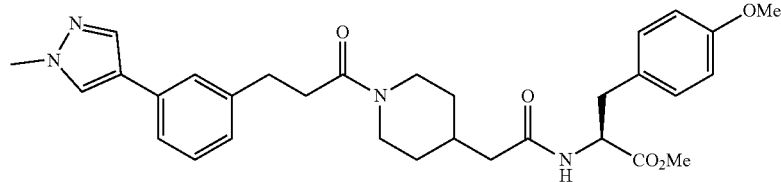 [SMILES: COC(=O)[C@H](Cc1ccc(OC)cc1)NC(=O)CC1CCN(C(=O)CCc2cccc(-c3cnn(C)c3)c2)CC1]

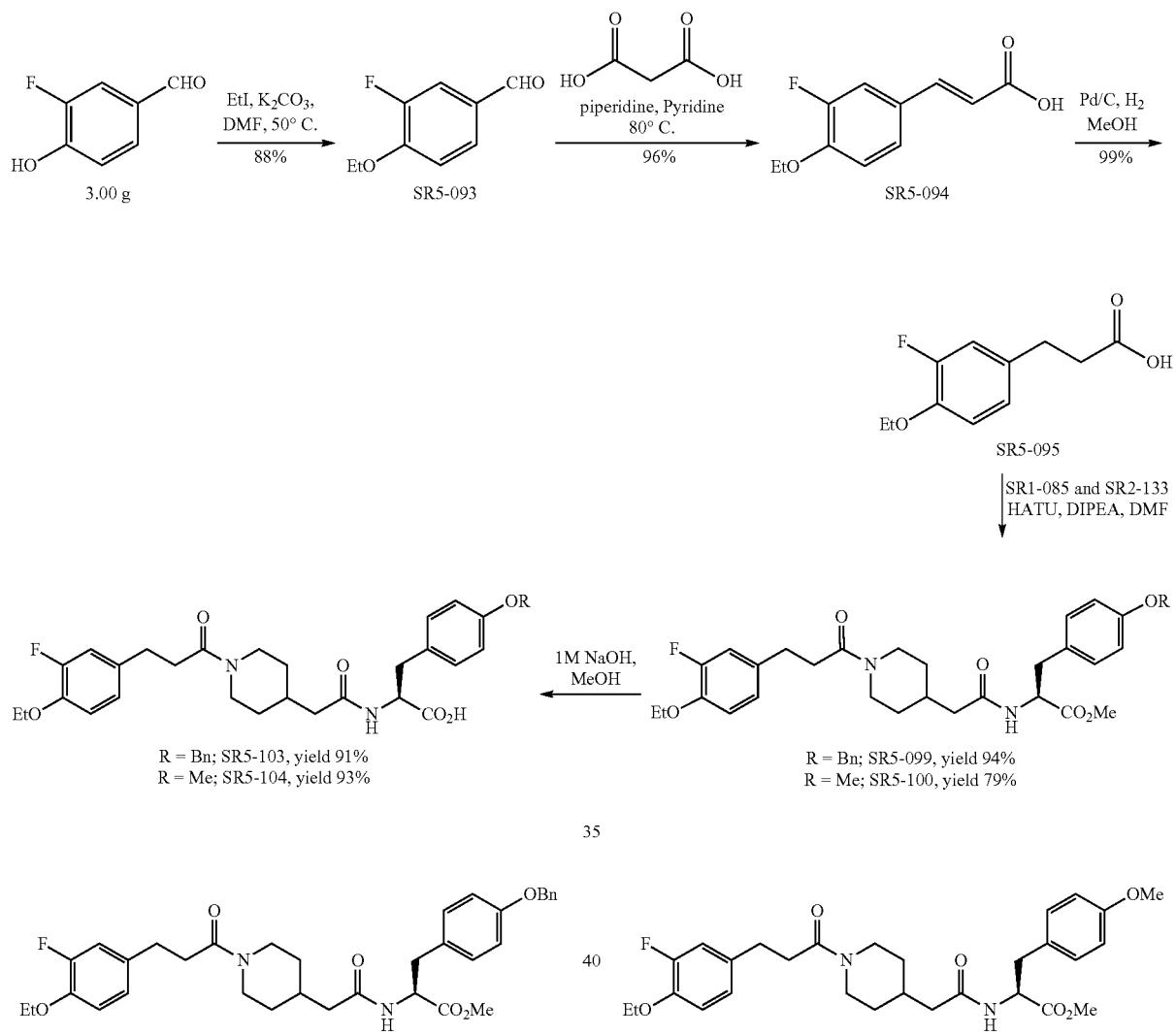

Scheme 8

Example 83. Methyl (S)-3-(4-(benzyloxy)phenyl)-2-(2-(1-(3-(4-ethoxy-3-fluorophenyl)propanoyl)piperidin-4-yl)acetamido)propanoate (SR5-099)

SR5-099 (0.126 g, 94%) was prepared from SR1-085 (0.100 g, 0.223 mmol) and 3-(4-ethoxy-3-fluorophenyl) propanoic acid (0.052 g, 0.246 mmol) using general method 4. HPLC: >98% [$t_R$=11.1 min, 65% MeOH, 35% water (with 0.1% TFA), 20 min]. $^1$H NMR (500 MHz, DMSO-$d_6$) δ 8.23 (d, J=8.0 Hz, 1H), 7.42 (dd, J=12.5, 7.4 Hz, 1H), 7.39-7.33 (m, 3H), 7.35-7.28 (m, 2H), 7.13 (d, J=8.7 Hz, 2H), 7.08 (dd, J=12.7, 3.3 Hz, 2H), 7.06-6.97 (m, 1H), 6.98-6.93 (m, 1H), 6.91 (d, J=8.7 Hz, 1H), 5.06 (s, 1H), 5.04 (s, 1H, rotamer), 4.52-4.41 (m, 1H), 4.33-4.21 (m, 1H), 4.05 (q, J=6.7 Hz, 2H), 3.84-3.68 (m, 1H), 3.61 (s, 3H), 2.98 (dd, J=13.8, 5.1 Hz, 1H), 2.88-2.76 (m, 1H), 2.76-2.67 (m, 3H), 2.64-2.52 (m, 2H), 2.46-2.34 (m, 1H), 1.96 (d, J=7.2 Hz, 2H), 1.80-1.67 (m, 1H), 1.54-1.43 (m, 1H), 1.36-1.28 (m, 4H), 1.00-0.71 (m, 2H). HRMS (ESI+): m/z $C_{35}H_{41}FN_2O_6$(M+H)$^+$ 605.3008; m/z $C_{35}H_{40}FN_4O_6Na$ (M+Na)$^+$ 627.2827; HPLC-MS (ESI+): m/z 605.2 [100%, (M+H)$^+$], (ESI+): m/z 627.2 [40%, (M+Na)$^+$].

Example 84. Methyl (S)-2-(2-(1-(3-(4-ethoxy-3-fluorophenyl)propanoyl)piperidin-4-yl)acetamido)-3-(4-methoxyphenyl)propanoate (SR5-100)

SR5-100 (0.126 g, 94%) was prepared from SR2-133 (0.100 g, 0.270 mmol) and 3-(4-ethoxy-3-fluorophenyl) propanoic acid (0.063 g, 0.296 mmol) using general method 4. HPLC: >98% [$t_R$=8.1 min, 60% MeOH, 40% water (with 0.1% TFA), 20 min]. $^1$H NMR (500 MHz, DMSO-$d_6$) δ 8.23 (d, J=8.0 Hz, 1H), 7.13 (d, J=8.6 Hz, 2H), 7.13-7.06 (m, 1H), 7.07-6.99 (m, 1H), 7.00-6.93 (m, 1H), 6.83 (d, J=8.7 Hz, 2H), 4.45 (ddd, J=13.1, 7.2, 2.5 Hz, 1H), 4.33-4.21 (m, 1H), 4.06 (q, J=7.0 Hz, 2H), 3.81-3.73 (m, 1H), 3.72 (s, 1.5H), 3.69 (s, 1.5H, rotamer), 3.61 (s, 3H), 2.98 (dd, J=13.8, 5.2 Hz, 1H), 2.91-2.79 (m, 1H), 2.79-2.67 (m, 4H), 2.58-2.53 (m, 1H), 2.46-2.35 (m, 1H), 1.97 (d, J=7.2 Hz, 2H), 1.79-1.69 (m, 1H), 1.54-1.43 (m, 1H), 1.32 (t, J=7.0 Hz, 3H), 1.31-1.22 (m, 1H), 1.00-0.66 (m, 2H). HRMS (ESI+): m/z $C_{29}H_{38}FN_2O_6$(M+H)$^+$ 529.2697; m/z $C_{29}H_{37}FN_2O_6Na$ (M+Na)$^+$ 551.2519; HPLC-MS (ESI+): m/z 529.2 [100%, (M+H)$^+$], (ESI+): m/z 551.2 [40%, (M+Na)$^+$].

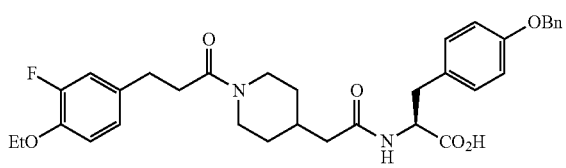 [SMILES: CCOc1ccc(CCC(=O)N2CCC(CC(=O)N[C@@H](Cc3ccc(OCc4ccccc4)cc3)C(=O)O)CC2)cc1F]

Example 85. (S)-3-(4-(Benzyloxy)phenyl)-2-(2-(1-(3-(4-ethoxy-3-fluorophenyl)propanoyl)piperidin-4-yl)acetamido)propanoic acid (SR5-103)

SR45-103 was obtained as a white foam (0.060 g, 94%) from SR5-099 (0.065 g, 0.107 mmol) using general method 3. HPLC: >98% [$t_R$=5.5 min, 70% MeOH, 30% water (with 0.1% TFA), 20 min]. $^1$H NMR (500 MHz, DMSO-$d_6$) δ 8.07 (d, J=8.3 Hz, 1H), 7.50-7.34 (m, 4H), 7.34-7.28 (m, 1H), 7.14 (d, J=8.7 Hz, 2H), 7.08 (ddd, J=12.7, 5.3, 2.1 Hz, 1H), 7.06-6.98 (m, 1H), 6.98-6.93 (m, 1H), 6.91 (d, J=8.5 Hz, 2H), 5.06 (s, 1H), 5.03 (s, 1H, rotamer), 4.46-4.36 (m, 1H), 4.32-4.22 (m, 1H), 4.10-3.99 (m, 2H), 3.81-3.65 (m, 1H), 3.01 (dd, J=13.8, 4.6 Hz, 1H), 2.89-2.78 (m, 1H), 2.78-2.68 (m, 3H), 2.60-2.53 (m, 2H), 2.46-2.34 (m, 1H), 2.01-1.89 (m, 2H), 1.80-1.65 (m, 1H), 1.53-1.42 (m, 1H), 1.37-1.26 (m, 4H), 0.92-0.71 (m, 2H). HRMS (ESI+): m/z $C_{34}H_{40}FN_2O_6$ (M+H)$^+$ 591.2852; m/z $C_{34}H_{39}FN_2O_6Na$ (M+Na)$^+$ 613.2680; HPLC-MS (ESI+): m/z 591.2 [100%, (M+H)$^+$], (ESI−): m/z 613.2 [100%, (M−H)$^−$].

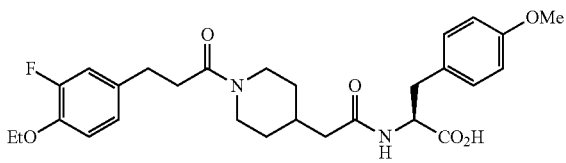 [SMILES: CCOc1ccc(CCC(=O)N2CCC(CC(=O)N[C@@H](Cc3ccc(OC)cc3)C(=O)O)CC2)cc1F]

Example 86. (S)-2-(2-(1-(3-(4-Ethoxy-3-fluorophenyl)propanoyl)piperidin-4-yl)acetamido)-3-(4-methoxyphenyl)propanoic acid (SR5-104)

SR45-104 was obtained as a white foam (0.060 g, 94%) from SR5-100 (0.047 g, 0.97 mmol) using general method 3. HPLC: >96% [$t_R$=6.5 min, 60% MeOH, 40% water (with 0.1% TFA), 20 min]. $^1$H NMR (500 MHz, DMSO-$d_6$) δ 12.62 (s, 1H), 8.08 (d, J=8.3 Hz, 1H), 7.14 (d, J=8.6 Hz, 2H), 7.12-7.07 (m, 1H), 7.07-6.99 (m, 1H), 7.00-6.93 (m, 1H), 6.83 (d, J=8.7 Hz, 2H), 4.47-4.35 (m, 1H), 4.31-4.19 (m, 1H), 4.06 (q, J=7.0 Hz, 2H), 3.80-3.71 (m, 1H), 3.72 (s, 1.5H), 3.68 (s, 1.5H, rotamer), 3.00 (dd, J=13.9, 4.7 Hz, 1H), 2.90-2.78 (m, 1H), 2.78-2.67 (m, 3H), 2.62-2.52 (m, 2H), 2.46-2.34 (m, 1H), 1.96 (d, J=7.2 Hz, 2H), 1.78-1.67 (m, 1H), 1.55-1.43 (m, 1H), 1.32 (t, J=7.0 Hz, 3H), 1.30-1.22 (m, 1H), 0.90-0.71 (m, 2H). HRMS (ESI+): m/z $C_{28}H_{36}FN_2O_6$(M+H)$^+$515.2531; m/z $C_{28}H_{35}FN_2O_6Na$ (M+Na)$^+$ 537.2359; HPLC-MS (ESI+): m/z 515.2 [100%, (M+H)$^+$], (ESI−): m/z 513.2 [100%, (M−H)$^−$].

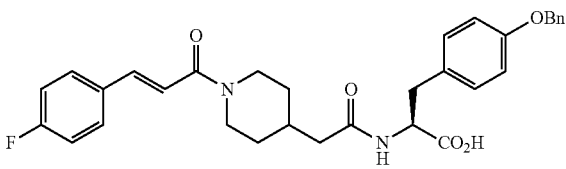 [SMILES: O=C(CC1CCN(C(=O)/C=C/c2ccc(F)cc2)CC1)N[C@@H](Cc1ccc(OCc2ccccc2)cc1)C(=O)O]

Example 87. (S,E)-3-(4-(Benzyloxy)phenyl)-2-(2-(1-(3-(4-fluorophenyl)acryloyl)piperidin-4-yl)acetamido)propanoic acid (SR3-027)

SR3-027 was obtained as a white foam (0.025 g, 87%) from its methyl ester (0.030 g, 0.0537 mmol) using general method 3. HPLC: >98% [$t_R$=4.6 min, 75% MeOH, 25% water (with 0.1% TFA), 20 min]. $^1$H NMR (500 M Hz, DMSO-$d_6$) δ 12.64 (bs, 1H), 8.11 (d, J=8.2 Hz, 1H), 7.86-7.72 (m, 2H), 7.51-7.42 (m, 2H), 7.40 (m, 1H), 7.37 (m, 2H), 7.32 (m, 1H), 7.28-7.17 (m, 3H), 7.15 (d, J=8.6 Hz, 2H), 6.92 (d, J=8.6 Hz, 2H), 5.06 (s, 2H), 4.41 (m, 2H), 4.17 (m, 1H), 3.07-2.93 (m, 2H), 2.75 (dd, J=13.7, 10.3 Hz, 1H), 2.66-2.54 (m, 1H), 1.99 (d, J=7.1 Hz, 2H), 1.87-1.74 (m, 1H), 1.63-1.52 (m, 1H), 1.49-1.32 (m, 1H), 1.10-0.76 (m, 2H). $^{19}$F NMR (471 MHz, DMSO-$d_6$) δ −113.9 (m). HRMS (ESI+): m/z $C_{32}H_{34}FN_2O_5$(M+H)$^+$ 545.2438; m/z $C_{32}H_{33}FN_2O_5Na$ (M+Na)$^+$567.2242; HPLC-MS (ESI+): m/z 545.2 [60%, (M+H)$^+$], (ESI−): m/z 543.2.2 [100%, (M−H)$^−$].

Example 88. Inhibition of Luciferase Activity by Compound Treatment in a Cell Based Luciferase Assay Luciferase activity inhibition results from the compounds tested in the assay described herein are shown in FIG. 1. The assay was conduced as follows.
Calculation of % Inhibition of Luciferase Activity by Compound Treatment in the Cell Based Luciferase Assay
The luciferase assays were carried out in replicates. The average of the replicate wells was calculated first.

2% DMSO Treatment Control

Replicate 1 Replicate 2 Replicate 3=Average "$X$" (Eqn. 1)

Test Compounds

Replicate 1 Replicate 2 Replicate 3=Average "$Y$" (Eqn. 2)

Then, the fold change for the treatment versus control was calculated by dividing the average of compound treatments with average of 2% DMSO control treatment.

Fold change "$R$"=Average "$Y$"/Average "$X$" (Eqn. 3)

Next, the % fold change was calculated by multiplying Fold change "R" with 100.

% Fold change "$F$"="$R$"×100 (Eqn. 4)

Finally, the % inhibition was calculated by subtracting the % Fold change from 100.

% Inhibition "$I$"=100−"$F$" (Eqn. 5)

Purification of GST/GST-Oct4 Protein
Growth and induction of the bacteria with GST/GST-Oct4. In 30 mL of LB, bacteria (Strain-BL21 DE3 pLysS) with GST-Oct4/GST were cultured overnight in the presence of ampicillin (100 μg/mL) as a selection antibiotic. The next day, 25 mL of the bacterial culture was inoculated into a 225 mL LB medium with ampicillin (100 μg/mL) for an hour and $OD_{600}$ was measured. Once the $OD_{600}$ reached 0.4-0.5, final concentration of 500 μM IPTG was added to induce the bacterial cells. The culture was grown in a shaker for another 5 h-6 h at 30° C. [Note: Bacterial culture expressing GST only protein was induced with 500 μM IPTG at 37° C. for only 2 hrs.] At the end of the induction, the culture was centrifuged at 3500 rpm for 20 mins at 4° C. (Centrifuge—Beckman Coulter Avanti J-E refrigerated centrifuge). The supernatant was discarded and the bacterial pellet was processed further for protein purification.

Purification of GST/GST-Oct4 proteins. The bacterial pellet was re-suspended entirely in 10 mL of cold lysis buffer. Next, the suspension was sonicated 4 times with 30 sec pulse on, 30 sec pulse off, until the culture becomes a clear solution. The bacterial suspension was kept on ice this entire time (Sonicator—Fisher Scientific Sonic Dismembrator Model 100 at power level 5). After sonication, an additional 1 mM PMSF and 0.5 mM DTT was added to the lysate. The lysates were incubated on a nutator for 15 min at 4° C. after which it was spun at 12,500 rpm for 20 min at 4° C. (Centrifuge—Beckman Coulter Avanti J-E refrigerated centrifuge). The supernatant was carefully transferred to another tube and pellet was discarded. 300 μL of bead slurry was added to the lysate prepared as mentioned above and incubated on a nutator at 4° C. for 2-3 h. The beads were spun at 1500 rpm for 5 min at 4° C. The supernatant was removed and the beads were washed with 10 mL cold DPBS with 0.1 mM DTT and 0.1 mM PMSF. The beads were spun down at 1500 rpm for 5 min at 4° C. The washing was repeated two more times. The solution of Reduced L-Glutathione was prepared by adding 61.5 mg to the 5 mL of elution buffer. The pH of the solution adjusted to 9.0 and then the total volume of the final elution buffer with Glutathione was adjusted to 10 mL. The final pH of the elution buffer was 9.0. Additional protease inhibitors were added again as follows 0.5 mM DTT, 0.02 mM Leupeptin and 1 mM PMSF. 500 μL of Elution Buffer was added to the beads and incubated at 4° C. for 45 min on a nutator. The beads were spun at 3000 rpm for 5 min at 4° C. The elution was carried out thrice each time with 500 μL of the elution buffer. The eluted protein was measured using a standard Bradford's protein estimation.

In-Vitro Binding Assay Protocol

Coating of the wells with GST proteins. GST Proteins (GST-Oct4 and GST) were diluted to required 10 μg/100 μL/well concentrations in DPBS and are coated onto the high binding plates (96 well, F-Bottom, Black, Fluotrac, High binding, Sterile) for overnight (12-18 h) at 4° C. After the incubation, the contents of the well (unbound protein) were discarded by aspiration and the wells are washed twice with 100 μL DPBS/well.

Compound treatment. For screening, the compounds were first dissolved in DMSO at 5 mM concentration (Main stock). Next two intermediate dilutions of 100 μM and 500 μM (working stock) were prepared in DMSO from the main stock of the compound. First the FITC conjugated YAP1 WW domain peptide (FTTC-YAP1 WW peptide) was added to the GST/GST-Oct4 protein coated wells at a final concentration of 20 nM in DPBS/well. Then the compounds were added to the designated wells at two different final concentrations of 1 μM or 5 μM.

GST-Oct4 coated wells: 99 μL of 20 nM FITC-YAP1 WW peptide in DPBS+1 μL of 100 μM of compound GST-Oct4 coated wells: 99 μL of 20 nM FITC-YAP1 WW peptide in DPBS+1 μL of 500 μM of compound The inhibition by the compound was compared with the following control wells.

GST-Oct4 coated wells: 99 μL of 20 nM FITC-YAP1 WW peptide in DPBS+1 μL of DMSO (Volume of the Vehicle)

GST coated wells: 99 μL of 20 nM FITC-YAP1 WW peptide in DPBS+1 μL of DMSO

The reaction was further incubated at room temperature on a low speed shaking platform for 3 h. The contents of the wells were discarded at the end of 3 h and the wells were washed thrice with 120 μL of DPBS/well. The bound FITC-YAP1 WW peptide was then measured using a Fluorescence plate reader (Perkin Elmer Wallac Envision 2103 multi-label reader at excitation wavelength 485 nm, emission wavelength 535 nm).

Reagents and Buffers

Composition of Bacterial Lysis Buffer (10 ml)

Tween20—0.5%,
0.4 mM Sodium Vanadate
0.4 mM Sodium Fluoride
0.5 mM PMSF
0.5 mM DTT
17.5 mM Lysozyme
0.483 mM DNAse1
5 mM Sarkosyl detergent
150 mM NaCl
1 mM EDTA (pH 8.0)
Adjust the volume to 10 ml with 1×DPBS.

Composition of the Elution Buffer (10 ml)

150 mM NaCl
50 mM Tris pH 8.0
1 mM EDTA
0.2% Triton X 100
5 mMDTT
10 mM Leupeptin
1 mM PMSF
Adjust the volume to 10 ml with 1×DPBS Preparation of Glutathione Sepharose 4B beads: Glutathione Sepharose 4B beads (GE Healthcare, #17-0756-01) were used for purification which were washed with cold DPBS+DTT (1 L/mL) thrice, centrifuged at 3000 rpm for 5 mins each time and finally dissolved in equal bead volume of DPBS with 1 L/mL DTT and 1 μL/mL PMSF (bead slurry).

DPBS, 1× (Corning Cellgro Catalogue #21-031-CV) pH 7.0±0.1

FITC-YAP1 WW peptide: Sequence-MAKTSSGQRYFLN-HIDQ (SEQ ID NO.: 1)

The N-terminal FITC tagged peptide was synthesized from Genscript. The peptide was dissolved in Molecular biology grade water at 2 mg/mL and the molarity was calculated as per the molecular weight of the peptide described in the specification sheet provided by Genscript. The HPLC purity of the peptide is 88.8% as per the specification sheet.

Generation of Sox2-Luciferase Stable Cell Lines and Cell Based Assay for YAP1 Inhibitors Preparing the plasmid constructs for the cell transfections. Filter paper carrying the spotted plasmid DNA were cut around the pencil circle marks and collected in a sterile 1.5 mL centrifuge tube. 30-40 μL of DNAase, RNAase free water was added to the filter paper to dissolve the DNA in the filter paper. 25 μL of E. coli. DH5a competent cells were transformed with a minimum of 100 ng plasmid DNA for each construct. A single colony of DH5a selected on an ampicillin plate was expanded for each plasmid and plasmid DNA was prepared for each of the constructs by standard mini- or midi-prep DNA isolation method.

Preparing A549 cells for transfections. A549 cells were grown to confluency in 10% FBS containing F12K medium with 1× antibiotic-antimycotic solution (complete F12K medium). The cells were washed once with 1×DPBS, trypsinized and harvested as a single cell suspension in complete medium. A549 cells were counted in a hemocytometer by mixing 10 μL of cell suspension with 10 μL of trypan blue solution (1:1 dilution). Cells were plated into two separate 60 mm cell culture dish at a seeding density of 120,000 cells in 3 mL of complete F12K medium. The cells were allowed to grow for 12-14 hours (overnight).

Transfection of plasmid DNA into A549 cells. The transfection of plasmids was carried out in OptiMEM medium in sterile conditions. FugeneHD was used to transfect the plasmid DNA into A549 cells. The ratio of DNA to FugeneHD was always maintained at 1:2; that is, for 1 μg of DNA, 2 μL of FugeneHD was used. OptiMEM medium and FugeneHD were brought to room temperature before starting the transfection reactions. The following reactions were prepared in separate tubes in sterile conditions:

Tube 1: 500 μL of OptiMEM medium+2 μg of Sox2-luciferase plasmid+1 μg of pcDNA3.1 plasmid+6 μL of FugeneHD Tube 2: 500 μL of OptiMEM medium+2 μg of Sox2-luciferase plasmid+1 μg of pcDNA3.1 plasmid+2 μg of pBABE-YAP1 plasmid+10 μL of FugeneHD While adding the components into the tubes, OptiMEM was added first, then the DNA was added directly into the OptiMEM medium in the tube. A brief spin was given at 800 g for 1 min to the tubes. Next, FugeneHD vial/tube was vortexed and mixed for 2-3 seconds on a cyclomixer as per manufacturer's instructions. Appropriate amounts of FugeneHD reagent was added directly into the OptiMEM medium without touching the walls of the tube. The two reactions were incubated for 25 mins at room temperature in sterile hood for complex formation. In the meantime, the A549 cells seeded in two 60 mm dishes were assessed for 70-80% confluency under the microscope. The cells were washed once with sterile DPBS to remove the media contents. Next, 500 μL of OptiMEM medium was added into both the 60 mm dishes with the A549 cells. After the 25 mins incubation of complex formation, the 500 μL of the reactions in tube 1 was added gently dropwise into one A549 60 mm dish. The process is repeated for the reaction prepared in the tube 2 and added to the second A549 60 mm dish. The two 60 mm dishes were incubated at 37 deg incubator for 6 hours. At the end of 6 hours, 3 mL of complete F12K medium is added to the 60 mm dishes and further incubated for 48 hours. After 48 hours, medium was aspirated out from the 60 mm dishes. 3 mL of complete F12K was added with the following selection antibiotics.

Dish 1: Transfected with Sox2-luciferase plasmid+pcDNA3.1 plasmid−10 μg/mL of Geneticin in 3 mL of complete F12K medium Dish 2: Transfected with Sox2-luciferase plasmid+pcDNA3.1 plasmid+pBABE-YAP1-10 μg/mL of Geneticin and 1 μg/mL of Puromycin in 3 mL of complete F12K medium The cells were further maintained in complete F12K medium with selection antibiotics all the time. The cells were monitored carefully and media change was given every 48 hours to maintain the antibiotic selection. A brief wash with DPBS was given during media change if too many dead cells were observed under the microscope. Also, amount of selection antibiotic can be increased or decreased based on the transfection efficiency and survival of the cells with the selection antibiotics. The colonies were observed in 3-4 weeks, which were picked and grown separately as clones and further screened, as described below.

Screening of the stable colonies for luciferase activity. To screen the luciferase activity of the clones, 3000 cells in 100 μL were seeded in a well of a white clear bottom 96 well plate (performed in duplicates). The cells were allowed to grow for 24 hours. After 24 hours, 50 μL of OneGlo EX reagent was added to the wells. The plate was incubated on a shaker (350 rpm) for 10 mins. The luciferase activity was measured in luminescence plate reader (Perkin Elmer Wallac Envision 2103 multi-label reader) through 96 plate luminescence aperture with measurement time of 0.1 second and 0% Glow (CT2) correction factor.

Screening of compounds using the stable cells. For screening assays, A549 Sox2-luc cells and A549 Sox2-luc+YAP1 cells were seeded in white clear bottom 96 well plate at a density of 4000 cells/100 L/well (performed in duplicates). The cells were allowed to grow for 12-14 hours. The compounds were dissolved in DMSO at 5 mM concentration (Main stock). The compounds were diluted to 5 μM in 1 mL of complete F12K medium.

DMSO control: 999 μL of complete F12K medium+1 μL of DMSO

5 μM Compound: 999 μL of complete F12K medium+1 μL of 5 mM compound

For the treatment of the cells, all the media in the wells was aspirated out. 100 μL of DMSO control or 100 μL of 5 μM Compound was dispensed into designated wells. Each treatment was performed in duplicates. The cells were incubated further for 48 h at 37 deg. At the end of the treatment, 50 μL of OneGlo EX reagent was added to each well. The plate was incubated on a shaker (350 rpm) for 10 mins.

The luciferase activity was measured in luminescence plate reader (Perkin Elmer Wallac Envision 2103 multi-label reader) through 96 plate luminescence aperture with measurement time of 0.1 second and 0% Glow (CT2) correction factor. The screening of compounds was primarily carried out using the A549 Sox2-luc+YAP1 cells. The % inhibition of luciferase activity was calculated for each treatment in comparison to DMSO control. 1 μM verteporfin (visudyne) can be used as a positive control if needed.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A compound of Formula I,

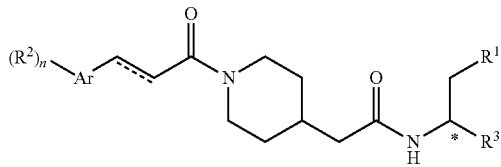

Formula I wherein,
the dash line is a bond that is present or absent;
n is 0, 1, or 2;
Ar is phenyl, pyridinyl, pyrimidinyl, or pyrazinyl;
$R^1$ is $C_1$-$C_8$ alkyl, $C_3$-$C_6$ cycloalkyl, or $C_6$ aryl, and of which is optionally substituted with one or more groups chosen from halo, hydroxyl, cyano, $C_1$-$C_6$ alkyl, $C_1$-$C_6$ haloalkyl, $C_1$-$C_6$ alkoxyl, $C_1$-$C_6$ haloalkoxyl, $C_3$-$C_6$ cycloalkyl, $C_3$-$C_6$ heterocycloalkyl, $C_6$ aryl, heteroaryl, $OCH_2$-$C_6$ aryl, or O—$CH_2$-heteroaryl;
$R^2$ is halo, OH, $C_1$-$C_8$ alkyl, $C_1$-$C_8$ alkoxyl, $C_6$ aryl, O—$C_6$ aryl, heteroaryl, O-heteroaryl, O—$CH_2$-$C_6$ aryl, or O—$CH_2$-heteroaryl; and
$R^3$ is $CH_2OH$, $CO_2H$, $CO_2$-$C_1$-$C_6$ alkyl, $CO_2$-$C_3$-$C_6$ cycloalkyl, or $CO_2$-$C_1$-$C_6$ heteroalkyl,
or a pharmaceutically acceptable salt thereof.

2. The compound of claim 1, wherein the stereochemistry at C* is R.

3. The compound of claim 1, wherein the stereochemistry at C* is S.

4. The compound of claim 1, wherein the dashed line is a bond that is absent.

5. The compound of claim 1, wherein $R^1$ is $C_1$-$C_8$ alkyl, optionally substituted with one or more groups chosen from halo, hydroxyl, cyano, $C_1$-$C_6$ alkyl, $C_1$-$C_6$ haloalkyl, $C_1$-$C_6$ alkoxyl, $C_1$-$C_6$ haloalkoxyl, $C_3$-$C_6$ cycloalkyl, $C_3$-$C_6$ heterocycloalkyl, $C_6$ aryl, heteroaryl, $OCH_2$-$C_6$ aryl, and O—$CH_2$-heteroaryl.

6. The compound of claim 1, wherein $R^1$ is $C_3$-$C_6$ cycloalkyl, optionally substituted with one or more groups chosen from halo, hydroxyl, cyano, $C_1$-$C_6$ alkyl, $C_1$-$C_6$ haloalkyl, $C_1$-$C_6$ alkoxyl, $C_1$-$C_6$ haloalkoxyl, $C_3$-$C_6$ cycloalkyl, $C_3$-$C_6$ heterocycloalkyl, $C_6$ aryl, heteroaryl, $OCH_2$-$C_6$ aryl, and O—$CH_2$-heteroaryl.

7. The compound of claim 1, wherein $R^1$ is phenyl optionally substituted with one or more groups chosen from halo, hydroxyl, cyano, $C_1$-$C_6$ alkyl, $C_1$-$C_6$ haloalkyl, $C_1$-$C_6$ alkoxyl, $C_1$-$C_6$ haloalkoxyl, $C_3$-$C_6$ cycloalkyl, $C_3$-$C_6$ heterocycloalkyl, $C_6$ aryl, heteroaryl, $OCH_2$-$C_6$ aryl, and O—$CH_2$-heteroaryl.

8. The compound of claim 7, wherein the phenyl group is substituted with one or more benzyloxy groups.

9. The compound of claim 7, wherein the phenyl group is substituted with one or more $C_1$-$C_6$ alkoxyl groups.

10. The compound of claim 7, wherein the phenyl group is substituted with one or more halo groups.

11. The compound of claim 7, wherein the phenyl group is substituted with one or more cyano, $C_1$-$C_6$ haloalkyl, or $C_1$-$C_6$ haloalkoxyl groups.

12. The compound of claim 7, wherein the phenyl group is substituted with one or more pyrazole, pyridinyl, pyrimidinyl, or pyrazinyl groups.

13. The compound of claim 1, wherein Ar is a phenyl group that is optionally substituted.

14. The compound of claim 13, wherein the phenyl group is substituted with one or two $R^2$ groups chosen from halo, hydroxyl, $C_1$-$C_8$ alkyl, $C_1$-$C_8$ alkoxyl, $C_6$ aryl, O—$C_6$ aryl, heteroaryl, O-heteroaryl, O—$CH_2$-$C_6$ aryl, and O—$CH_2$-heteroaryl.

15. The compound of claim 13, wherein the phenyl group is substituted with one or two halo groups.

16. The compound of claim 13, wherein the phenyl group is substituted with one or two $C_1$-$C_8$ alkoxyl groups.

17. The compound of claim 13, wherein the phenyl group is substituted with one or two heteroaryl groups.

18. The compound of claim 1, wherein Ar is pyridinyl, pyrimidinyl, or pyrazinyl, optionally substituted with one or two $R^2$ groups chosen from halo, hydroxyl, $C_1$-$C_8$ alkyl, $C_1$-$C_8$ alkoxyl, $C_6$ aryl, O—$C_6$ aryl, heteroaryl, O-heteroaryl, O—$CH_2$-$C_6$ aryl, and O—$CH_2$-heteroaryl.

19. The compound of claim 1, wherein n is 0.

20. The compound of claim 1, wherein $R^3$ is $CO_2Me$ or $CO_2H$.

21. The compound of claim 1, wherein the compound have Formula I-A:

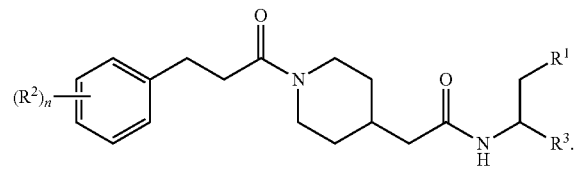

Formula I-A

22. The compound of claim 1, wherein the compounds have Formula I-B

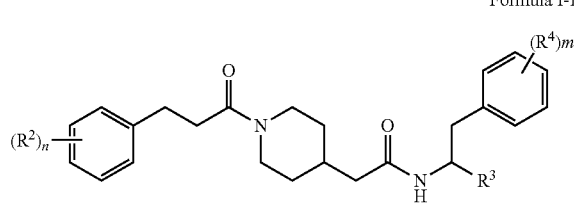

Formula I-B wherein m is 0, 1, or 2;

and $R^4$ is halo, OH, cyano, $C_1$-$C_6$ alkyl, $C_1$-$C_6$ haloalkyl, $C_1$-$C_6$ alkoxyl, $C_1$-$C_6$ haloalkoxyl, $C_3$-$C_6$ cycloalkyl, $C_3$-$C_6$ heterocycloalkyl, $C_6$ aryl, heteroaryl, $OCH_2$-$C_6$ aryl, or O—$CH_2$-heteroaryl.

23. The compound of claim 1, wherein the compounds have Formula I-C

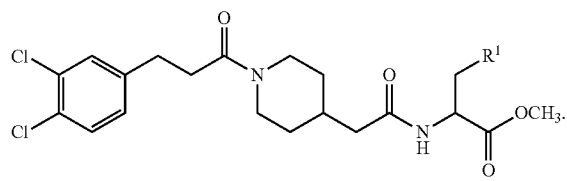

Formula I-C

24. The compound of claim 1, wherein the compound is chosen from

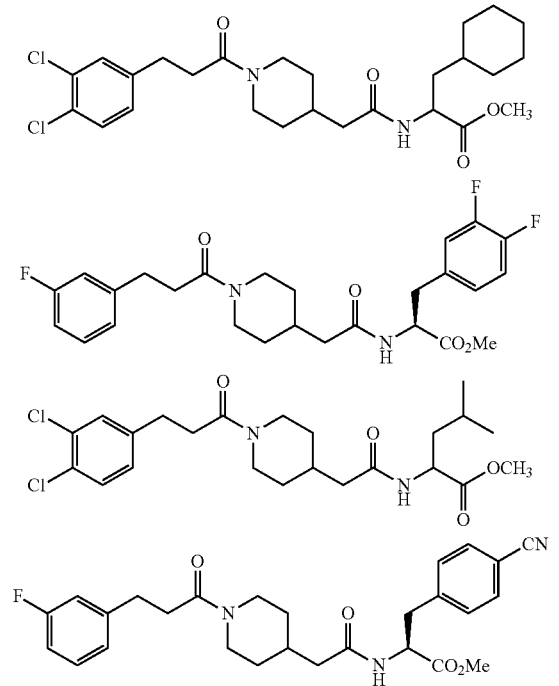

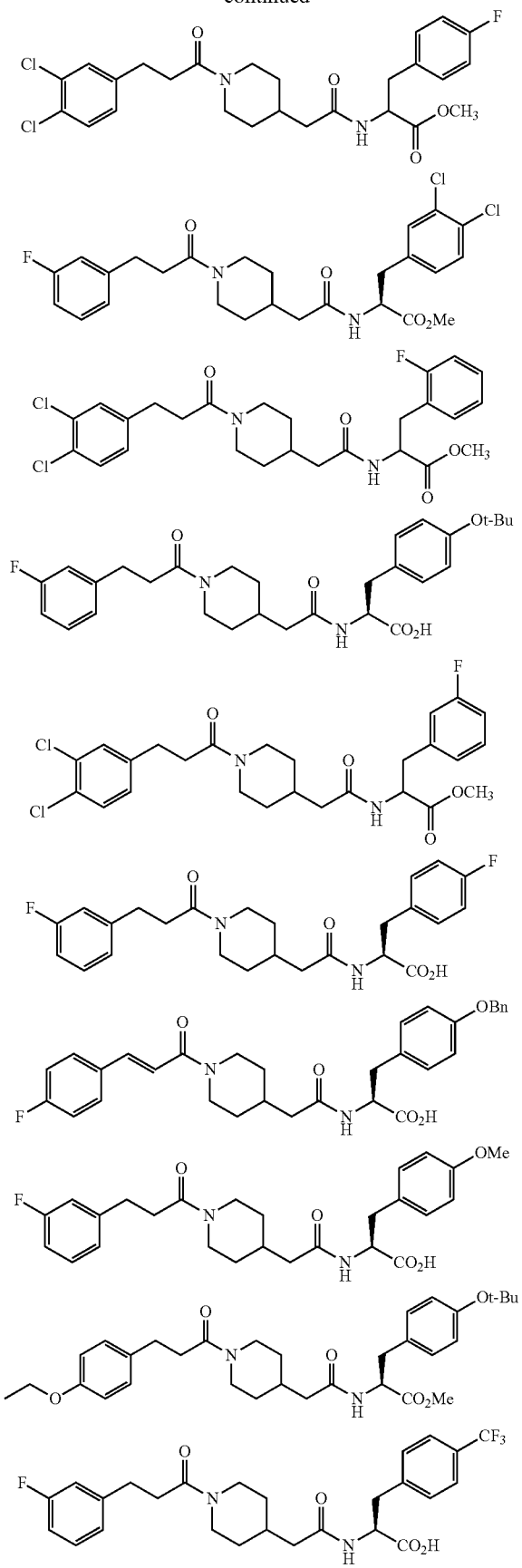

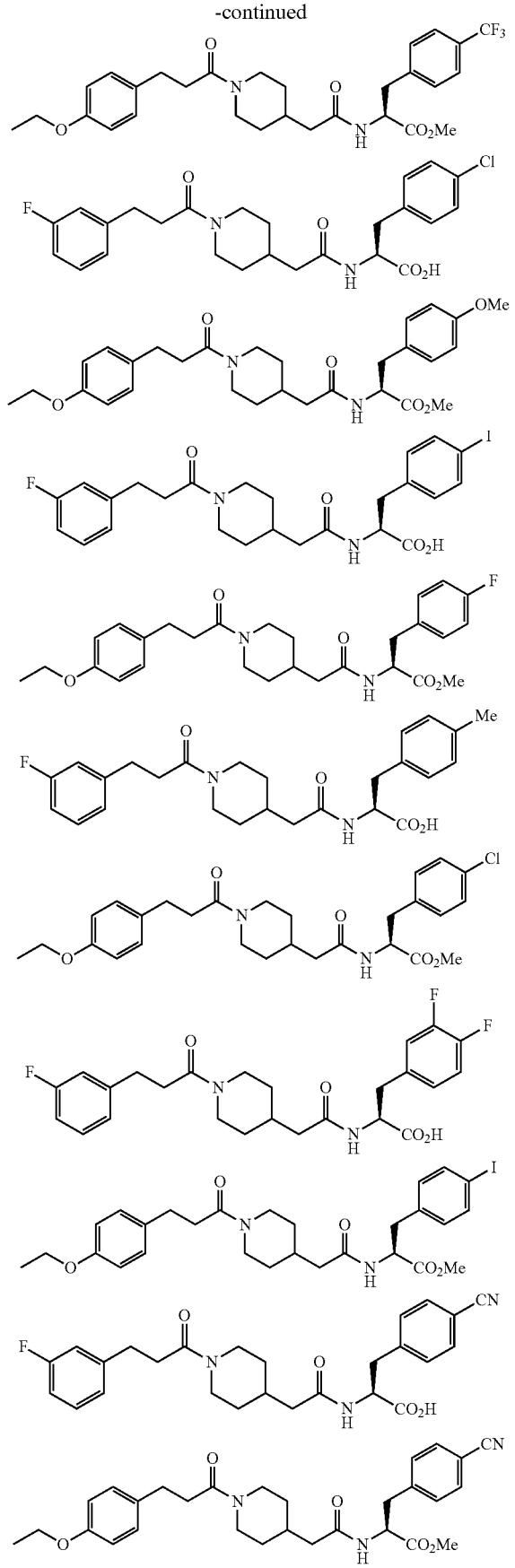
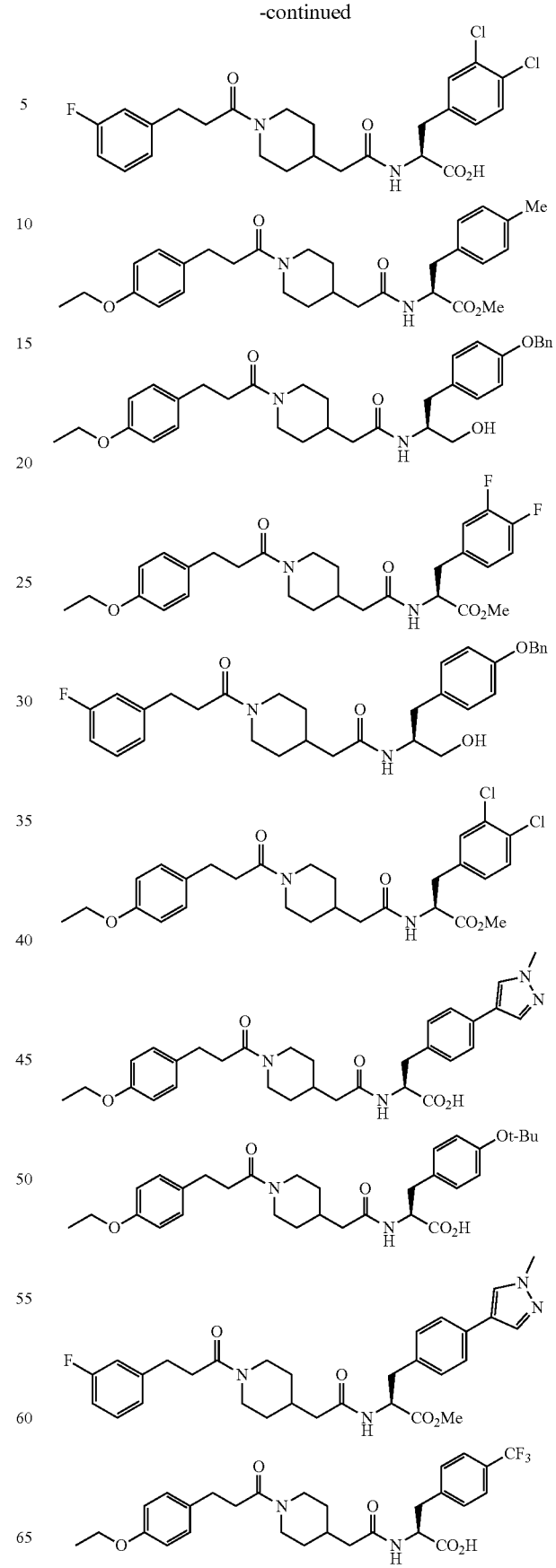

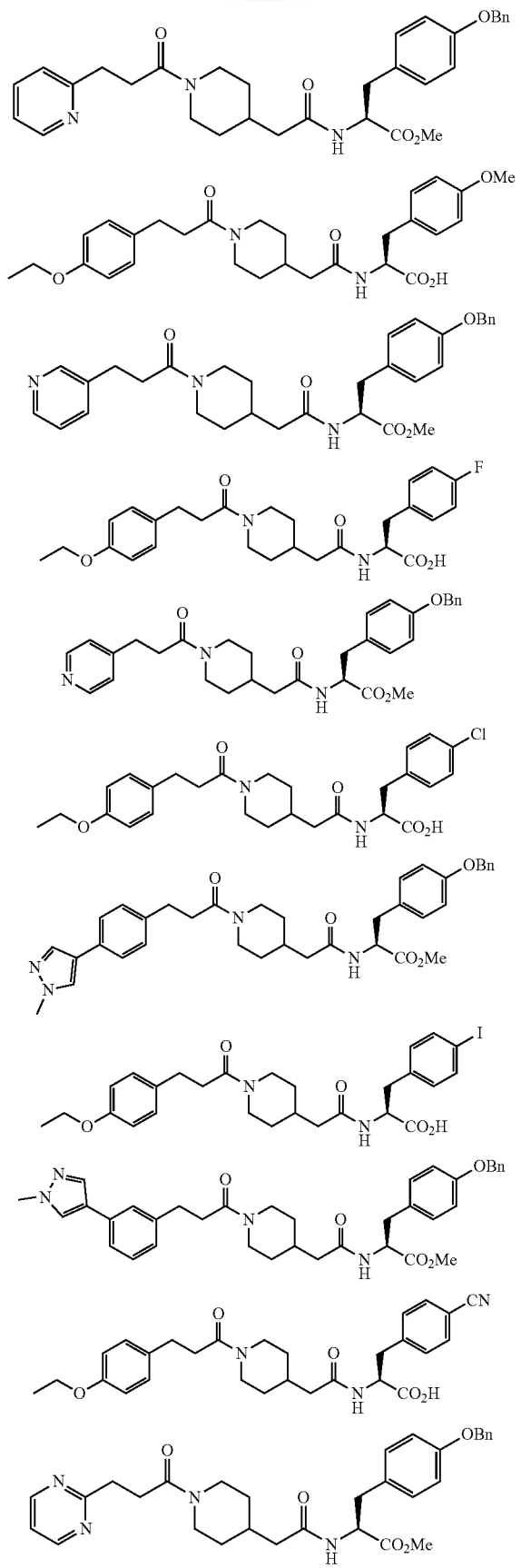
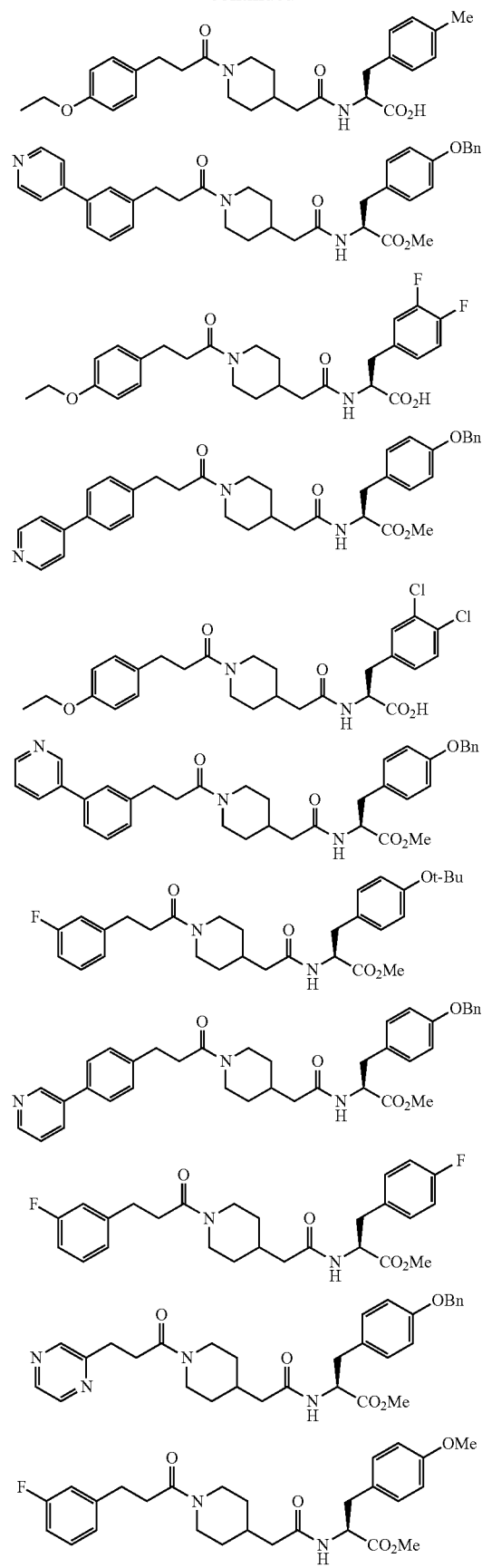

-continued

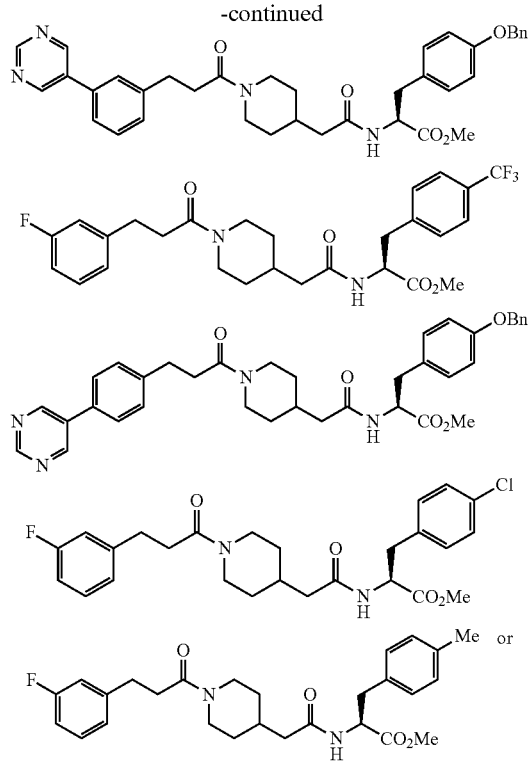

-continued

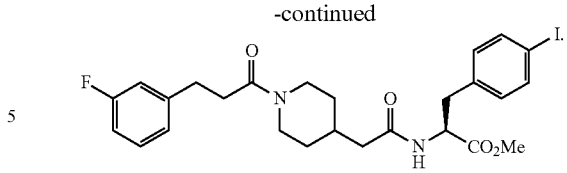

25. A pharmaceutical composition comprising a therapeutically effective amount of a compound of claim 1 and a pharmaceutical carrier and optional anticancer or anti-inflammatory agent.

26. A method of treating cancer in a subject in need thereof, comprising: administering to the subject the compound of claim 1.

27. The method of claim 26, wherein the cancer is selected from bladder cancer, brain cancer, breast cancer, colorectal cancer, cervical cancer, gastrointestinal cancer, genitourinary cancer, head and neck cancer, ovarian cancer, pancreatic cancer, prostate cancer, renal cancer, skin cancer, and testicular cancer.

28. The method of claim 26, wherein the cancer is lung cancer.

29. A method of killing a tumor cell in a subject, comprising contacting the cell with the compound of claim 1.

* * * * *

UNITED STATES PATENT AND TRADEMARK OFFICE
CERTIFICATE OF CORRECTION

PATENT NO. : 11,685,725 B2
APPLICATION NO. : 16/980538
DATED : June 27, 2023
INVENTOR(S) : Srikumar Chellappan et al.

It is certified that error appears in the above-identified patent and that said Letters Patent is hereby corrected as shown below:

On the Title Page

In the (57) Abstract section
Column 2, Line 7, delete "sternness." and insert -- stemness. --
Column 2, Line 9, delete "sternness." and insert -- stemness. --

In the (56) References Cited section
On page 2, Column 1, Line 25 of Other Publications, delete "8197013 8" and insert -- 81970138 --
On page 2, Column 1, Line 29 of Other Publications, delete "YAP 1" and insert -- YAP1 --
On page 2, Column 2, Line 32 of Other Publications, delete "Chern" and insert -- Chem --

In the Specification

In Column 7, Line 7, delete "C(O)H." and insert -- —C(O)H. --
In Column 30, Line 39, delete "Waldenstram's" and insert -- Waldenström's --
In Column 32, Line 21, delete "Publiation" and insert -- Publication --
In Column 32, Line 39, delete "cyclophosamide" and insert -- cyclophosphamide --
In Column 35, Lines 25-26, delete "cyclophosamide" and insert -- cyclophosphamide --
In Column 35, Line 54, delete "trastuzamab" and insert -- trastuzumab --
In Column 38, Line 29, delete "3H).)." and insert -- 3H). --
In Column 47, Line 26, delete "$C_{27}H_{34}C_1N_2O_5$" and insert -- $C_{27}H_{34}ClN_2O_5$ --
In Column 47, Line 27, delete "$C_{27}H_{33}C_1N_2O_5Na$" and insert -- $C_{27}H_{33}ClN_2O_5Na$ --
In Column 48, Line 46, delete "(EST+)" and insert -- (ESI+) --
In Column 51, Line 65, delete "$C_{26}H_{31}C_1NF_2O_4$" and insert -- $C_{26}H_{31}ClNF_2O_4$ --
In Column 55, Line 55, delete "(EST+)" and insert -- (ESI+) --
In Column 56, Line 47, delete "$C_{25}H_{29}C_1FN_2O_4$" and insert -- $C_{25}H_{29}ClFN_2O_4$ --
In Column 56, Line 49, delete "(EST+)" and insert -- (ESI+) --
In Column 58, Line 34, delete "(EST+)" and insert -- (ESI+) --

Signed and Sealed this
Third Day of October, 2023

*Katherine Kelly Vidal*
*Director of the United States Patent and Trademark Office*

CERTIFICATE OF CORRECTION (continued)
U.S. Pat. No. 11,685,725 B2

In Column 59, approximately Line 15, delete " 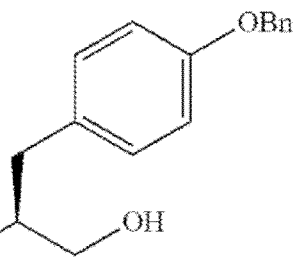 " and insert

-- 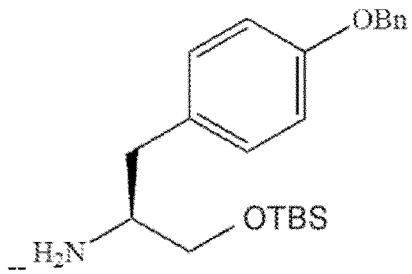 --

In Column 60, Lines 56-57, delete "$C_{40}H_{56}N_2O_5Si\ Na$" and insert -- $C_{40}H_{56}N_2O_5SiNa$ --
In Column 61, Line 19, delete "$C_{38}H_{51}FN_2O_4Si\ Na$" and insert -- $C_{38}H_{51}FN_2O_4SiNa$ --
In Columns 69-70, approximately Line 35, delete "Pd(dppf)(Cl$_2$, Cs$_2$CO$_3$" and insert -- Pd Cl$_2$(dppf)$_2$, Cs$_2$CO$_3$ --
In Column 73, approximately Lines 40-47, delete " 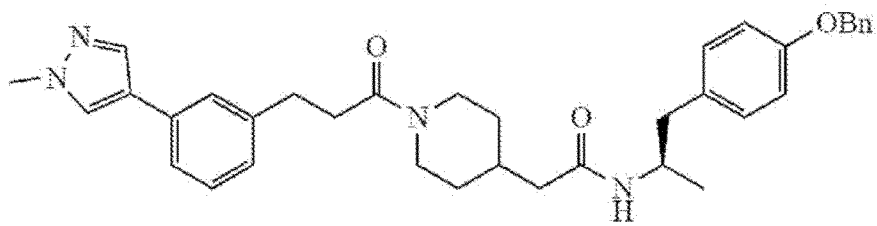 " and insert -- 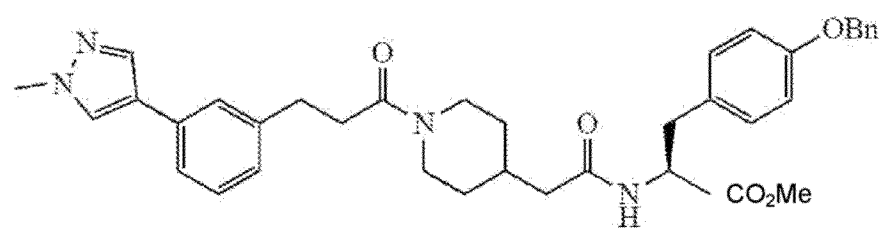 --

In Columns 81-82, approximately Lines 23-25, delete

" 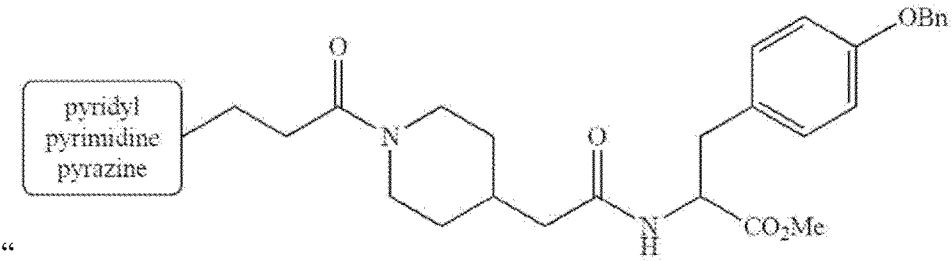 " and insert

CERTIFICATE OF CORRECTION (continued)
U.S. Pat. No. 11,685,725 B2

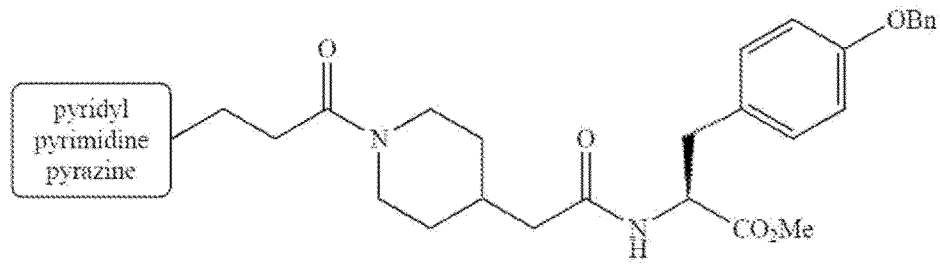

In Columns 81-82, approximately Lines 45-55, delete "

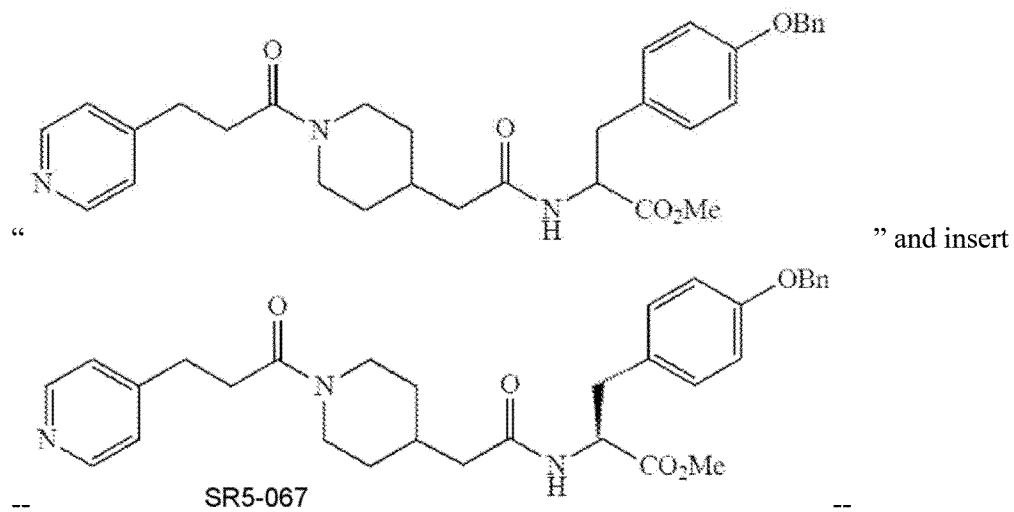

" and insert

-- SR5-067 --

In Columns 81-82, approximately Lines 45-55, delete "

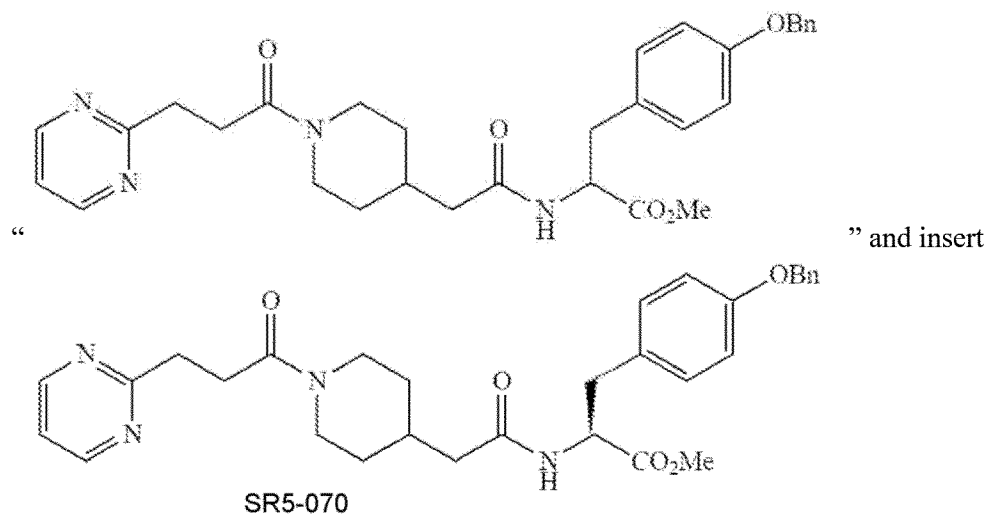

" and insert

-- SR5-070 --

CERTIFICATE OF CORRECTION (continued)
U.S. Pat. No. 11,685,725 B2

In Columns 81-82, approximately Lines 58-65, delete

" 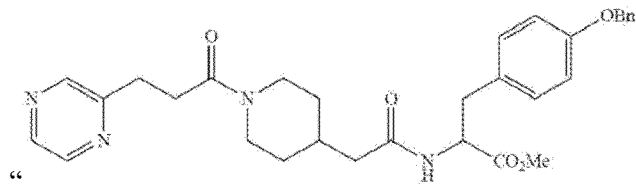 " and insert

-- 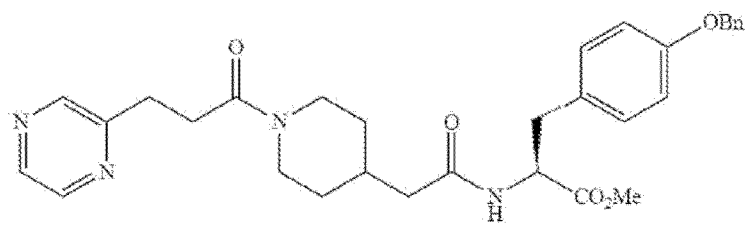 SR5-080 --

In Column 85, approximately Lines 36-44, delete

" 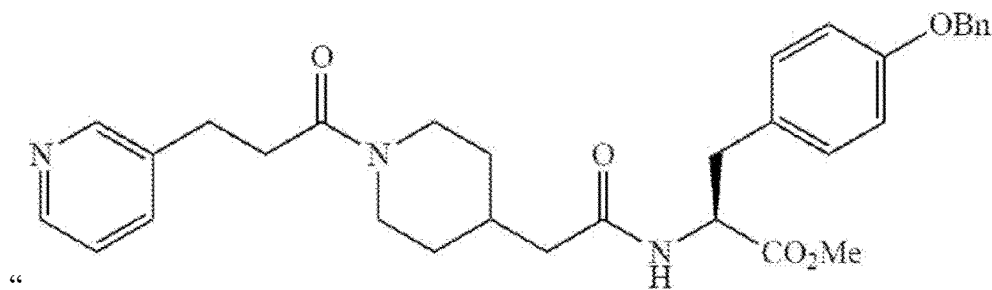 " and insert

-- 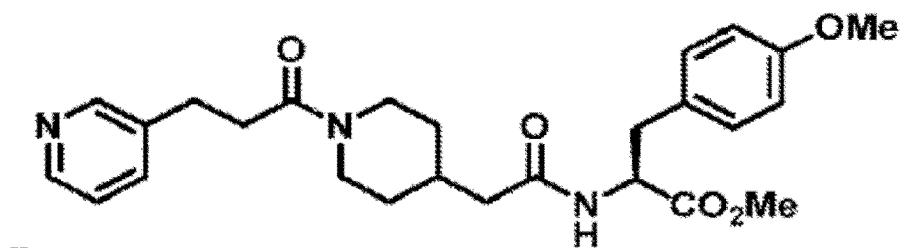 --

In Column 93, Line 51, delete "(FTTC" and insert -- (FITC --
In Column 94, Line 54, delete "DH5a" and insert -- DH5α --
In Column 94, Line 56, delete "DH5a" and insert -- DH5α --
In Column 96, Line 20, delete "L/" and insert -- μL/ --